US011786469B2

(12) United States Patent
Won

(10) Patent No.: US 11,786,469 B2
(45) Date of Patent: Oct. 17, 2023

(54) SILICA NANOPARTICLE COMPOSITION FOR DELIVERING BIOACTIVE MATERIAL OR PROTEIN SUCH AS A HUMAN PROTEASOME

(71) Applicants: LEMONEX INC., Seoul (KR); Cheolhee Won, Seoul (KR)

(72) Inventor: Cheolhee Won, Seoul (KR)

(73) Assignees: Cheolhee Won, Seoul (KR); LEMONEX INC., Seoul (KR)

( * ) Notice: Subject to any disclaimer, the term of this patent is extended or adjusted under 35 U.S.C. 154(b) by 0 days.

(21) Appl. No.: 15/328,121

(22) PCT Filed: Mar. 31, 2015

(86) PCT No.: PCT/KR2015/003209
§ 371 (c)(1),
(2) Date: Jan. 23, 2017

(87) PCT Pub. No.: WO2016/013751
PCT Pub. Date: Jan. 28, 2016

(65) Prior Publication Data
US 2017/0172923 A1    Jun. 22, 2017

(30) Foreign Application Priority Data
Jul. 22, 2014    (KR) .................. 10-2014-0092846

(51) Int. Cl.
*A61K 9/14*    (2006.01)
*A61K 47/02*    (2006.01)
(Continued)

(52) U.S. Cl.
CPC .............. *A61K 9/143* (2013.01); *A61K 9/145* (2013.01); *A61K 9/16* (2013.01); *A61K 39/395* (2013.01);
(Continued)

(58) Field of Classification Search
None
See application file for complete search history.

(56) References Cited

U.S. PATENT DOCUMENTS 4,179,337 A    12/1979 Davis et al.
4,495,285 A    1/1985 Shimizu et al.
(Continued)

FOREIGN PATENT DOCUMENTS

CN    101652126 A    2/2010
CN    101687632 A    3/2010
(Continued)

OTHER PUBLICATIONS

Lee, U-H., et al. Bull. Korean Chem. Soc. (2006), 27(6), 808-816.*
(Continued)

*Primary Examiner* — Kevin S Orwig
(74) *Attorney, Agent, or Firm* — The PL Law Group, PLLC

(57) ABSTRACT

A composition for delivering a bioactive material include a porous silica nanoparticle containing pores with an average pore diameter ranging from 1 nm to 100 nm, at least one of (i) a functional group which binds to the pore surface of the porous silica nanoparticle and gives the pore surface a negative charge or a positive charge, (ii) a ligand which binds to the pore surface of the porous silica nanoparticle and specifically binds to the bioactive material, and (iii) a combination of the functional group and the ligand, and a bioactive material having a size to be accommodated within the pores of the porous silica nanoparticle, the bioactive material bound to said at least one of the functional group and the ligand bound to the pore surface of the mesoporous silica nanoparticle and accommodated within the pores of the porous silica nanoparticle.

11 Claims, 40 Drawing Sheets

Specification includes a Sequence Listing.

(51) Int. Cl.
A61K 39/395 (2006.01)
A61K 47/40 (2006.01)
A61K 9/16 (2006.01)
B82Y 5/00 (2011.01)

(52) U.S. Cl.
CPC .............. A61K 47/02 (2013.01); A61K 47/40 (2013.01); B82Y 5/00 (2013.01)

(56) References Cited

U.S. PATENT DOCUMENTS

| | | | |
|---|---|---|---|
| 4,609,546 | A | 9/1986 | Hiratani |
| 4,766,106 | A | 8/1988 | Katre et al. |
| 11,129,796 | B2 | 9/2021 | Won |
| 2009/0181096 | A1 | 7/2009 | Ludwig |
| 2010/0104650 | A1 | 4/2010 | Lee et al. |
| 2010/0255103 | A1 | 10/2010 | Liong et al. |
| 2010/0266491 | A1* | 10/2010 | Farokhzad ........... A61K 9/5153 424/1.29 |
| 2011/0200595 | A1* | 8/2011 | Gerdes ............... C07K 16/2863 424/133.1 |
| 2011/0256184 | A1* | 10/2011 | Lei ........................ A61K 47/02 424/400 |
| 2012/0283379 | A1 | 11/2012 | Auger et al. |
| 2014/0014327 | A1 | 1/2014 | Badri et al. |
| 2014/0017327 | A1 | 1/2014 | Cheng et al. |
| 2015/0272885 | A1 | 10/2015 | Ashley et al. |
| 2018/0319822 | A1 | 11/2018 | Schoenfisch et al. |

FOREIGN PATENT DOCUMENTS

| | | |
|---|---|---|
| CN | 103751857 A | 4/2014 |
| CN | 105456198 A | 4/2016 |
| EP | 0 268 110 A1 | 5/1988 |
| EP | 0 270 799 A1 | 6/1988 |
| EP | 3 173 074 A1 | 5/2017 |
| EP | 3 659 585 A2 | 6/2020 |
| JP | 2013-006859 A | 1/2013 |
| JP | 2020-506972 A | 3/2020 |
| KR | 10-2010-0117433 A | 11/2010 |
| KR | 10-2011-0000297 A | 1/2011 |
| KR | 10-1057116 B1 | 8/2011 |
| KR | 10-2012-0025224 A | 3/2012 |
| KR | 10-2014-0010285 A | 1/2014 |
| KR | 10-2015-0014560 A | 2/2015 |
| KR | 10-2016-0011565 A | 2/2016 |
| KR | 10-2016-0137109 A | 11/2016 |
| KR | 10-1754798 B1 | 7/2017 |
| KR | 10-1762825 B1 | 7/2017 |
| KR | 10-1924519 B1 | 12/2018 |
| WO | WO 2005/097677 A1 | 10/2005 |
| WO | WO2008105773 A2 | 9/2008 |
| WO | WO 2009/113522 A1 | 9/2009 |
| WO | WO 2012/149376 A2 | 11/2012 |
| WO | WO 2016/013751 A1 | 1/2016 |
| WO | WO2016149378 A1 | 9/2016 |
| WO | WO 2017/008059 A1 | 1/2017 |

OTHER PUBLICATIONS

Guillet-Nicolas, R. et al. Adv. Funct. Mater. (2011), 21; 4653-4662.*
Zhao, D., et al. JACS (1998), 120; 6024-6036.*
Vallet-Regí, M., et al. Prog. Solid State Chem. (2008), 36; 163-191.*
Shin, H.-S., et al. Applied Mater. Interfaces (Jan. 2014), 6; 1740-1746.*
Gu, J. et al. J. Colloid Interface Sci. (2013), 407; 236-242.*
Office action dated Jun. 5, 2018 from Japan Intellectual Property Office in a counterpart Japanese Patent Application No. 2017-525486 (all the cited references are listed in this IDS.) (English translation is also submitted herewith).
Margarita D. Popova et al., "Carboxylic modified spherical mesoporous silicas as drug delivery carriers", International Journal of Pharmaceutics, vol. 436, No. 1-2, pp. 778-785, 2012.
Meng H. et al., "Engineered Design of Mesoporous Silica Nanoparticles to Deliver Doxorubicin and P-Glycoprotein siRNA to Overcome Drug Resistance in a Cancer Cell Line", ACS Nano, vol. 4, No. 8, pp. 4539-4550, 2010.
Lim JS et al., "Intracellular protein delivery by hollow mesoporous silica capsules with a large surface hole", Nanotechnology, vol. 23, Art No. 085101, pp. 1-11, 2012.
Tarn D. et al., "Mesoporous Silica Nanoparticle Nanocarriers: Biofunctionality and Biocompatibility." vol. 46, No. 3. pp. 792-801, 2013.
European Search Report for EP15823972.3 from European patent office in a counterpart European patent application.
Mahkam Mehrdad, "Synthesis and characterization of pH-sensitive silica nanoparticles for oral-insulin delivery", Current Drug Delivery, vol. 8, No. 6, pp. 607-611, 2011, Miyaneh, Iran, ISSN: 1875-5704, DOI: NLM21864258.
Mi-Hee Kim et al., "Facile Synthesis of Monodispersed Mesoporous Silica Nanoparticles with Ultralarge Pores and Their Application in Gene Delivery", ACS Nano (ACS Publications), vol. 5 No. 5, pp. 3568-3576, 2011 (Abstract is submitted herewith).
International Search Report for PCT/KR2015/003209.
Park, Hui Seong, "Novel Intracellular Protein Delivery Carriers Based on PH-Responsive Mesoporous Nanoparticles", Graduate school of Ewha Womans University, Doctoral Thesis, 2011. (English abstract is included in this reference.).
Kim, Se Mi, "RGD-and Hemagglutinin Peptide—conjugated Mesoporous Silica Nanoparticles in Doxorubin resistant MCF-7 Cells", Graduate school of Soongsil University, Master's Thesis, 2013. (English abstract is included in this reference.).
Choi, Ji Ung, "Multifunctional Silica-Iron Oxide Nanocontainers for Imaging and Drug Deliver", Graduate school of Inha University, Engineering Master's Thesis, 2013. (English abstract is included in this reference.).
Lin, Yu-Hsuan, Abstract of "Characterization on co-delivery of superoxide dismutase and glutathione peroxidase by using nanoparticles", National Taiwan University Thesis, 2014.
Igor I. et al., "Mesoporous Silica Nanoparticles for Intracellular Delivery of Membrane-Impermeable Proteins", Journal of the American Chemical Society vol. 129, pp. 8845-8849, 2007.
Yu-Shen Lin et al., Supporting Information, Chem. Mater. 2005, 17, 18, 4570-4573, attached hereto as Appendix 1, downloaded at https://pubs.acs.org/doi/suppl/10.1021/cm051014c/suppl_file/cm051014csi20050711_121101.pdf.
Marimar Bravo Cadena, "Application of Mesoporous Silica Nanoparticles for Biocide Delivery to Plants to Prevent Pre-Harvest Losses" A thesis submitted for the degree of Doctor of Philosophy, University of Oxford Mansfield College Department of Engineering, 2018.
J. Arbiol et al.,"Distributions of Noble Metal Pd and Pt in Mesoporous Silica", Applied Physics Letters, vol. 81, Issue 18, 2002, pp. 3449-3451.
Jonas G. Croissant et al., "Degradability and Clearance of Silicon, Organosilica, Silsesquioxane, Silica Mixed Oxide, and Mesoporous Silica Nanoparticles", Advanced Materials, vol. 29 (9), Jan. 2017.
Hironori Yamada et al., "Preparation of Colloidal Mesoporous Silica Nanoparticles with Different Diameters and Their Unique Degradation Behavior in Static Aqueous Systems", Chemistry of materials, vol. 24 (8), pp. 1462-1471, 2012.
Qianjun He et al., "The three-stage in vitro degradation behavior of mesoporous silica in simulated body fluid", Microporous and Mesoporous Materials, vol. 131, pp. 314-320, 2010.
Xinyue Huang et al., "Characterization and Comparison of Mesoporous Silica Particles for Optimized Drug Delivery", Nanomaterials and Nanotechnologies, vol. 4, (2), 2014.
Christopher R. Steven et al. "Bioinspired silica as drug delivery systems and their biocompatibility", Journal of Materials Chemistry B, vol. 2, No. 31, 2014(Jan. 1, 2014), pp. 5028-5042, XP055685292.

(56) References Cited

OTHER PUBLICATIONS

Wanyin Zhai et al., "Degradation of hollow mesoporous silica nanoparticles in human umbilical vein endothelial cells", J Biomed Mater Res Part B, May 7, 2012, 100B:1397-1403, Wiley Periodicals, Inc.

Yixian Zhou et al., "Mesoporous silica nanoparticles for drug and gene delivery", Acta Pharmaceutica Sinica B, (80): 165-177, 2018.

Fakhoury, Jean Raymond Garcia, "Porous silicon microparticles as an embolic agent for the treatment of hepatocellular carcinoma" The University of Texas at Austin, Dec. 31, 2011 (Abstract is submitted herewith.).

Kaasalainen, M. et al. "Size, Stability, and Porosity of Mesoporous Nanoparticles Characterized with Light Scattering" Nanoscale Research. Letters, vol. 12, No. 74, 2017.

Jadhav, S. A et al. "Porous Silica Particles: Synthesis, Physicochemical Characterization and Evaluation of Suspension Stability" Physical Chemistry: An Indian. Journal, vol. S1, No. 102, 2017.

Notice of allowance dated Jul. 12, 2022 from Japan Intellectual Property Office in a counterpart Japanese Patent Application No. 2021-056003 (all the cited references are listed in this IDS.).

Office action dated Jun. 7, 2022 from Japan Intellectual Property Office in a counterpart Japanese Patent Application No. 2021-075356 (all the cited references are listed in this IDS.).

Decision of Refusal dated Mar. 28, 2023 from Japan Intellectual Property Office in a counterpart Japanese Patent Application No. 2021-075356 (all the cited references are listed in this IDS.) (English translation is also submitted herewith.).

Youngjin Choi et al., "A Biodegradation Study of SBA-15 Microparticles in Simulated Body Fluid and in Vivo", Langmuir 2015, 31, pp. 6457-6462, DOI: 10.1021/acs.langmuir.5b01316.

Mamoru Mizutani et al., "Anomalous Pore Expansion of Highly Monodispersed Mesoporous Silica Spheres and Its Application to the Synthesis of Porous Ferromagnetic Composite" Chem. Mater., vol. 20, No. 14, 2008, pp. 4777-4782, DOI: 10.1021/cm702792e.

\* cited by examiner

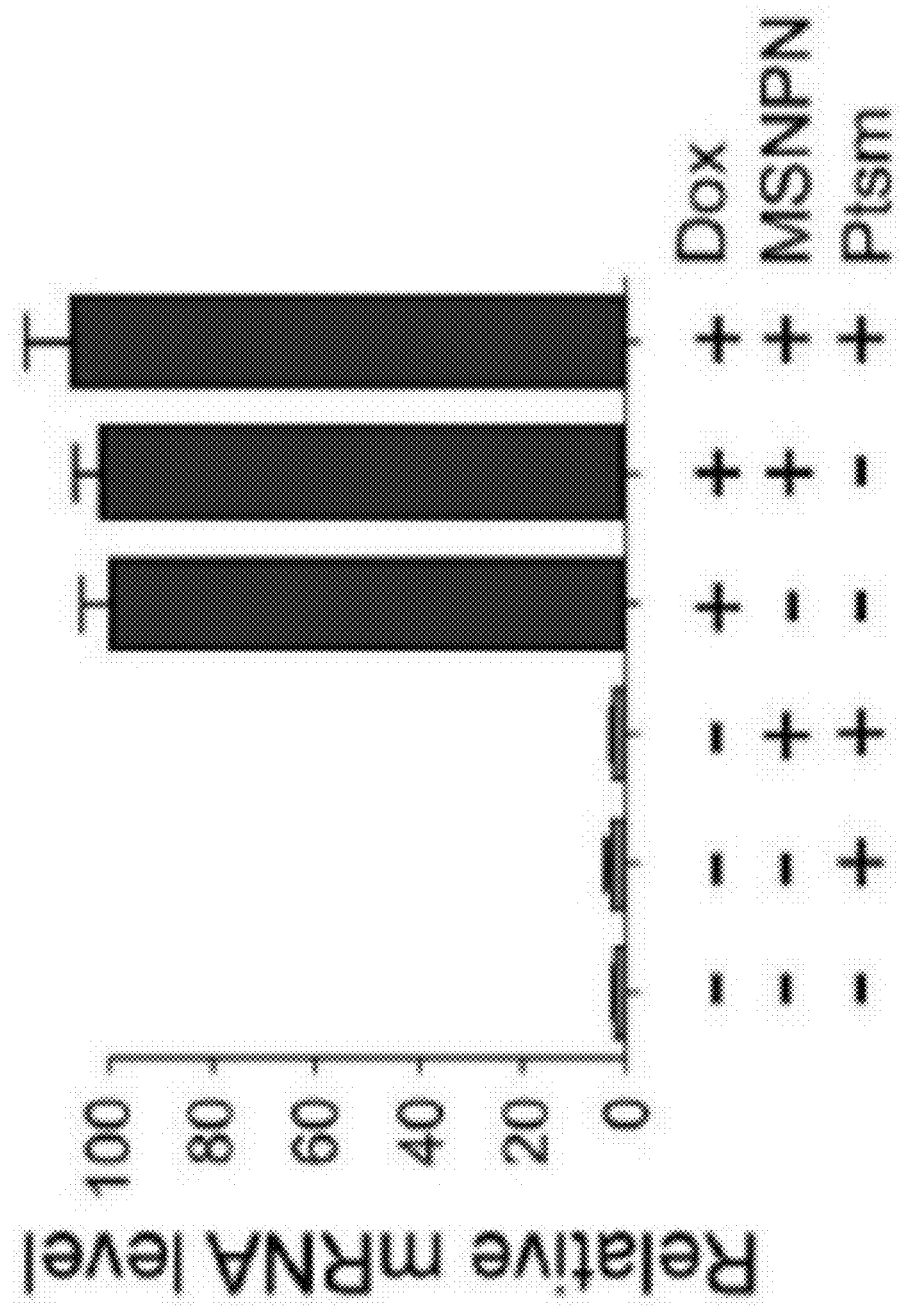

Complex = RNase + MSN
Complex was intratumorally injected one time in tumor-bearing mice Fig. 28b
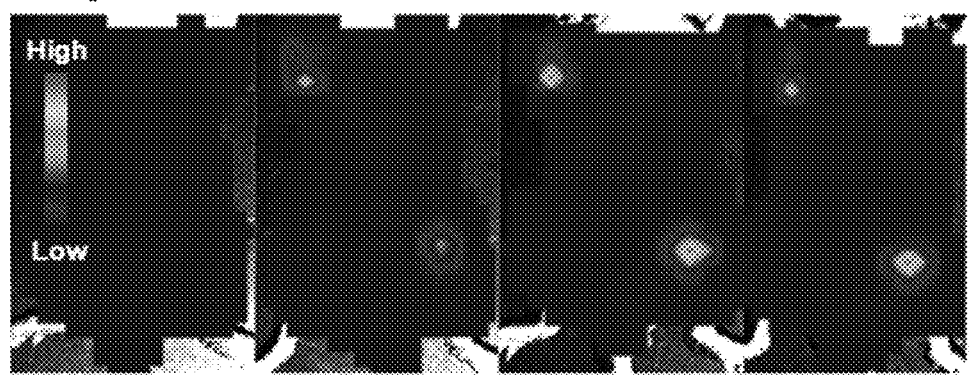
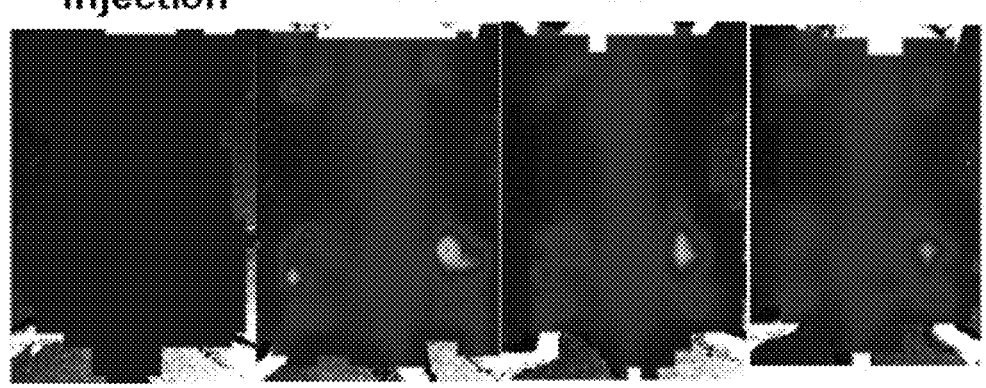

```
                         SEQUENCE LISTING

<160> NUMBER OF SEQ ID NOS: 42

<210> SEQ ID NO 1
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 1

Gly Arg Lys Lys Arg Arg Gln Arg Arg Arg Pro Pro Gln
1               5                   10

<210> SEQ ID NO 2
<211> LENGTH: 18
<212> TYPE: PRT
<213> ORGANISM: Artificial Sequence
<220> FEATURE:
<223> OTHER INFORMATION: pVEC

<400> SEQUENCE: 2

Leu Leu Ile Ile Leu Arg Arg Arg Ile Arg Lys Gln Ala His Ala His
1               5                   10                  15

Ser Lys

<210> SEQ ID NO 3
<211> LENGTH: 9
<212> TYPE: PRT
<213> ORGANISM: Artificial Sequence
<220> FEATURE:
<223> OTHER INFORMATION: TCP-1

<400> SEQUENCE: 3

Cys Thr Pro Ser Pro Phe Ser His Cys
1               5

<210> SEQ ID NO 4
<211> LENGTH: 12
<212> TYPE: PRT
<213> ORGANISM: Artificial Sequence
<220> FEATURE:
<223> OTHER INFORMATION: HAP-1

<400> SEQUENCE: 4

Ser Phe His Gln Phe Ala Arg Ala Thr Leu Ala Ser
1               5                   10
```

```
<210> SEQ ID NO 5
<211> LENGTH: 11
<212> TYPE: PRT
<213> ORGANISM: Artificial Sequence
<220> FEATURE:
<223> OTHER INFORMATION: HAP-2

<400> SEQUENCE: 5

His Ile Gln Leu Ser Pro Phe Gln Ser Trp Arg
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Target to Myeloid leukemia cells

<400> SEQUENCE: 6

Leu Lys Lys Pro
1

<210> SEQ ID NO 7
<211> LENGTH: 4
<212> TYPE: PRT
<213> ORGANISM: Artificial Sequence
<220> FEATURE:
<223> OTHER INFORMATION: Target to Embryonic stem cells

<400> SEQUENCE: 7

Glu Pro Lys Lys
1

<210> SEQ ID NO 8
<211> LENGTH: 4
<212> TYPE: PRT
<213> ORGANISM: Artificial Sequence
<220> FEATURE:
<223> OTHER INFORMATION: Target to Primary monocytes

<400> SEQUENCE: 8

Glu Leu Lys Lys
1

<210> SEQ ID NO 9
<211> LENGTH: 4
<212> TYPE: PRT
<213> ORGANISM: Artificial Sequence
<220> FEATURE:
<223> OTHER INFORMATION: Target to Amelanotic melanoma cells, ARN8

<400> SEQUENCE: 9

Pro Tyr Glu Glu
1

<210> SEQ ID NO 10
<211> LENGTH: 24
<212> TYPE: PRT
<213> ORGANISM: Artificial Sequence
<220> FEATURE:
<223> OTHER INFORMATION: Histatin 5

<400> SEQUENCE: 10

Asp Ser His Ala Lys Arg His His Gly Tyr Lys Arg Lys Phe His Glu
1               5                   10                  15
```

-continued

Lys His His Ser His Arg Gly Tyr
            20

<210> SEQ ID NO 11
<211> LENGTH: 27
<212> TYPE: PRT
<213> ORGANISM: Artificial Sequence
<220> FEATURE:
<223> OTHER INFORMATION: MPG

<400> SEQUENCE: 11

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 12
<211> LENGTH: 9
<212> TYPE: PRT
<213> ORGANISM: Artificial Sequence
<220> FEATURE:
<223> OTHER INFORMATION: cell-permeable peptide

<400> SEQUENCE: 12

Ala Arg Arg Arg Arg Arg Arg Arg Cys
1               5

<210> SEQ ID NO 13
<211> LENGTH: 9
<212> TYPE: PRT
<213> ORGANISM: Artificial Sequence
<220> FEATURE:
<223> OTHER INFORMATION: cell-permeable peptide

<400> SEQUENCE: 13

Arg Lys Lys Arg Arg Gln Arg Arg Arg
1               5

<210> SEQ ID NO 14
<211> LENGTH: 9
<212> TYPE: PRT
<213> ORGANISM: Artificial Sequence
<220> FEATURE:
<223> OTHER INFORMATION: cell-permeable peptide

<400> SEQUENCE: 14

Arg Arg Arg Arg Arg Arg Arg Arg Arg
1               5

<210> SEQ ID NO 15
<211> LENGTH: 20
<212> TYPE: PRT
<213> ORGANISM: Artificial Sequence
<220> FEATURE:
<223> OTHER INFORMATION: primer

<400> SEQUENCE: 15

Ala Ala Gly Gly Thr Gly Ala Cys Cys Thr Cys Cys Ala Ala Gly Thr
1               5                   10                  15

Gly Thr Gly Gly
            20

<210> SEQ ID NO 16
<211> LENGTH: 20
<212> TYPE: PRT
<213> ORGANISM: Artificial Sequence

```
<220> FEATURE:
<223> OTHER INFORMATION: primer

<400> SEQUENCE: 16

Gly Gly Gly Ala Cys Gly Thr Gly Gly Thr Gly Ala Thr Ala Thr
1               5                   10                  15

Thr Gly Thr Cys
            20

<210> SEQ ID NO 17
<211> LENGTH: 20
<212> TYPE: PRT
<213> ORGANISM: Artificial Sequence
<220> FEATURE:
<223> OTHER INFORMATION: primer

<400> SEQUENCE: 17

Gly Ala Gly Thr Cys Ala Ala Cys Gly Gly Ala Thr Thr Thr Gly Gly
1               5                   10                  15

Thr Cys Gly Thr
            20

<210> SEQ ID NO 18
<211> LENGTH: 20
<212> TYPE: PRT
<213> ORGANISM: Artificial Sequence
<220> FEATURE:
<223> OTHER INFORMATION: primer

<400> SEQUENCE: 18

Gly Ala Cys Ala Ala Gly Cys Thr Thr Cys Cys Cys Gly Thr Thr Cys
1               5                   10                  15

Thr Cys Ala Gly
            20

<210> SEQ ID NO 19
<211> LENGTH: 7
<212> TYPE: PRT
<213> ORGANISM: Artificial Sequence
<220> FEATURE:
<223> OTHER INFORMATION: Neuronal stem cells

<400> SEQUENCE: 19

Pro Phe Ser Ser Thr Lys Thr
1               5

<210> SEQ ID NO 20
<211> LENGTH: 13
<212> TYPE: PRT
<213> ORGANISM: Artificial Sequence
<220> FEATURE:
<223> OTHER INFORMATION: Melanoma cells

<400> SEQUENCE: 20

Cys Thr Val Ala Leu Pro Gly Gly Tyr Val Arg Val Cys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Chondrocyte cells

<400> SEQUENCE: 21
```

```
Asp Trp Arg Val Ile Ile Pro Pro Arg Pro Ser Ala
1               5                   10
```

<210> SEQ ID NO 22
<211> LENGTH: 9
<212> TYPE: PRT
<213> ORGANISM: Artificial Sequence
<220> FEATURE:
<223> OTHER INFORMATION: Angiogenic blood vasculature

<400> SEQUENCE: 22

```
Cys Asp Cys Arg Gly Asp Cys Phe Cys
1               5
```

<210> SEQ ID NO 23
<211> LENGTH: 11
<212> TYPE: PRT
<213> ORGANISM: Artificial Sequence
<220> FEATURE:
<223> OTHER INFORMATION: Various tumor cells

<400> SEQUENCE: 23

```
Cys Arg Gly Asp Lys Arg Gly Pro Asp Glu Cys
1               5                   10
```

<210> SEQ ID NO 24
<211> LENGTH: 5
<212> TYPE: PRT
<213> ORGANISM: Artificial Sequence
<220> FEATURE:
<223> OTHER INFORMATION: Angiogenic blood vessels

<400> SEQUENCE: 24

```
Arg Gly Asp Asn Val
1               5
```

<210> SEQ ID NO 25
<211> LENGTH: 11
<212> TYPE: PRT
<213> ORGANISM: Artificial Sequence
<220> FEATURE:
<223> OTHER INFORMATION: R9F2

<400> SEQUENCE: 25

```
Arg Arg Arg Arg Arg Arg Arg Arg Arg Phe Phe
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Decalysine

<400> SEQUENCE: 26

```
Lys Lys Lys Lys Lys Lys Lys Lys Lys Lys
1               5                   10
```

<210> SEQ ID NO 27
<211> LENGTH: 16
<212> TYPE: PRT
<213> ORGANISM: Artificial Sequence
<220> FEATURE:
<223> OTHER INFORMATION: Penetratin

<400> SEQUENCE: 27

```
Arg Gln Ile Lys Ile Trp Phe Gln Asn Arg Arg Met Lys Trp Lys Lys
```

<210> SEQ ID NO 28
<211> LENGTH: 27
<212> TYPE: PRT
<213> ORGANISM: Artificial Sequence
<220> FEATURE:
<223> OTHER INFORMATION: Transportan

<400> SEQUENCE: 28

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 29
<211> LENGTH: 11
<212> TYPE: PRT
<213> ORGANISM: Artificial Sequence
<220> FEATURE:
<223> OTHER INFORMATION: HIV-Tat

<400> SEQUENCE: 29

```
Tyr Ala Arg Ala Ala Ala Arg Gln Ala Arg Ala
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Hepatitis

<400> SEQUENCE: 30

```
Pro Leu Ser Ser Ile Phe Ser Arg Ile Gly Asp Pro
1               5                   10
```

<210> SEQ ID NO 31
<211> LENGTH: 28
<212> TYPE: PRT
<213> ORGANISM: Artificial Sequence
<220> FEATURE:
<223> OTHER INFORMATION: mPrP1

<400> SEQUENCE: 31

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25
```

<210> SEQ ID NO 32
<211> LENGTH: 11
<212> TYPE: PRT
<213> ORGANISM: Artificial Sequence
<220> FEATURE:
<223> OTHER INFORMATION: POD

<400> SEQUENCE: 32

```
Gly Gly Gly Ala Arg Lys Lys Ala Ala Lys Ala
1               5                   10
```

<210> SEQ ID NO 33
<211> LENGTH: 22
<212> TYPE: PRT
<213> ORGANISM: Artificial Sequence
<220> FEATURE:

```
<223> OTHER INFORMATION: ARF

<400> SEQUENCE: 33

Met Val Arg Arg Phe Leu Val Thr Leu Arg Ile Arg Arg Ala Cys Gly
1               5                   10                  15

Pro Pro Arg Val Arg Val
            20

<210> SEQ ID NO 34
<211> LENGTH: 23
<212> TYPE: PRT
<213> ORGANISM: Artificial Sequence
<220> FEATURE:
<223> OTHER INFORMATION: EB1

<400> SEQUENCE: 34

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 35
<211> LENGTH: 22
<212> TYPE: PRT
<213> ORGANISM: Artificial Sequence
<220> FEATURE:
<223> OTHER INFORMATION: Rath

<400> SEQUENCE: 35

Thr Pro Trp Trp Arg Leu Trp Thr Lys Trp His His Lys Arg Arg Asp
1               5                   10                  15

Leu Pro Arg Lys Pro Glu
            20

<210> SEQ ID NO 36
<211> LENGTH: 20
<212> TYPE: PRT
<213> ORGANISM: Artificial Sequence
<220> FEATURE:
<223> OTHER INFORMATION: CADY

<400> SEQUENCE: 36

Gly Leu Trp Arg Ala Leu Trp Arg Leu Leu Arg Ser Leu Trp Arg Leu
1               5                   10                  15

Leu Trp Arg Ala
            20

<210> SEQ ID NO 37
<211> LENGTH: 27
<212> TYPE: PRT
<213> ORGANISM: Artificial Sequence
<220> FEATURE:
<223> OTHER INFORMATION: MPG

<400> SEQUENCE: 37

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 38
<211> LENGTH: 27
<212> TYPE: PRT
<213> ORGANISM: Artificial Sequence
```

```
<220> FEATURE:
<223> OTHER INFORMATION: p

<400> SEQUENCE: 38

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 39
<211> LENGTH: 21
<212> TYPE: PRT
<213> ORGANISM: Artificial Sequence
<220> FEATURE:
<223> OTHER INFORMATION: Pep

<400> SEQUENCE: 39

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 40
<211> LENGTH: 21
<212> TYPE: PRT
<213> ORGANISM: Artificial Sequence
<220> FEATURE:
<223> OTHER INFORMATION: Pep

<400> SEQUENCE: 40

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 41
<211> LENGTH: 21
<212> TYPE: PRT
<213> ORGANISM: Artificial Sequence
<220> FEATURE:
<223> OTHER INFORMATION: Pep

<400> SEQUENCE: 41

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 42
<211> LENGTH: 4
<212> TYPE: PRT
<213> ORGANISM: Artificial Sequence
<220> FEATURE:
<223> OTHER INFORMATION: The sequence is synthesized.

<400> SEQUENCE: 42

Leu Leu Val Tyr
1
```

SILICA NANOPARTICLE COMPOSITION FOR DELIVERING BIOACTIVE MATERIAL OR PROTEIN SUCH AS A HUMAN PROTEASOME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/003209, filed Mar. 31, 2015, which claims priority to the benefit of Korean Patent Application No. 10-2014-0092846 filed in the Korean Intellectual Property Office on Jul. 22, 2014, the entire contents of which are incorporated herein by reference.

BACKGROUND

Technical Field

The present invention relates to a composition for delivering a bioactive material or a protein, and a use thereof.

Background Art

Drug delivery system refers to a medical and pharmaceutical technology to deliver a necessary amount of a drug such as, for example, a protein, a nucleic acid, or other low molecular substance, etc., while minimizing the side effects of existing drugs and maximizing the efficacy and effect. Such technology that can reduce cost and time required for the new drug development is being established as one field of high-technology which may create new added values among the medical and pharmaceutical field, as the technology is combined with nanotechnology recently, and advanced countries in technology such as U.S. and Japan, etc., led mainly by companies such as pharmaceutical companies, have given all their energies to the development of a drug delivery system as well as a new drug since late 1980s.

So far, a viral gene, a recombinant protein, liposome, a cationic polymer, and various types of nanoparticles and nano-substances have been used for drug delivery into an animal cell. However, many cationic liposomes and cationic polymers have been found to be unsuitable for clinical application due to their strong toxicity to cells. In addition, a method of chemically modifying the main chain of the nucleic acid has also been attempted for the stable plasma membrane penetration of nucleic acids. This method, however, is not suitable for clinical application since it takes high cost and long time, and requires labor-intensive process. As a meaningful approach, a drug delivery system (DDS) using various forms of nanoparticle including quantum dots, magnetic particles or gold nanoparticle has been developed. Related researches have been made such as, for example, "Image diagnostic drug delivery carrier using porous silicon particles and manufacturing method thereof (Korean Patent Laid-Open Publication No. 2010-0117433)" etc. However, these particles have the disadvantages that they show toxicity to cells, have a structure which is not easy to introduce a biopolymer such as nucleic acids etc., and their efficiency of introduction into cells is low.

An efficient protein delivery system is needed for the study of protein function in cells or for intracellular delivery of proteins. However, unlike nucleic acids such as DNA and RNA, which are commonly negatively charged, proteins do not have a common charge and are unstable, and therefore easily denatured. Accordingly, a generally applicable protein delivery system has not yet been developed. With the currently developed protein delivery systems, it is difficult to maintain the activity of a protein, and thus the system cannot be commonly applied to various proteins, leading to the restrictions in their usage.

SUMMARY

One embodiment of the present invention relates to a composition for delivering a bioactive material or a protein, and a use thereof.

In one embodiment of the present invention, there is provided a composition for delivering a protein including a mesoporous silica nanoparticle, which delivers the protein into a target cell by introducing the protein into a pore of the mesoporous silica nanoparticle, inhibits the protein from being degraded by an enzyme in vivo during such delivering process, and promotes the introduction of the bioactive material into a cell or the selective introduction of the bioactive material into a specific cell by binding an antibody, a ligand, a cell-permeable peptide or an aptamer to the nanoparticle's surface; a use (for example, a pharmaceutically acceptable use) of said composition for delivering a protein; and a method for delivering a protein using said composition.

However, the problems to be solved by the present invention are not limited to the above-mentioned problems, and other matters not mentioned above may be clearly understood by those skilled in the art from the following description.

One embodiment of the present invention relates to a composition for delivering a bioactive material or a protein, and a use thereof.

In one embodiment of the present invention, there is provided a composition for delivering a protein including a mesoporous silica nanoparticle, which delivers the protein into a target cell by introducing the protein into a pore of the mesoporous silica nanoparticle, inhibits the protein from being degraded by an enzyme in vivo during such delivering process, and promotes the introduction of the bioactive material into a cell or the selective introduction of the bioactive material into a specific cell by binding an antibody, a ligand, a cell-permeable peptide or an aptamer to the nanoparticle's surface; a use (for example, a pharmaceutically acceptable use) of said composition for delivering a protein; and a method for delivering a protein using said composition.

However, the problems to be solved by the present invention are not limited to the above-mentioned problems, and other matters not mentioned above may be clearly understood by those skilled in the art from the following description.

According to one embodiment of the present invention, composition for delivering a protein or a bioactive material in a highly efficient manner may be provided. The composition for delivering a protein or a bioactive material according to one embodiment of the present invention delivers the material in a highly efficient manner since it introduces a protein or a bioactive material into the inside or outside of the pore of the mesoporous silica nanoparticle, which reduces the environmental influence when the protein or the bioactive material is introduced into a cell, thereby maintaining the structure of the protein or the bioactive material stably. In addition, since the composition for delivering a protein or a bioactive material further includes an antibody, a ligand, a cell-permeable peptide or an aptamer bound to a surface of the mesoporous silica nanoparticle (such as, but not limited to, the outer surface of the nanoparticle), it may remarkably increase the efficiency of introducing a material into a cell, or selectively introduce a material into a target cell.

In one embodiment of the present invention, the composition for delivering a protein or a bioactive material may be prepared in a simple and cost effective way since the protein or the bioactive material may be introduced into a pore of the mesoporous silica nanoparticle by just mixing a solution containing the mesoporous silica nanoparticle and the protein or the bioactive material, with no need to make a chemical bond or a bridging bond, or conduct a complex purification and separation process.

In one embodiment of the present invention, the silica nanoparticle has high monodispersity and excellent biocompatibility without showing cytotoxicity, and thus may be clinically useful for treating a disease.

BRIEF DESCRIPTION OF DRAWINGS

FIG. 22a is a graph showing the tau control after translation by external proteasome.

FIGS. 28a and 28b are, respectively, a mouse model, and a fluorescence image for the evaluation of antibody delivery regarding a composition for delivering a protein according to one embodiment of the present invention.

DETAILED DESCRIPTION

Figure 1:
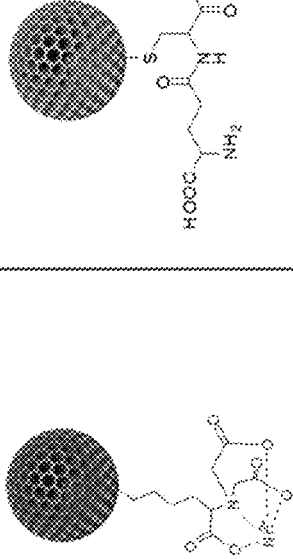
FIG. 1 shows an example of a surface-modified silica nanoparticle according to one embodiment of the present invention.

Hereinafter, embodiments and Examples of the present invention will be described in detail with reference to the accompanying drawings so that inventive concept may be readily implemented by those with ordinary skills in the art.

However, it is to be noted that the present disclosure is not limited to the embodiments and the Examples described herein but may be realized in various other ways. In the drawings, certain parts not directly relevant to the description are omitted to explain the present invention clearly, and like reference numerals denote like parts throughout the whole specification.

Throughout the whole specification, the term "on" that is used to designate a position of one element with respect to another element includes both a case that the one element is adjacent to the another element and a case that any other element exists between these two elements.

Throughout the whole specification, the term "includes or includes" means that one or more other components may be comprised or included not excluding such other components, unless specified otherwise. Throughout the whole specification, the terms "about or approximately" or "substantially" or the like are intended to have meanings close to numerical values when unique allowable manufacturing and substance errors are presented to the mentioned meaning, and intended to prevent accurate or absolute numerical values disclosed for understanding of the present invention from being illegally or unfairly used by any unconscionable third party. Throughout the whole specification, the term "step of" does not mean "step for."

Throughout the whole specification, the term "combination of" included in Markush type description means mixture or combination of one or more components selected from a group consisting of components described in Markush type and thereby means that the disclosure includes one or more components selected from the Markush group.

Throughout the whole specification, the description of "A and/or B" means "A or B, A and B."

Throughout the whole specification, "bioactive material" is meant to include any agent that may affect the recipient (an animal subject) after being administered physically, physiologically, mentally, biochemically, biologically, or other body functions in a positive or negative manner.

For example, the 'bioactive material' may include, but not limited to, drugs, proteins, peptides, miRNA, siRNA, plasmid DNA, small molecules, antibodies, viruses, microorganisms, somatic cell nuclei, cell organelles, the mitochondria, enzymes, supplemental nutrients, vitamins, natural products, extracts, or other active agents. The bioactive material is selected from the group consisting of proteins, peptides, nucleosides, nucleotides, endogenous ligands, neurotransmitters, hormones, autacoids, cytokines, antiviral agents, antineoplastic agents, antibiotics, oxygen-enriching agent, oxygen-containing agent, anti-epileptic drug, and anti-inflammatory drugs. For example, the bioactive material may be selected from the group consisting of calcitonin, cyclosporin, insulin, oxytocin, tyrosine, enkephalin, thyrotropin releasing hormones, follicle stimulating hormones, luteinizing hormones, growth hormones, arachidonic acid, platelet activating factor (PAF), angiotensin, kinin, prostaglandin, leukotrienes, thoursomboxane, and eicosanoids, vasopressin and vasopressin analogs, catalase, superoxide dismutase, interleukin, interferon, TGF-beta, BMP, colony stimulating factor, tumor necrosis factor, tumor necrosis factor inhibitor, and melanocyte-stimulating hormone. The bioactive material may include an Alzheimer antagonist or vaccine. The bioactive material for treating Alzheimer's disease may include memantine hydrochloride (AXURA® by Merz Pharmaceuticals), donepezil hydrochloride (ARICEPT® by Eisai Co. Ltd.), rivastigmine tartrate (EXELON® by Novartis), galantamine hydrochloride (REMINYL® by Johnson & Johnson), or tacrine hydrochloride (COGNEX® by Parke Davis). The bioactive material is selected from the group consisting of chondroitin sulfate, hyaluronic acid, growth factor and protein with a pharmaceutically effective amount.

For example, the bioactive material may include insulin or insulin analog. The bioactive material is selected from the group consisting of an insulin sensitizer, an insulin secretagogue, a GLP-1 analog, GLP-2, GLP-2 analog, an inhibitor of dipeptidyl peptidase 4 (DPP-4 inhibitor), exenatide, liraglutide, albiglutide, or taspoglutide, alpha-glucosidase inhibitors, amylin analog, sodium-glucose co-transporter type 2 (SGLT2) inhibitors, benfluorex, and tolrestat. In a further embodiment, the insulin-containing nanoparticle includes a trace amount of zinc or calcium, or is treated with an enteric coating. In one embodiment, the bioactive material is selected from the group consisting of, but not limited to, a non-insulin exenatide, a non-insulin pramlintide, insulin, insulin analog, or combinations thereof.

For example, the bioactive material may also be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, aldosterone, hydrocortisone, cortisone, estradiol, estrogen, a progesterone, testosterone, tyroxine, and synthetic analogues, modifications and pharmaceutically active fragments thereof, monoclonal antibodies and soluble vaccines. Growth hormone (GH) is a peptide hormone that stimulates growth and cell reproduction in humans and other animals. It is a 191-amino acid, single chain polypeptide hormone which is synthesized, stored, and secreted by the somatotroph cells within the lateral wings of the anterior pituitary gland.

For example, the bioactive material is selected from the group consisting of cytotoxic drugs, anti-viral drugs, antineoplastic drugs, anti-inflammatory drugs, antibiotics, analgesic drugs, drugs acting on the CNS, proton pump inhibitors, angiotensin converting enzyme inhibitor, angiotensin receptor antagonists, calcium antagonists, histamine receptor antagonists, cholesterol biosynthesis inhibitors, therapeutic agents for diabetes or Alzheimer's disease, immunosuppressive agents, synthetic antibacterial agents, anti-tumor agents, or any combinations thereof. The active drug moiety may include anti-metabolites masquerade as purines, cisplatin, carboplatin, oxaliplatin, mechlorethamine, cyclophosphamide, chlorambucil, ifosfamide, vincristine, vinblastine, vinorelbine, vindesine, podophyllotoxins, etoposide teniposide, docetaxel, or paclitaxel.

Throughout the whole specification, the term "protein" shall be understood to encompass not only target specific proteins, but also immunoglobulins, glycoproteins, antibodies, polypeptides, enzymes, peptides or the like. Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, interferon-alpha, interferon-beta, interferon-gamma, lectin, sugar binding proteins, glycoproteins, SUMO proteins preferably interferons, lectins as described in more detail below, colony stimulating factors including granulocyte colony stimulating factors, platelet derived growth factors and phospholipase-activating protein (PLAP). Other proteins of general biological or therapeutic interest include insulin, neovascularization inducers, e.g. VEGF, erythropoietin, plant proteins such as lectin and ricin, tumor necrosis factors and related proteins, growth factors such as transforming growth factors, such as TGFα or TGFβ and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. The protein portion is selected from the group consisting of immunoglobulins, glycoproteins, antibodies, polypeptides, enzymes, peptides, interferons (INF), interleukins, hormones, somatomedin, erythropoietin, pigmentary hormones, hypothalamic releasing factors, antidiuretic hormones, prolactin, choriogonadotropin, follicle-stimulating hormones, thyroid-stimulating hormones, or tissue plasminogen activating agents.

Examples of the protein may include fluorescent proteins, horseradish peroxidase (HRP), caspase-3, lipase, photolyase, superoxide dismutase (SOD), botulinum toxin, thyamidine kinase from herpes simplex virus (HSV-TK), caspase, vascular endothelial growth factor (VEGF), urate oxidate, beta-glucosidase, beta-hexosaminidase, a murine anti-CD3 antibody or the like.

Hereinafter, embodiments of the present invention will be described, but the present invention may not be limited thereto.

In one aspect of the present invention, there is provided a composition for delivering a protein including: a mesoporous silica nanoparticle containing pores with an average pore diameter ranging from about 1 nm to about 100 nm; and a functional group which binds to an inner or outer surface of the pore of the mesoporous silica nanoparticle and gives a surface negative charge or a positive charge or a ligand which binds to an inner or outer surface of the pore of the mesoporous silica nanoparticle and specifically binds to a protein.

A conventional mesoporous silica nanoparticle contains pores with an average pore diameter of only a few nm, and thus has a disadvantage that a biopolymer such as a protein cannot be sufficiently introduced into the pore. However, a mesoporous silica nanoparticle according to one embodiment of the present invention not only has pores with a larger average pore diameter compared to a conventional mesoporous silica nanoparticle for delivering a drug, but allows a protein to be adsorbed or loaded to the functional group giving surface negative charge or positive charge or the ligand which specifically binds to a protein on an inner or outer surface of the pore. Thus a bioactive material or a protein can be more easily included inside or outside of the pore. In addition, a mesoporous silica nanoparticle according to one embodiment of the present invention not only has pores with an expanded size, but also has the pores throughout the entire outer and inner surfaces of the particle even including the deep inside of the particle, and thus a bioactive material or a protein can be more easily included in the pore on the outer and inner surface of the particle.

In one embodiment of the present invention, the ligand which specifically binds to the protein may include, but not be limited to, nickel, nickel-nitrilotriacetic acid (NTA), glutathione, dextrin, biotin or streptavidin.

In one embodiment of the present invention, the composition for delivering a protein may include a protein which is adsorbed or loaded within the mesoporous silica nanoparticle, wherein the tag of the protein is bound to a ligand which is bound on a pore surface of the mesoporous silica nanoparticle, but it may not be limited thereto.

In one embodiment of the present invention, a composition for delivering a protein may include a protein adsorbed or loaded within the pore of the silica particle by an electrostatic interaction between a ligand giving a surface negative charge or positive charge and the protein, but it may not be limited thereto.

In one embodiment of the present invention, the inner or outer surface of the pore of the mesoporous silica nanoparticle may be modified to exhibit anionic and/or cationic charges, but it may not be limited thereto. Accordingly, the protein may be adsorbed or loaded within the pore by an electrostatic interaction between the inner or outer surface of the pore exhibiting anionic and/or cationic charges, but it may not be limited thereto. The surface-modification of the inner or outer surface of the pore of the mesoporous silica nanoparticle to exhibit anionic and/or cationic charges may be adjusted according the pI value of a protein to be adsorbed or loaded, but it may not be limited thereto.

In one embodiment of the present invention, the composition for delivering a protein may further include an antibody, a ligand, a cell-permeable peptide or an aptamer bound to a surface of the mesoporous silica nanoparticle, but it may not be limited thereto. For example, the antibody, the ligand, the cell-permeable peptide or the aptamer may be bound to the outer surface of the mesoporous silica nanoparticle, but it may not be limited thereto. The antibody, the ligand, the cell-permeable peptide or the aptamer allows the composition within which a protein is adsorbed or loaded to be transported into a target cell.

In one embodiment of the present invention, the protein may be selected from the group consisting of a protein complex including proteasome, etc.; various enzymes such as caspase, ribonuclease (RNase), kinase and phosphatase, etc.; and various antibodies, but it may not be limited thereto. For example, the protein may include a horseradish peroxidase (HRP), caspase-3, lipase, photolyase, super oxide dismutase (SOD), botulinum toxin, thymidine kinase from herpes simplex virus (HSV-TK), caspase, vascular endothelial growth factor (VEGF), urate oxidate, beta-glucosidase, beta-hexosaminidase, a murine anti-CD3 antibody or the like, but it may not be limited thereto.

In one embodiment of the present invention, the protein may be selected from the group consisting of an endogenous ligand, a systemic hormone, a cytokine, a chemokine, a neurotransmitter, autacoid, membrane protein, a cytoplasmic proteins, a nuclear protein, a receptor, an enzyme, a blood proteins, a synthetic protein, a synthetic peptide, a regulatory factor associated with a normal healing process such as a growth factor and other proteins that control differentiation and proliferation of a cell, and a growth factor reported to have an ability to heal a wound, the neurotransmitter being selected from the group consisting of dopamine, noradrenaline, adrenaline, acetylcholine, GABA, serotonin, histamine, enkephalin, somatostatin, or an amine-based neurotransmitter such as substance P, etc., or a peptide neurotransmitter, etc., but it may not be limited thereto. The cytokine and peptide hormone may be selected from the group consisting of peptide hormones, amino acid hormones, steroid hormones, transforming growth factor-β superfamily (TGF-β) protein, macrophage-colony forming-stimulating factor (M-CSF) and the protein complex such as proteasome, etc., various enzymes such as caspase, ribonuclease, kinase and phosphatase, and various antibodies, but it may not be limited thereto.

In one embodiment of the present invention, the protein may be derived from the cells of protozoa, microbes, viruses, fish, deep sea creatures, amphibians, reptiles, mammals, extraterrestrial plants and animals, but it may not be limited thereto.

In one embodiment of the present invention, the composition includes a pharmaceutically accepted carrier. The pharmaceutically accepted carrier comprised in the composition of the present invention is one conventionally used for formulating a composition, which includes, but not limited to, lactose, dextrose, sucrose, sorbitol, mannitol, starches, gum acacia, calcium phosphate, alginates, gelatin, calcium silicate, crystallite cellulose, polyvinylpyrrolidone, cellulose, water, syrup, methyl cellulose, methyl and propyl-hydroxy benzoate, talc, magnesium stearate and mineral oil, etc. The pharmaceutical composition of the present invention may further comprise, but not limited to, a lubricant, a humectant, a sweetening agent, a flavoring agent, an emulsifier, a suspension agent, a preservative, etc., in addition to the above components. Suitable pharmaceutically accepted carrier and formulation are described in detail in [Remington's Pharmaceutical Sciences, 19th ed., 1995].

In one embodiment of the present invention, the pharmaceutical composition may be administered orally or parenterally, and in the case of parenteral administration, it may be administered by intravenous injection, subcutaneous injection, intramuscular injection, intraperitoneal injection, and transdermal administration, etc.

A suitable dose of the pharmaceutical composition according to one embodiment of the present invention may vary depending on formulation methods, administration methods, the patient's age, body weight and sex, severity of diseases, diet, administration time, administration route, an excretion rate and responsiveness to the pharmaceutical composition. The daily dosage of the pharmaceutical composition in accordance with the present invention may be in the range of, for example, about 0.0001 mg/kg to about 100 mg/kg.

In one embodiment of the present invention, according to any conventional method easily implementable by one of ordinary skill in the art, the pharmaceutical composition may be formulated into a unit dosage form or enclosed in a multi-dose container, together with a pharmaceutically acceptable carrier and/or vehicle. The formulation may be a solution in oil or aqueous media, a suspension, an emulsion or a syrup, extracts, powders, granules, tablets or capsules, which may further include a dispersing agent or a stabilizer.

In other aspect of the present invention, there is provided a composition for delivering a bioactive material including: a mesoporous silica nanoparticle containing pores with an average pore diameter ranging from about 1 nm to about 100 nm; a functional group (ligand) which binds to an inner or outer surface of the pore of the mesoporous silica nanoparticle and gives a surface negative charge or positive charge, or a ligand which binds to an inner or outer surface of the pore of the mesoporous silica nanoparticle and specifically binds to a protein; and a bioactive material bound to the ligand.

In one embodiment of the present invention, the ligand which specifically binds to a bioactive material may include nickel, nickel-NTA, glutathione, dextrin, biotin or streptavidin, but it may not be limited thereto.

In one embodiment of the present invention, the bioactive material may be adsorbed or loaded within the pore by an electrostatic interaction, but it may not be limited thereto.

In one embodiment of the present invention, the bioactive material may include a drug, a protein, a peptide, miRNA, siRNA, an enzyme, a supplementary nutrient, a vitamin, a natural product or an extract, but it may not be limited thereto.

In one embodiment of the present invention, the composition for delivering a bioactive material may further include an antibody, a ligand, a cell-permeable peptide or an aptamer bound to a surface of the mesoporous silica nanoparticle, but it may not be limited thereto.

In one embodiment of the present invention, there is provided a method for delivering a bioactive material including introducing the composition for delivering a bioactive material into a target cell, and thus the composition can be utilized for a pharmaceutical use.

In one embodiment of the present invention, there is provided a food composition for preventing or treating a disease or a symptom, which includes the mesoporous silica nanoparticle of FIG. 1 or a composition for delivering a bioactive material of the present invention.

In one embodiment of the present invention, the food composition may be any food product such as, but not limited to, a health-functional food, a nutritional supplement, a nutrient, a pharmafood, a health food, a nutraceutical, a designer food or food additives. For example, the food may be meats, sausages, breads, chocolates, candies, snacks, cookies, pizza, ramen, other noodles, gums, dairy products including ice creams, various soups, beverages, teas, health drinks, alcoholic beverages, vitamin complexes, and the like.

In one embodiment of the present invention, the food composition includes components which are added conventionally when food is prepared, such as, for example, proteins, carbohydrates, fatty acids, nutrients, seasoning agents and flavoring agents. Examples of the carbohydrate may include monosaccharides (e.g., glucose, fructose); disaccharides (e.g., maltose, sucrose, etc.); oligosaccharides; polysaccharides (e.g., common sugars including dextrin, cyclodextrin, etc.); and sugar alcohols (e.g., xylitol, sorbitol, erythritol, etc.). The formulation of flavoring agent may use natural flavoring agents [e.g., thaumatin, stevia extract (e.g., rebaudioside A, glycyrrhizin), etc.] and synthetic flavoring agents (e.g., saccharine, aspartame, etc.)

In one embodiment of the present invention, the food composition may include various nutrients, vitamins, minerals (electrolytes), dietary components, flavoring agents such as synthetic flavoring agents and natural flavoring agents, coloring agents and fillers (cheese, chocolate, etc.), pectic acid and its salts, alginic acid and its salts, organic acid, protective colloidal thickeners, pH modifiers, stabilizers, antiseptics, glycerin, alcohol, carbonating agent used in a carbonated beverages, or the like. For example, in one embodiment of the present invention, if a food composition is manufactured as a beverage, the food composition may further include citric acid, liquid fructose, sugars, glucose, acetic acid, malic acid, fruit syrup, various plant extracts, and the like.

In one embodiment of the present invention, there is provided a cosmetic composition (functional cosmetic composition) for preventing or ameliorating a disease, which includes the mesoporous silica nanoparticle of FIG. 1 or a composition for delivering a bioactive material of the present invention.

In one embodiment of the present invention, the cosmetic composition may be prepared in any conventional form in the art, by including any ingredients conventionally used in the art in addition to its active ingredient, which may include a conventional additive for preparing cosmetics such as, for example, an antioxidant, a stabilizer, a solubilizer, a vitamin, a pigment and a perfume.

A conventional mesoporous silica nanoparticle contains pores with an average pore diameter of only a few nm, and thus has a disadvantage that a bioactive material such as a protein cannot sufficiently enter into the pore. However, a mesoporous silica nanoparticle according to one embodiment of the present invention not only has pores with an expanded average pore diameter compared to a conventional mesoporous silica nanoparticle for delivering a drug, but allows a protein to be adsorbed or loaded to the surface negative charge or positive charge of an inner or outer surface of the pore, or to the ligand which specifically binds to a protein, and thus, a bioactive material or a protein can be more easily included inside or outside of the pore. In addition, a mesoporous silica nanoparticle according to one embodiment of the present invention not only has pores with an expanded size, but also has expanded pores formed in the entire outer and inner surfaces of the particle and even in the deep inside of the particle, and thus, a bioactive material or a protein can be more easily included in the pore at the outer or inner surface of the particle.

According to one embodiment of the present invention, a bioactive material or a protein may be included inside or outside of the pore of the mesoporous silica nanoparticle, but it may not be limited thereto.

According to one embodiment of the present invention, the mesoporous silica nanoparticle may be surface-modified, but it may not be limited thereto.

In one embodiment of the present invention, the inner or outer surface of the pore of the mesoporous silica nanoparticle may be modified to exhibit anionic and/or cationic charges, but it may not be limited thereto. Accordingly, the bioactive material may be adsorbed or loaded within the pore by an electrostatic interaction with the inner or outer surface of the pore exhibiting anionic and/or cationic charges, but it may not be limited thereto. The surface-modification of the inner or outer surface of the pore of the mesoporous silica nanoparticle to exhibit anionic and/or cationic charges may be adjusted according the pI value of the bioactive material to be adsorbed or loaded, but it may not be limited thereto.

In one embodiment of the present invention, if the inner surface of the pore of the mesoporous silica nanoparticle is modified to exhibit anionic charges (for example, in the case of surface-modification with a silanol, a phosphate, a carboxylate, etc.), the nanoparticle may be used for adsorbing or loading a bioactive material having cations.

In one embodiment of the present invention, if the inner surface of the pore of the mesoporous silica nanoparticle is modified to exhibit cationic charges (for example, in the case of surface-modification with an amine group, a cationic polymer, etc.), the nanoparticle may be used for adsorbing or loading the bioactive material having anions.

In one embodiment of the present invention, if the inner surface of the pore of the mesoporous silica nanoparticle is modified with a substance binding to a specific tag or a ligand (for example, in the case of surface-modification by nickel-NTA, glutathione, dextrin, streptavidin, avidine, etc., which can respectively bind to his-tag, GST, MBP, biotin, or biotin tag), the nanoparticle can be used for adsorbing or loading a bioactive material having such specific tag, but it is not be limited thereto.

In one embodiment of the present invention, the outer surface of the mesoporous silica nanoparticle may be modified with the substance or the ligand used in the surface-modification of the inner surface of the pore, but it is not be limited thereto.

In one embodiment of the present invention, the outer surface of the mesoporous silica nanoparticle may be modified with a cell-permeable peptide (to increase the efficiency of intracellular delivery), polyethylene glycol (to prevent non-selective adsorbing or loading of a biomolecule to the outer surface of the particle and the aggregation of the particles), phosphatidyl amine, an antibody, an aptamer, or a ligand etc., but it is not be limited thereto. For example, the antibody, aptamer, or ligand, etc. makes it possible for the composition for delivering a bioactive material or a protein to be selectively delivered to a specific cell or a specific organ.

According to one embodiment of the present invention, as shown in FIG. 1, the mesoporous silica nanoparticle may be surface-modified with nickel, nickel-NTA, glutathione, or biotin, but it may not be limited thereto. A tag in the bioactive material may bind to the pore of the mesoporous silica nanoparticle to be efficiently loaded within the pore. For example, in case that the mesoporous silica particle is surface-modified with nickel or nickel-NTA, the bioactive material may be adsorbed or loaded within the pore by a non-covalent interaction between nickel of the mesoporous silica nanoparticle and His-tag of the bioactive material. For the adsorbing or loading of a bioactive material having GST-tag, mesoporous silica nanoparticle may be surface-modified with glutathione, but it may not be limited thereto.

According to one embodiment of the present invention, there is provided a composition for delivering a bioactive material which includes a bioactive material adsorbed or loaded to the mesoporous silica nanoparticle having expanded pores, but it may not be limited thereto.

In the mesoporous silica nanoparticle according to one embodiment of the present invention, its surface and/or inside of the pore of the nanoparticle may exhibit a positive charge or negative charge, and thus it is possible to attach a protein exhibiting a positive charge and/or a bioactive material exhibiting a negative charge to the pore of the mesoporous silica nanoparticle. In addition, a mesoporous silica nanoparticle of the present invention has a large average pore diameter, which allows accommodation of a bioactive material with a large size. That is, the protein can be easily introduced into a cell without regard to the surface charge or the size thereof.

For example, the mesoporous silica nanoparticles may possess monodispersity, but it may not be limited thereto. The monodispersity property indicates molecular weight or particle size within extremely narrow range distribution, and especially the monodispersity of nanoparticles is essential for designing a systematic drug delivering system with respect to the size of the nanoparticles. The monodispersity property may be a factor determining the intracellular absorption and/or therapeutic efficacy of a composition for delivery, in addition to the shape of the nanoparticle and/or the chemical property of its surface.

For example, the mesoporous silica nanoparticle may have a controllable pore, a controllable particle size, a large surface area, a large pore volume, a surface that can be easily functionalized, or little or no cytotoxicity leading to high biocompatibility, but it may not be limited thereto.

For example, the mesoporous silica nanoparticle may be applied to a controlled release system having a gate opening and closing system responding to a stimulus, but it may not be limited thereto. For example, the mesoporous silica nanoparticle may have an opening and closing gate in the pore, and since the opening and closing of the gate is controlled by an external stimulus, the gate can control the dissolution timing or amount, etc., of the drug included on the pore, but it may not be limited thereto.

For example, the mesoporous silica nanoparticle may have its pores blocked from the outside by a paraffin cap, etc., and the pores may be exposed when the paraffin cap gets melted above the melting temperature of paraffin, but it may not be limited thereto. Alternatively, for example, the mesoporous silica nanoparticle may have polymers bound around the pore so that substances inside the pore such as a drug, etc., are not normally leaked to the outside, but the pore may be exposed when the polymer gets truncated under a stimulus such as an enzyme, but it may not be limited thereto.

For example, the functional protein or protein drug may be included in the pore of the mesoporous silica nanoparticle, but it may not be limited thereto. By being included in the pore of the mesoporous silica nanoparticle, the protein may be protected from an external protease or internal and external environments around the cells including a serum protein, but it may not be limited thereto. Such protection from an external decomposing enzyme is one of the key factors having clinical significance as a drug delivery system or a functional polymer delivery carrier. In addition, it is advantageous in terms of easy and economical preparation since there is no need to protect a protein from internal and external environments around the cells including the various proteases or the serum protein by chemically modify the protein with the locked nucleic acid (LNA), O-methylation, or phosphorothioate nucleic acid, which is laborious, costly and time wasting.

For example, the mesoporous silica nanoparticle may include a fluorescent dye for its location tracking, but it may not be limited thereto. For example, the mesoporous silica nanoparticle may include a fluorescent dye at its surface, but it may not be limited thereto.

For example, the process of adsorbing or loading a protein to the mesoporous silica nanoparticle may include simply mixing the mesoporous silica nanoparticle with the protein in a solution to adsorb or load the protein thereto, but it may not be limited thereto. For example, the process of adsorbing or loading a protein to the mesoporous silica nanoparticle may include mixing a surface-modified mesoporous silica nanoparticle with the protein in a solution containing PBS (phosphate buffered saline), and incubating them, but it may not be limited thereto. Since such processes do not require chemical bonding, crosslinking, or complicated purification isolation steps, it is simple and economical, and may be carried out in an effective module fashion.

For example, the mesoporous silica nanoparticle may be a nontoxic and bio-friendly, but it may not be limited thereto. Additionally, the mesoporous silica nanoparticle may not require additional surface treatment for increasing the drug delivery efficiency and/or the introduction into cells, but it may not be limited thereto.

According to one embodiment of the present invention, a positive charge or a negative charge is formed on the surface or inside the pore of the mesoporous silica nanoparticle, and the protein may be adsorbed or loaded within the pore by an electrostatic interaction with the positive charge or negative charge, but it may not be limited thereto.

According to one embodiment of the present invention, the antibody, ligand, cell-permeable peptide or aptamer may be any peptide promoting the introduction of an external substance into a cell through a cell membrane, but it may not be limited thereto. The cell-permeable peptide may promote the introduction of an external substance into a cell by itself, or with the assistance of other substances, such as, for example, a protein, but it may not be limited thereto.

For example, the cell-permeable peptide may promote the introduction of an external substance into a cell with the assistance of a protein existing in the cell membrane, but it may not be limited thereto. The cell membrane prevents external substances from entering into the cells. However, in order for a drug or reporter molecules to exhibit intracellular activities, they need to be effectively introduced into the cells. Therefore, binding a cationic peptide as a short strand molecule to a drug delivery carrier may be used for delivering a drug such as a small molecule, a nucleic acid, an antibody, and/or a nanoparticle, etc. into a cell.

Although the mechanism of introducing a cell-permeable peptide into cells has not been clearly clarified, it is known that cell penetration is carried out by various mechanisms. For example, the mechanism includes energy dependent endocytosis and energy independent direct translocation. The cell-permeable peptide which may be used in the present invention may introduce the mesoporous silica nanoparticle into a cell by either of the two mechanisms, but it may not be limited thereto.

For example, the types of peptides which may be used as the cell-permeable peptide are listed in Tables 1 and 2, but it may not be limited thereto.

TABLE 1

| Amino acid sequences | Name | Target tissue |
|---|---|---|
| GRKKRRQRRRPPQ (SEQ ID NO: 1) (13) | TAT | All cells |
| LLIILRRRIRKQAHAHSK (SEQ ID NO: 2) (18) | pVEC | All cells |
| CTPSPFSHC (SEQ ID NO: 3) (9) | TCP-1 | Colorectal cancer cells |
| SFHQFARATLAS (SEQ ID NO: 4) (12) | HAP-1 | Synovial cells |
| HIQLSPFQSWR (SEQ ID NO: 5) (11) | HAP-2 | Synovial cells |

TABLE 1-continued

| Amino acid sequences | Name | Target tissue |
| --- | --- | --- |
| LKKP (SEQ ID NO: 6) (4) | | Myeloid leukemia cells |
| EPKK* (SEQ ID NO: 7) (4) | | Embryonic stem cells |
| ELK*K* (SEQ ID NO: 8) (4) | | Primary monocytes |
| PYEE (SEQ ID NO: 9) (4) | | Amelanotic melanoma cells, ARN8 |
| HMGN2 (High Mobility Group Nucleosomal Binding Domain 2)-N F3 (31) | F3 | Lymphatic endothelial cells, HL-60 and MDA-MB-435 |
| PFSSTKT (SEQ ID NO: 19) (7) | BMHP1 | Neuronal stem cells |
| CTVALPGGYVRVC (SEQ ID NO: 20) (13) | Pep42 | Melanoma cells |
| DWRVIIPPRPSA (SEQ ID NO: 21) (12) | CAP | Chondrocyte cells |
| CDCRGDCFC (SEQ ID NO: 22) (9) | RGD-4C | Angiogenic blood vasculature |
| CRGDK/RGPD/EC (SEQ ID NO: 23) (11) | iRGD | Various tumor cells |
| cRGDf(NMeV) (SEQ ID NO: 24) (5) | cRGD | Angiogenic blood vessels |
| NGR (3) | NGR | Angiogenic blood vessels |

TABLE 2

| Amino acid sequences | Name |
| --- | --- |
| RKKRRQRRR (SEQ ID NO: 13) | $Tat_{49-57}$ |
| RRRRRRRRR (SEQ ID NO: 14) (R9) | Polyarginines |
| RRRRRRRRRFF (SEQ ID NO: 25) | $R_9F_2$ |
| KKKKKKKKKK (SEQ ID NO: 26) (K10) | Decalysine |
| RQIKIWFQNRRMKWKK (SEQ ID NO: 27) | Penetratin |
| GWTLNSAGYLLGKINLKALAALAKKIL (SEQ ID NO: 28) | Transportan |
| YARAAARQARA (SEQ ID NO: 29) | HIV-Tat derived PTD4 |
| PLSSIFSRIGDP (SEQ ID NO: 30) | Hepatitis B Virus Translocation Motif (TLM) |
| MANLGYWLLALFVTMWTDVGLCKKRPKP (SEQ ID NO: 31) | $mPrP_{1-28}$ |
| GGG(ARKKAAKA)4 (SEQ ID NO: 32) | POD |
| MVRRFLVTLRIRRACGPPRVRV (SEQ ID NO: 33) | $ARF_{(1-22)}$ |
| LIRLWSHLIHIWFQNRRLKWKKK (SEQ ID NO: 34) | EB1 |
| TPWWRLWTKWHHKRRDLPRKPE (SEQ ID NO: 35) | Rath |
| GLWRALWRLLRSLWRLLWRA (SEQ ID NO: 36) | CADY |
| DSHAKRHHGYKRKFHEKHHSHRGY (SEQ ID NO: 10) | Histatin 5 |
| ac-GALFLGFLGAAGSTMGAWSQPKKKRKV (SEQ ID NO: 11)-cya | MPG |

TABLE 2-continued

| Amino acid sequences | Name |
|---|---|
| ac-GALFLGFLGAAGSTMGAWSQPKSKRKV (SEQ ID NO: 37)-cya | MPG$^{(\Delta NLs)}$ |
| ac-GALFLGFLGAAGSTMGAWSQPKSKRKV (SEQ ID NO: 38)-cya | Pα |
| ac-KETWWETWWTEWSQPKKKRKV (SEQ ID NO: 39)-cya | Pep-1 |
| ac-KETWFETWFTEWSQPKKKRKV (SEQ ID NO: 40)-cya | Pep-2 |
| ac-KETWFETWFTEWSQPKKKRKV (SEQ ID NO: 41)-cya | Pep-3 |

The amino acid sequences of the cell-permeable peptides listed above may be partially modified as far as the activity of the cell-permeable peptides are maintained, but it may not be limited thereto.

For example, the cell-permeable peptide may include MPAP, TAT, or polyarginine, but it may not be limited thereto. For example, the MPAP may have the amino acid sequence of myristic acid-ARRRRRRRC (SEQ ID NO: 12); the TAT may have the amino acid sequence of RKKRRQRRR (SEQ ID NO: 13); and the poly-arginine may have the amino acid sequence of RRRRRRRRR (SEQ ID NO: 14) (9 arginines), but it may not be limited thereto.

Figure 2:
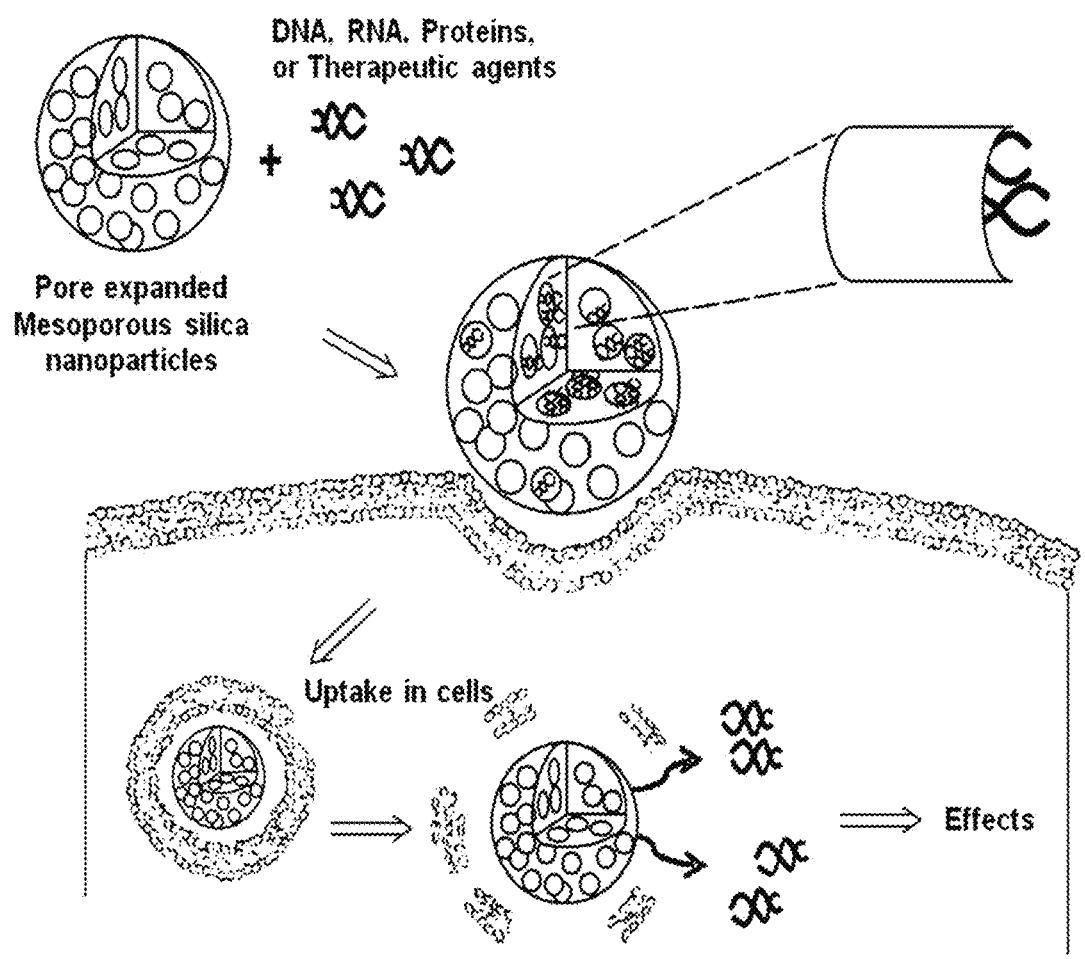
FIG. 2 is a schematic figure showing a composition for delivering a protein according to one embodiment of the present invention and its intracellular action.

FIG. 2 is a schematic figure of a composition for delivering a protein according to one embodiment of the present invention.

As shown in FIG. 2, in one embodiment of the present invention, the mesoporous silica nanoparticle may be subjected to endocytosis of a cell owing to its small size and particle property, and thus can be introduced into the cell along with the protein drug adsorbed or loaded.

In one embodiment of the present invention, the mesoporous silica nanoparticle may be functionalized by amine, carboxyl group, phosphatidyl ethylamine, or polyethylene glycol (PEG), but it may not be limited thereto. Polyethylene glycol may be bound to the surface of the mesoporous silica nanoparticle by the phosphatidyl ethylamine, or polyethylene glycol, but it may not be limited thereto. By the phosphatidyl ethylamine, or polyethylene glycol, the aggregation of the mesoporous silica nanoparticles may be prevented, the non-specific binding with other biomolecules may be minimized, or the RNA adsorbing or loading outside the pore may be reduced, but it may not be limited thereto.

In one embodiment of the present invention, the size of the mesoporous silica nanoparticle may range from about 0.1 μm to about 100 μm in average, but it may not be limited thereto.

In one embodiment of the present invention, the size of the pore of the mesoporous silica nanoparticle may range from about 1 nm to about 100 nm in average, but it may not be limited thereto. For example, the size of the pore of the mesoporous silica nanoparticle may be, in average, about 1 nm to about 100 nm, about 10 nm to about 100 nm, about 20 nm to about 100 nm, about 30 nm to about 100 nm, about 40 nm to about 100 nm, about 50 nm to about 100 nm, about 60 nm to about 100 nm, about 70 nm to about 100 nm, about 80 nm to about 100 nm, about 90 nm to about 100 nm, 1 nm to about 90 nm, about 10 nm to about 90 nm, or about 20 nm to about 90 nm, about 30 nm to about 90 nm, about 40 nm to about 90 nm, or about 50 nm to about 90 nm, from about 60 to about 90 nm, about 70 nm to about 90 nm, or about 80 nm to about 90 nm, about 1 nm to about 80 nm, about 10 nm to about 80 nm, or about 20 nm to about 80 nm, about 30 nm to about 80 nm, about 40 nm to about 80 nm, or about 50 nm to about 80 nm, about 60 nm to about 80 nm, about 70 nm to about 80 nm, or from about 1 nm to about 70 nm, about 10 nm to about 70 nm, about 20 nm to about 70 nm, or about 30 nm to about 70 nm, about 40 nm to about 70 nm, about 50 nm to about 70 nm, or about 60 nm to about 70 nm, about 1 nm to about 60 nm, about 10 nm to about 60 nm, or about 20 nm to about 60 nm, about 30 nm to about 60 nm, about 40 nm to about 60 nm, or about 50 nm to about 60 nm, about 1 nm to about 50 nm, about 20 nm to about 50 nm, or about 30 nm to about 50 nm, about 40 nm to about 50 nm, about 1 nm to about 40 nm, or about 10 nm to about 40 nm, about 20 nm to about 40 nm, about 30 nm to about 40 nm, or from about 1 nm to about 30 nm, about 10 nm to about 30 nm, about 20 nm to about 30 nm, or from about 1 nm to about 20 nm, about 10 nm to about 20 nm, about 1 nm to about 10 nm, but it may not be limited thereto.

A conventional mesoporous silica nanoparticle contains pores with an average pore diameter of only a few nm, and thus has a disadvantage that a biopolymer such as a protein cannot sufficiently enter into the pore. However, because a mesoporous silica nanoparticle according to one embodiment of the present invention has pores with an expanded average pore diameter compared to a conventional mesoporous silica nanoparticle for delivering a drug, a bioactive material or a protein can be more easily included inside of the pore. In addition, a mesoporous silica nanoparticle according to one embodiment of the present invention not only has pores with an expanded size, but also has expanded pores formed in the entire outer and inner surfaces of the particle and even in the deep inside of the particle, and thus a bioactive material or a protein can be more easily included in the pore at the outer and inner surface of the particle.

In one embodiment of the present invention, the mesoporous silica nanoparticle may be prepared by a method including the steps of: forming a mesoporous silica nanoparticle; and expanding the pore of the mesoporous silica nanoparticle, but it may not be limited thereto.

For example, the step of forming a mesoporous silica nanoparticle may include forming the mesoporous silica nanoparticle from a silica precursor, but it may not be limited thereto. For example, the formation of the mesoporous silica nanoparticle from the silica precursor may further include mixing the silica precursor with a solution containing a surfactant, but it may not be limited thereto. For example, the solution containing a surfactant may be a solution further including alcohol, water, and sodium hydroxide, but it may not be limited thereto. For example, the surfactant may be CTAB (cetyltrimethylammonium bromide), TMABr (hexadecyltrimethylammonium bromide), TMPrCl (hexadecyltrimethylpyridinium chloride), or TMACl (tetramethylammonium chloride), but it may not be limited thereto.

For example, the step of expanding the pore of the mesoporous silica nanoparticle may be conducted using an expanding agent, but it may not be limited thereto. For example, the expanding agent may include, for example, trimethylbenzene (TMB), or N,N-dimethylhexadecylamine (DMHA), but it may not be limited thereto.

The mesoporous silica nanoparticle may be one which may be produced by a simple method for easy mass production, but it may not be limited thereto. For example when laboratory equipment is used, the mesoporous silica nanoparticle may be produced in an amount of at least about 1 g or more in one cycle of the synthesis procedure by using the above method, but it may not be limited thereto.

In one embodiment of the present invention, the step of expanding the pore of the mesoporous silica nanoparticle may include expanding the pore by treating the mesoporous silica nanoparticle with tri($C_{1-6}$ alkyl)benzene, but it may not be limited thereto. For example, tri($C_{1-6}$ alkyl)benzene may include trimethylbenzene, triethylbenzene, tripropylbenzene, tributylbenzene, tripentylbenzene, or trihexylbenzene, but it may not be limited thereto. For example, the step of expanding the pore by treating the mesoporous silica nanoparticle with tri($C_{1-6}$ alkyl)benzene may include autoclaving a mixture containing the mesoporous silica nanoparticle and tri($C_{1-6}$ alkyl)benzene at the temperature of about 80° C. to about 200° C., but it may not be limited thereto. For example, the step of expanding the pore by treating the mesoporous silica nanoparticle with tri($C_{1-6}$ alkyl)benzene may include autoclaving a mixture containing mesoporous silica nanoparticle and tri($C_{1-6}$ alkyl)benzene at the temperature of about 80° C. to about 200° C., about 80° C. to about 160° C., about 80° C. to about 120° C., about 120° C. to about 200° C., about 160° C. to about 200° C., or about 120° C. to about 160° C., but it may not be limited thereto.

For example, the pore having a size of less than about 5 nm may be expanded to the pore having a size of about 5 nm to about 100 nm, or about 10 nm to about 100 nm, by the above step of expanding the pore, but it may not be limited thereto.

In one embodiment of the present invention, the composition for delivering a bioactive material or protein may be applied to, but not limited to, drugs for intravascular injection, drugs for oral administration, drugs for transdermal administration or patches, drugs for topical administration, cosmetics, ointments, food, drinks, shampoo, detergents, leukemia, dialysis, blood transplantation, vascular grafts, dental implants, implant placement, angioplasty, hair transplantation, organ transplantation, tissue transplantation, bone transplantation, nuclear transplantation, cell transplantation, germ cell transplantation, embryo transplantation, animal cloning, production of transformed embryos, production of transformed animals, stem cell production, quality improved plant production, interspecies nuclear transplantation, interspecies organ transplantation, production of pluripotent stem cells, for example, embryonic technology (microinjection, parthenogenesis, zygogenesis, nuclear deliver, blastomere deliver, blastomere fusion, IVF, ICSI, etc.), cell differentiation induction technology, stem cell therapeutics, cell therapeutics, hormones, antibody therapeutics, capsules, syrups, reagents for research, pollutants purification, chemical and biological weapons, diet products, plastic surgery (cranio-maxillo-facial plastic surgery, orthognathic plastic surgery, breast plastic surgery), or the like.

In one embodiment of the present invention, the composition for delivering a bioactive material or a protein may be applied to, but not limited to, autoimmune diseases (atopy, skin pruritus, asthma, rheumatoid arthritis), solid tumor, blood cancer, brain diseases, cardiovascular diseases, circulatory diseases, respiratory system diseases, digestive diseases (gastrointestinal diseases, reflux esophagitis, peptic ulcer, gastric ulcer, inflammatory diseases, neurological diseases of brain, chronic and acute diseases, senile diseases, incurable diseases, periodontal diseases, oral diseases, craniofacial diseases, ischemic diseases, liver diseases, pulmonary diseases, skin diseases, bacterial diseases, viral diseases, infectious diseases, bone diseases (osteoporosis, fracture, etc.), arthritic diseases, spinal diseases, allergic diseases, environmental diseases, drinking diseases, metabolic diseases, hypersensitivity diseases, kidney diseases, thyroid diseases, reproductive diseases, neoplastic diseases, autoimmune diseases, GERD, ulcer, autoimmune conditions, diabetes, genetic conditions, viral/bacterial/parasitic infections, worm conditions, physical conditions, prion diseases, nutritional deficiencies, vitamin/mineral deficiencies, mitochondrial diseases, accidents, sexually transmitted diseases, pregnancy conditions, breast feeding conditions, birth defects, male/female/infant/childhood/adolescent conditions, immune diseases, balance diseases, pain, systemic diseases, blood conditions, blood vessel conditions, nerve conditions, muscle conditions, heart conditions, back neck/spinal cord conditions, eye conditions, brain conditions, mental conditions, nose conditions, mouth conditions, dental conditions, foot/leg/knee conditions, upper limb condition, shoulder conditions, ear conditions, lung conditions, liver conditions, kidney conditions, gall bladder conditions, pancreas conditions, digestive conditions, prostate conditions, male genital conditions, obstetrical conditions, gynecological conditions, thyroid diseases, hearing diseases, aesthetic invention, pigmentation, hair loss, hair growth, hair removal, etc.

In another aspect of the present invention, there is provided a method for delivering a protein including the following:

introducing a composition for delivering a protein into a target cell, the composition including a mesoporous silica nanoparticle having pores with an average pore diameter of about 1 nm or more to about 100 nm or less; a functional group which binds to an inner or outer surface of the pore of the mesoporous silica nanoparticle and gives a surface negative charge or positive charge, or a ligand which binds to an inner or outer surface of the pore of the mesoporous silica nanoparticle and specifically binds to a protein; and a protein which is adsorbed or loaded within the pore of the mesoporous silica nanoparticle.

In one embodiment of the present invention, the size of the mesoporous silica nanoparticle may range from about 0.1 μm to about 100 μm in average, but it may not be limited thereto.

In one embodiment of the present invention, the size of the pore of the mesoporous silica nanoparticle may range from about 1 nm to about 100 nm in average, but it may not be limited thereto. For example, the size of the pore of the mesoporous silica nanoparticle may be, in average, about 1 nm to about 100 nm, about 10 nm to about 100 nm, about 20 nm to about 100 nm, about 30 nm to about 100 nm, about 40 nm to about 100 nm, about 50 nm to about 100 nm, about 60 nm to about 100 nm, about 70 nm to about 100 nm, about 80 nm to about 100 nm, about 90 nm to about 100 nm, about 1 nm to about 90 nm, about 10 nm to about 90 nm, or about 20 nm to about 90 nm, about 30 nm to about 90 nm, about 40 nm to about 90 nm, or about 50 nm to about 90 nm, nm from about 60 to about 90 nm, about 70 nm to about 90 nm, or about 80 nm to about 90 nm, about 1 nm to about 80 nm, about 10 nm to about 80 nm, or about 20 nm to about 80 nm, about 30 nm to about 80 nm, about 40 nm to about 80 nm, or about 50 nm to about 80 nm, about 60 nm to about 80 nm, about 70 nm to about 80 nm, or from about 1 nm to about 70 nm, about 10 nm to about 70 nm, about 20 nm to about 70 nm, or about 30 nm to about 70 nm, about 40 nm to about 70 nm, about 50 nm to about 70 nm, or about 60 nm to about 70 nm, about 1 nm to about 60 nm, about 10 nm to about 60 nm, or about 20 nm to about 60 nm, about 30 nm to about 60 nm, about 40 nm to about 60 nm, or about 50 nm to about 60 nm, about 1 nm to about 50 nm, about 20 nm to about 50 nm, or about 30 nm to about 50 nm, about 40 nm to about 50 nm, about 1 nm to about 40 nm, or about 10 nm to about 40 nm, about 20 nm to about 40 nm, about 30 nm to about 40 nm, or from about 1 nm to about 30 nm, about 10 nm to about 30 nm, about 20 nm to about 30 nm, or from about 1 nm to about 20 nm, about 10 nm to about 20 nm, about 1 nm to about 10 nm, but it may not be limited thereto.

In one embodiment of the present invention, the protein may be one selected from the group consisting of a protein complex including proteasome, etc.; various enzymes such as caspase, ribonuclease, kinase and phosphatase; and various antibodies, but it may not be limited thereto.

In one embodiment of the present invention, the protein may be selected from the group consisting of a systemic hormone, a cytokine, a regulatory factor associated with a normal healing process such as a growth factor and other proteins that control differentiation and proliferation of a cell, and a growth factor reported to have an ability to heal a wound, a cytokine or a hormone such as transforming growth factor-β superfamily (TGF-β) protein, macrophage-colony forming-stimulating factor (M-CSF), a protein complex such as proteasome, etc.; various enzymes such as caspase, ribonuclease, kinase and phosphatase; and various antibodies, but it may not be limited thereto.

In one embodiment of the present invention, the introduction of the composition for delivering the protein into the target cell may include adding said composition to a cell culture medium and introducing said composition into the target cell, but it may not be limited thereto.

In one embodiment of the present invention, the introduction of the composition for delivering a protein into the target cell may include introducing the composition for delivering the protein into the target cell by intravascular administration, oral administration, transdermal administration, or local administration by injection, but it may not be limited thereto.

In one embodiment of the present invention, the mesoporous silica nanoparticle may further include an antibody, a ligand, a cell-permeable peptide or an aptamer bound to a surface of the mesoporous silica nanoparticle, but it may not be limited thereto.

According to one embodiment of the present invention, the mesoporous silica nanoparticle may be surface-modified with nickel, nickel-NTA, glutathione, dextrin, biotin or streptavidin, but it may not be limited thereto. A tag in the protein may bind to the pore of the mesoporous silica nanoparticle to be efficiently loaded within the pore. For example, in case that the mesoporous silica nanoparticle is surface-modified with nickel or nickel-NTA, the protein may be adsorbed or loaded within the pore by a non-covalent interaction between nickel of the mesoporous silica nanoparticle and His-tag of the protein. For the adsorbing or loading of a protein having GST-tag, mesoporous silica nanoparticle may be surface-modified with glutathione, and for the adsorbing or loading of a protein having biotin-tag, mesoporous silica nanoparticle may be surface-modified with streptavidin, but it may not be limited thereto.

In the mesoporous silica nanoparticle according to one embodiment of the present invention, its surface and/or inside of the pore of the nanoparticle may exhibit a positive charge or negative charge, and thus it is possible to attach the protein exhibiting a positive charge and/or the protein exhibiting a negative charge within the pore of the mesoporous silica nanoparticle. In addition, a mesoporous silica nanoparticle of the present invention has a large average pore diameter, which allows accommodation of a protein with a large size. That is, the protein can be easily introduced into a cell without regard to the surface charge and the size thereof.

In one embodiment of the present invention, the introduction of the composition for delivering a drug including a bioactive material or a protein into a target cell may be carried out by the endocytosis of the cell, but it may not be limited thereto (FIG. 2). For example, the composition for delivering a drug may be introduced into the cytoplasm or nucleus of the cell, but it may not be limited thereto.

For example, the target cell may be a cell derived from prokaryotic or eukaryotic animal cells, such as, for example, a mammalian cell or a human-derived cell, but it may not be limited thereto. For example, the cells may include cancer cells, tissue cells of an organ, cancer cells, bone cells, stomach cells, intestinal cells, lung cells, liver cells, brain cells, blood cells, immune cells, erythrocytes, leukocytes, lymphocytes, or the like, but it may not be limited thereto.

In one embodiment of the present invention, the protein drug may be one selected from the group consisting of a protein complex including proteasome, etc.; various enzymes such as caspase, ribonuclease, kinase and phosphatase, etc.; and various antibodies, but it may not be limited thereto.

In one embodiment of the present invention, the introduction of the composition for delivering the protein into the target cell may include adding said composition to a cell culture medium and introducing said composition into the target cell, but it may not be limited thereto.

In one embodiment of the present invention, the introduction of the composition for delivering the protein into the target cell may include introducing the composition for delivering the protein into the target cell by intravascular administration, oral administration, transdermal administration, or local administration by injection, but it may not be limited thereto.

For example, by the intravascular administration, a protein can be delivered to the entire body through the circulatory system, but it may not be limited thereto. For example, by the oral administration, the protein can be easily delivered mainly to the digestive system, but it may not be limited thereto.

For example, by the transdermal administration, a protein can be delivered through the skin, but it may not be limited thereto. For example, the disease that is the object of the transdermal administration may be atopy, hair loss, pigmentation, skin diseases or the like, but it may not be limited thereto.

For example, the local administration by injection may be applied to the local and topical tissues such as the eye, skin, mucous membrane, or a localized tumor, but it may not be limited thereto. For example, the local administration may show high biological applicability, accessibility to a target tissue, and/or may reduce the side effects commonly associated with systemic application. For example, the disease that is the object of the local administration, may be reduced visual acuity, atopic dermatitis, Huntington's disease, chronic pain, or pleomorphic glioblastosis, or the like, but it may not be limited thereto.

Hereinafter, the present invention is explained in detail by Examples. The following Examples are intended to further illustrate the present invention without limiting its scope.

EXAMPLES

Preparation Example 1: Synthesis of Pore-Expanded Mesoporous Silica Nanoparticle (MSN)

3.94 g of cetyltrimethylammonium bromide (CTAB) and 2.28 mL of 1 M sodium hydroxide (NaOH) solution were dissolved in 800 g of methanol-water mixture solution (methanol:water=0.4:0.6, w/w). Then 1.3 mL of tetramethoxy silane (TMOS) was added to the obtained mixed solution as the solution was vigorously stirred at the ambient condition. The reaction mixture was stirred for 8 hours, and then ripened overnight. The resulting white sediment was purified by centrifugation to remove the surfactant remaining in the solution, and washed with ethanol and water 5 times each. The prepared MSNs were suspended in 20 mL of ethanol, and 4 mL of hydrochloric acid was added thereto. Then the suspension was refluxed overnight to obtain white powders. The white powders were isolated by a filter and washed with ethanol to obtain the MSN having a pore size of 2 nm.

In order to prepare the MSNs with expanded pores, the MSNs thus prepared in the above Preparation Example were dispersed in ethanol by sonication for 30 min, and then water and trimethylbenzene (TMB) (20 mL in total with mixing ratio (v/v) of 1:1) were added thereto. Then the mixture was put in the autoclave and kept at 160° C. for 48 hours. The white powders thus obtained were washed with ethanol and water 5 times each. Then the MSNs were suspended in 2 M ethanolic HCl, and then heated in the autoclave at 120° C. for 20 hours to remove the organic surfactant (CTAB). Then, the mixture obtained was filtered and washed with ethanol and water 10 times each to obtain the pore-expanded MSN (1 of FIGS. 11a and 11b).

Preparation Example 2: Silica Nanoparticle Modified by Ni-NTA (MSNPN)

Figure 10A:
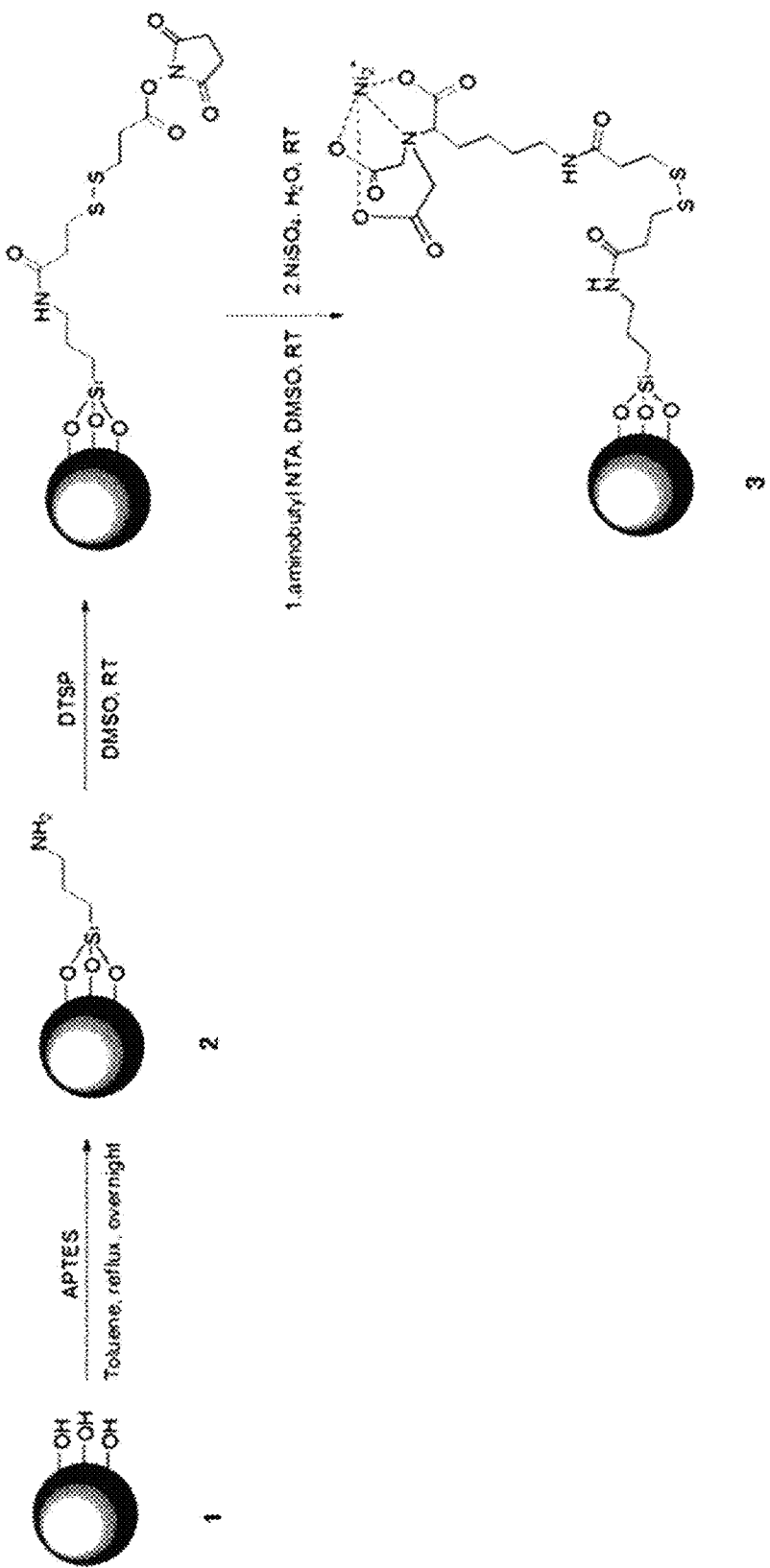
FIGS. 10a and 10b are schematic figures respectively showing mesoporous silica nanoparticle having nickel moiety (MSNPN) synthesis and TAMRA-labeled MSNPN synthesis according to one embodiment of the present invention.
Figure 10B:
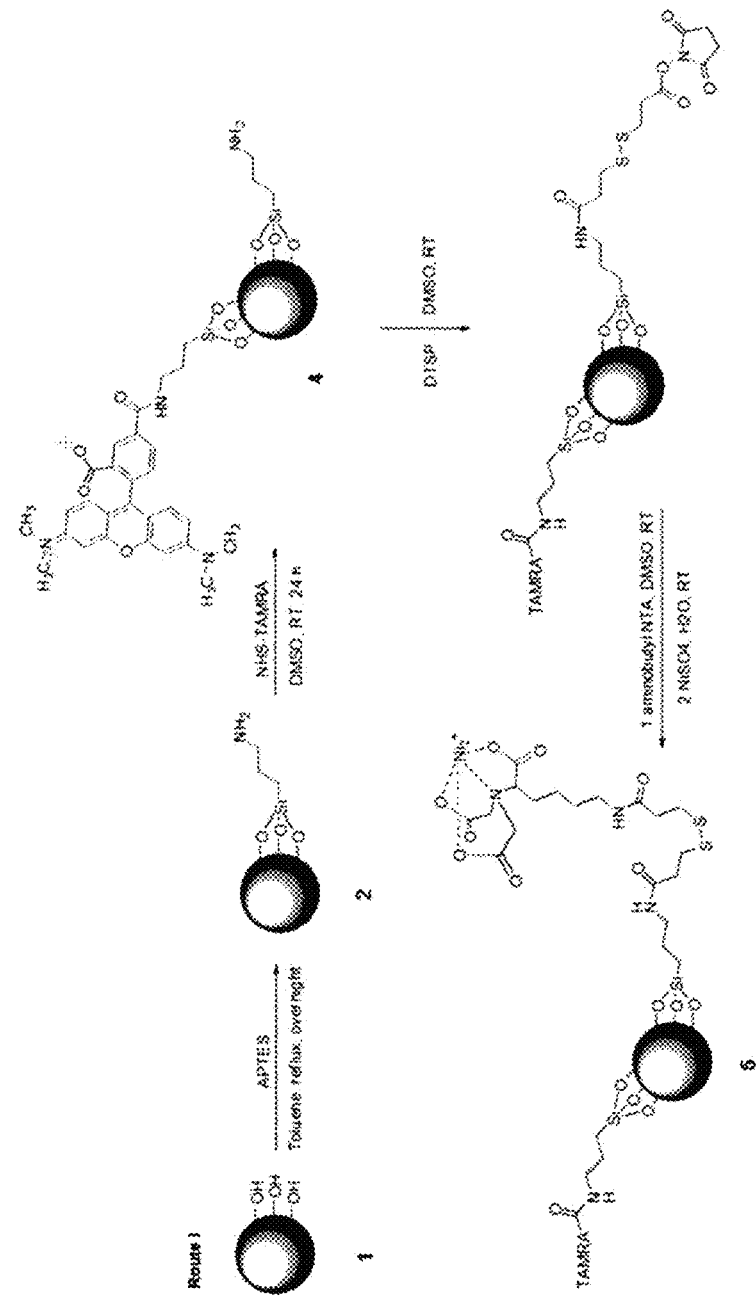

100 mg of the pore-expanded MSN prepared in Preparation Example 1 was suspended in 10 mL of toluene, and 3-aminopropyl triethoxysilane (APTES) was added thereto for amine-functionalization. After overnight refluxing of the suspension, the suspension was filtered by a filter, and then, the remainder was washed 10 times with ethanol to obtain the amine-functionalized MSN (2 of FIG. 10a and FIG. 10b). 30 mg of the amine-functionalized MSN was reacted overnight at room temperature (RT) with 100 mg of [3,3'-dithiodipropionic acid di (N-hydroxysuccinimide ester), DTSP] in DMSO. The reaction mixture was washed 3 times with DMSO, and added with 10 mL of $N_\alpha,N_\alpha$-bis (carboxymethyl)-L-lysine hydrate (aminobutyl NTA, 65 mg) in DMSO. The above reaction was conducted at RT for 24 hours. Then the reaction mixture was washed with ethanol and water 10 times each, to obtain the NTA-modified MSN. In order to integrate $Ni^{2+}$ into the NTA-modified MSN, the nanoparticles were dispersed in 1 M aqueous $NiSO_4$, stirred at RT for 24 hours, and then washed with ethanol and water 5 times each. The resulting powders (MSNPN) thus obtained (3 of FIG. 10a) was dried in vacuum and dispersed in water without nuclease. The suspension was stored at 4° C. until the suspension was used.

Preparation Example 3: Fluorescent Material-Bound Silica Nanoparticles 30 mg of the amine-functionalized MSN prepared in Preparation Example 2 (2 of FIGS. 10a and 10b) was suspended in 1 mL of DMSO, and the suspension was added with 10 μL of carboxytetramethylrhodamine (TAMRA-NHS) which is activated by N-hydroxysuccinimide (NHS) ester contained in DMSO in a concentration of 2.5 mg/mL. The solution was stirred at RT for 3 hours, and centrifuged to obtain TAMRA-bound MSN in the form of powders (4 of FIG. 10b). Ni-NTA was introduced into the TAMRA-bound MSN by the same process as Preparation Example 2, to obtain the TAMRA-bound MSNPN (5 of FIG. 10b).

Example 1: Analysis of Surface Properties of Pore-Expanded MSN

In order to analyze the physical properties of MSN such as surface area, pore size and pore volume, the nitrogen adsorbing or loading experiment was conducted. The nitrogen adsorbing or loading isotherm line was measured by NOVA adsorption equipment.

The surface area was calculated by Brunauer-Emmett-Teller (BET) method, and the distribution of pore size was calculated by Barrett-Joyner-Halenda (BJH) method. The results are shown in Table 3 below.

TABLE 3

| | Mean pore size (nm) | BET surface area ($m^2$/g) | Pore volume (mL/g) |
|---|---|---|---|
| MSNPN | 28 ± 2 | 388 | 1.47 |

Figure 11:
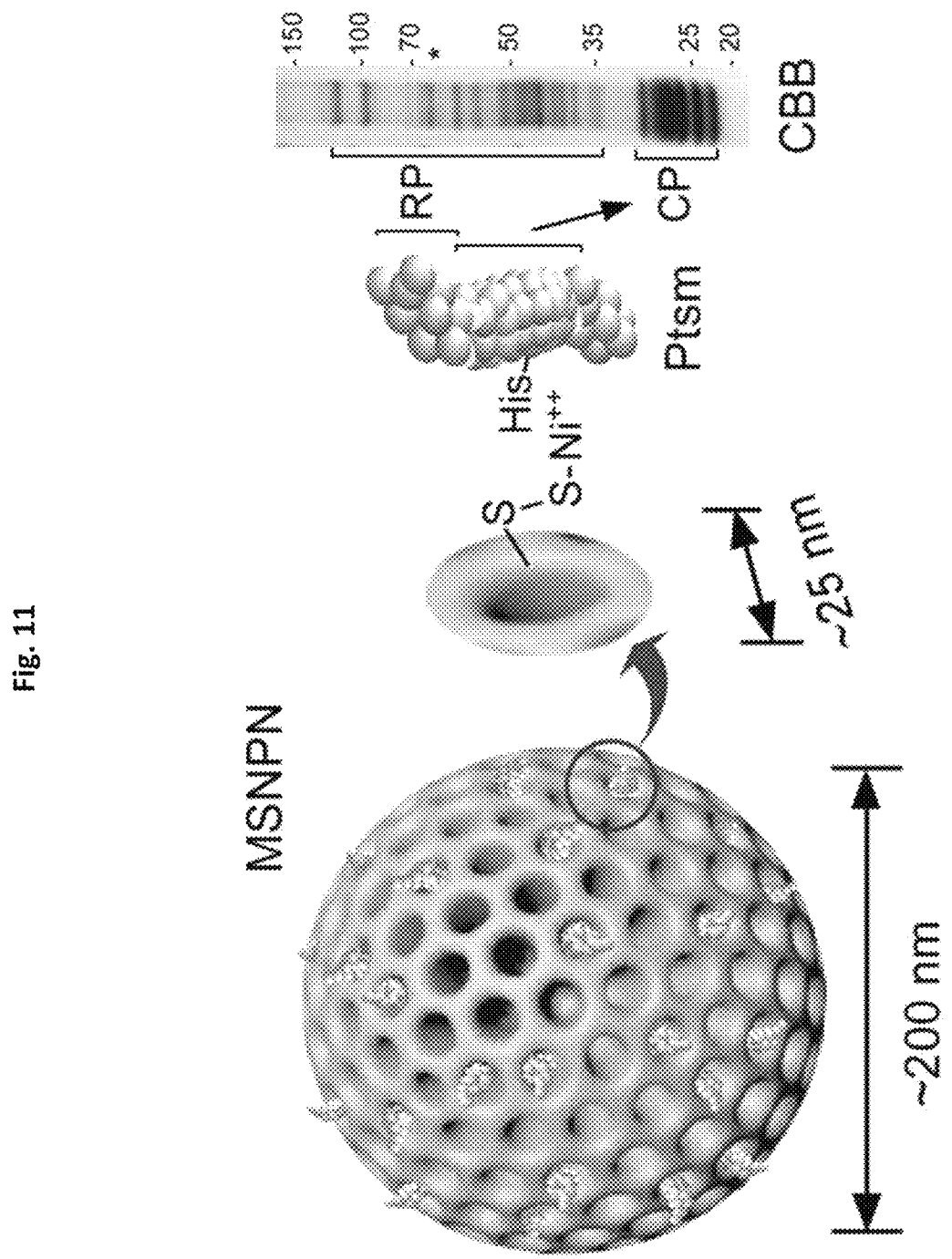
FIG. 11 shows the interaction and SDS-PAGE image of proteasome-MSNPN according to one embodiment of the present invention.

The novel mesoporous silica nanoparticle having nickel moiety (MSNPN) was synthesized to have a pore size of 25 nm to 30 nm by the pore expansion strategy, which can hide the complete-enzyme molecules of proteasome by the non-covalent interaction with His tag of proteasome (FIG. 11). The relatively large surface area (388 $m^2$/g) and pore volume (1.47 mL/g) of MSNPN is advantageous in adsorbing or loading and delivering proteasome in the original form.

Preparation Example 4: MSN with Surface Exhibiting Anions

The pore-expanded MSNs prepared in Preparation Example 1 were washed several times with ethanol and water to obtain the MSN with the surface exhibiting anions.

Preparation Example 5: MSN with Surface Exhibiting Cations

The pore-expanded MSNs prepared in Preparation Example 1 were suspended in toluene, and 1 mL of 3-aminopropyl triethoxysilane (APTES) was added thereto for amine-functionalization. After washing, the MSNs with the surface exhibiting cations were obtained.

Figure 3:
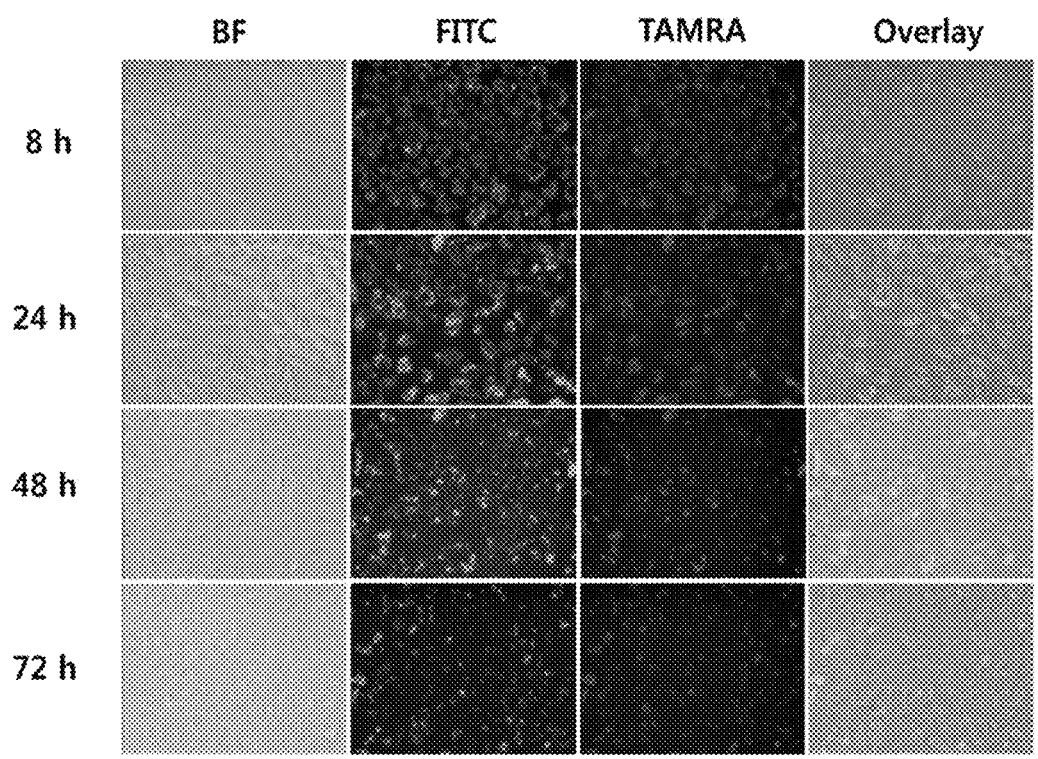
FIG. 3 is fluorescence microscopic images of the cells into which mesoporous silica nanoparticles including proteins according to one embodiment of the present invention were introduced.

Example 2: Experiment on Introduction of MSN Containing Protein within its Pore into Cells In this Example, proteins were adsorbed or loaded within the pores of the MSNs with the surface exhibiting anions and/or the surface exhibiting cations, and the MSNs were introduced into cells to introduce the proteins into the cells. Specifically, fluorescence (FITC)-labeled bovine serum albumin (BSA) and MSN were mixed at the weight ratio of 1:10 under the condition of 1×PBS, and then, the mixture was incubated at RT for 30 min. Then the mixture was mixed and treated with the cell culture media to introduce the MSN adsorbed or loaded with proteins into the cells. After observation with the treatment time being varied, the cell media for the cells in which treatment was completed were replaced with new media. FIG. 3 shows fluorescence microscopic images of the cells treated with the MSN containing fluorescence-labeled BSA, in the order of the treatment time.

Figure 4:
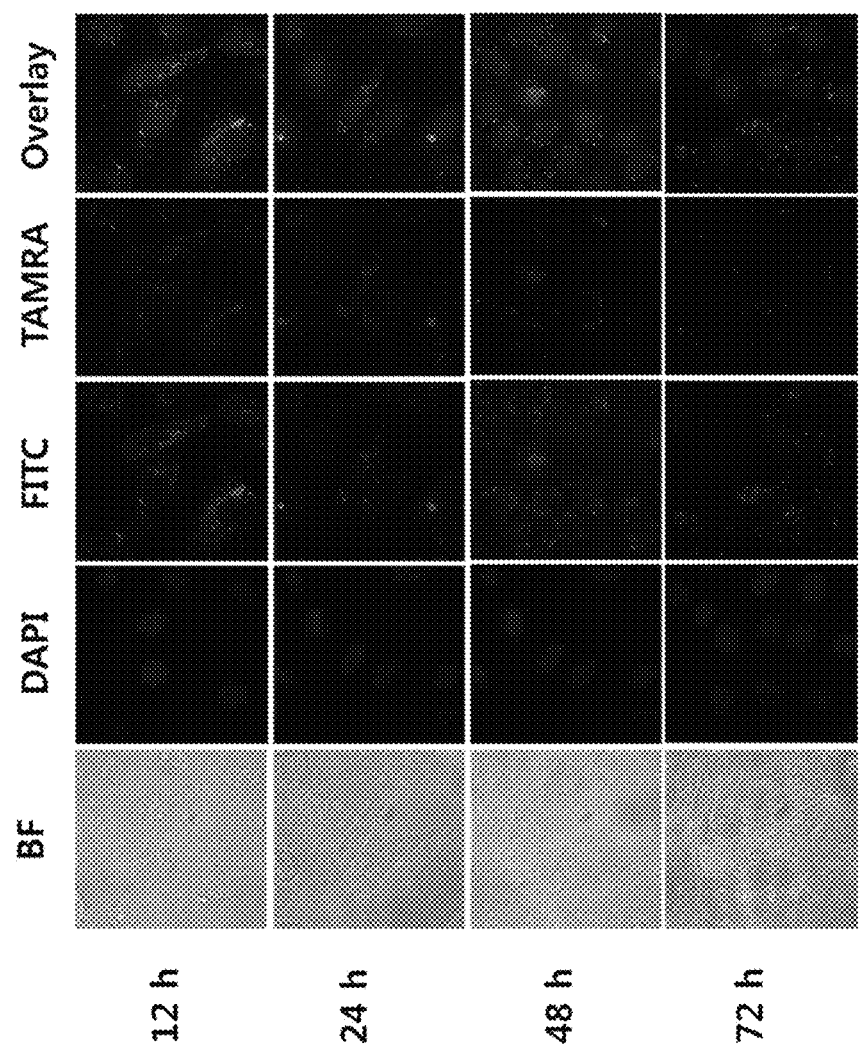
FIG. 4 is fluorescence microscopic images of the cells into which mesoporous silica nanoparticles including proteins according to one embodiment of the present invention were introduced.

Next, by the same method, the fluorescence-labeled IgG proteins were adsorbed or loaded within the pores of the MSN, which were introduced into cells. FIG. 4 shows the fluorescence microscopic images of the introduced cells.

FIG. 3 and FIG. 4 show that the fluorescence-labeled BSA and IgG were efficiently introduced into the cells.

Example 3: Introduction of β-Galactosidase into Cells and Analysis of the Effect of Protease In this Example, β-galactosidase (pI=4.88) was adsorbed or loaded within the pore of MSN with the surface exhibiting cations to introduce it into cells, and then the efficiency of introduction into the cells and effect of the protease were analyzed.

First, by the same method in Example 2, the β-galactosidase in various concentrations were adsorbed or loaded to MSN, which were used for treating cells for 4 hours, and then the culture media were replaced with new media. After incubation for 4 hours, the cells were fixed and treated with X-gal and observed by a microscope.

Figure 5:
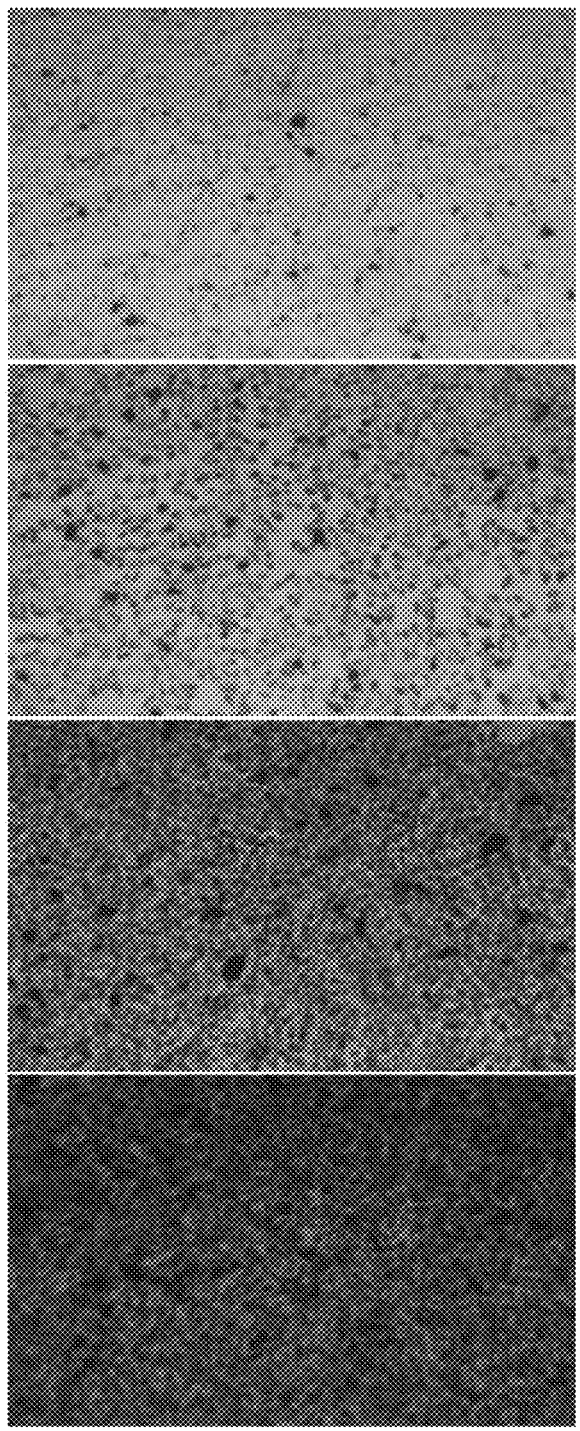
FIG. 5 is stained images of the cells into which mesoporous silica nanoparticles including proteins according to one embodiment of the present invention were introduced.
Figure 6:
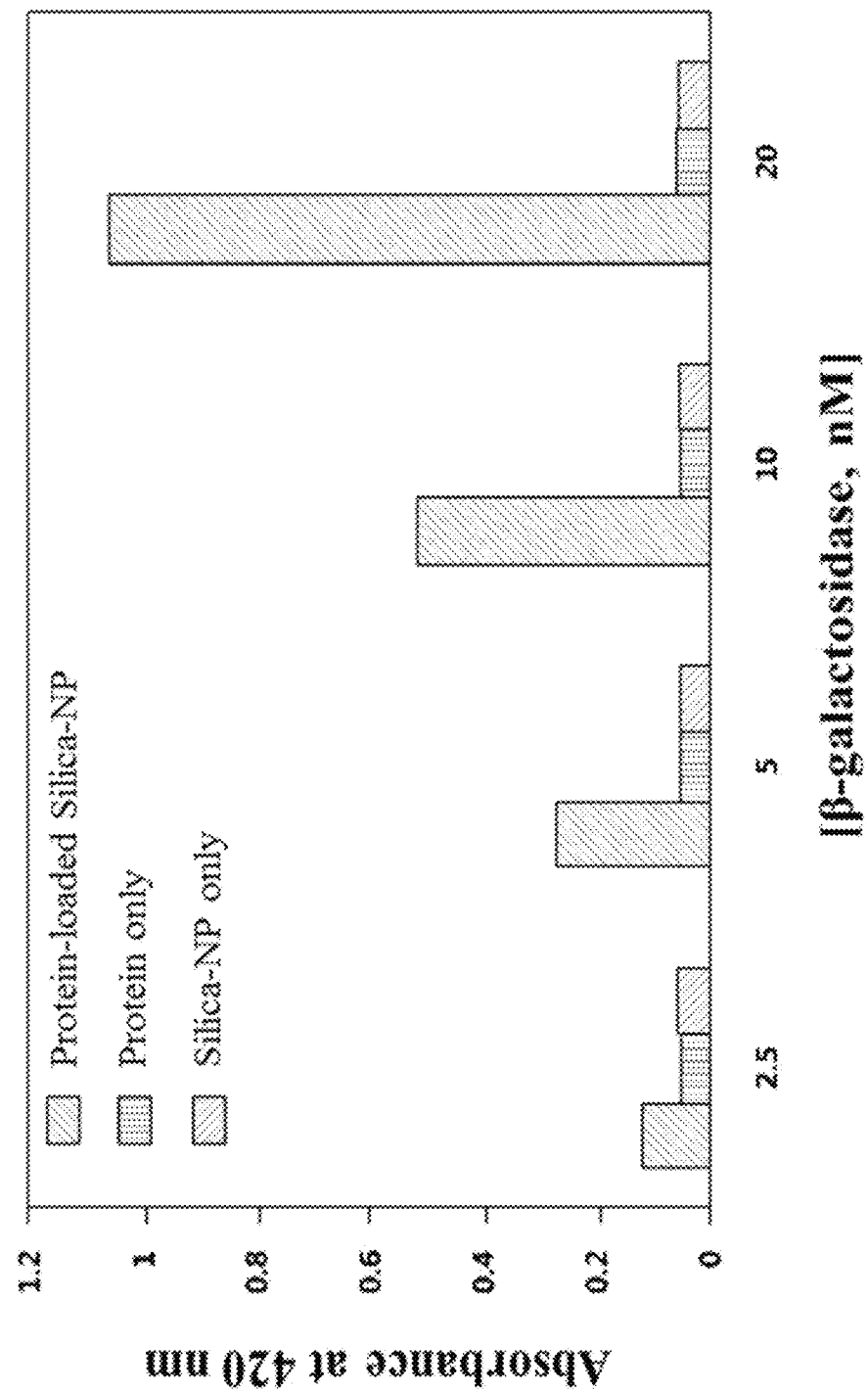
FIG. 6 is a graph showing the ONPG analysis of the cells into which mesoporous silica nanoparticles including proteins according to one embodiment of the present invention were introduced.

FIG. 5 shows the microscopic images of the cells stained with X-gal, which are images of the cells into which the MSNs adsorbed or loaded with β-galactosidase were introduced, shown in the order of β-galactosidase concentrations: 2.5 nM, 5 nM, 10 nM and 20 nM, from the top to the bottom. As shown in FIG. 6, the efficiency of X-gal staining increased depending on the concentration of β-galactosidase, which allowed us to confirm that the β-galactosidase adsorbed or loaded to the MSN was normally introduced into the cells.

Next, the cells were respectively treated with β-galactosidase, MSN, and MSN adsorbed or loaded with β-galactosidase for 4 hours, and the cell culture media were replaced with new media, and then, the cells were incubated for 4 hours. Then the cells were treated with o-nitrophenyl-a-D-galactopyranoside (ONPG), and the absorbance of each of them was measured and shown in the graph (FIG. 6). As shown in FIG. 6, upon ONPG analysis, the absorbance was not detected in the cells treated with β-galactosidase alone or MSN alone, but in the cells treated with the MSN to which β-galactosidase was adsorbed or loaded, the absorbance of nitrophenol produced by β-galactosidase was observed. Also, the absorbance increased depending on the concentration of β-galactosidase. Accordingly, it was found that the MSN adsorbed or loaded with β-galactosidase was normally introduced into the cells, β-galactosidase alone cannot be introduced into the cells, and the absorbance observed was produced by the β-galactosidase within the pore of the MSN which was introduced into the cells.

Figure 7:
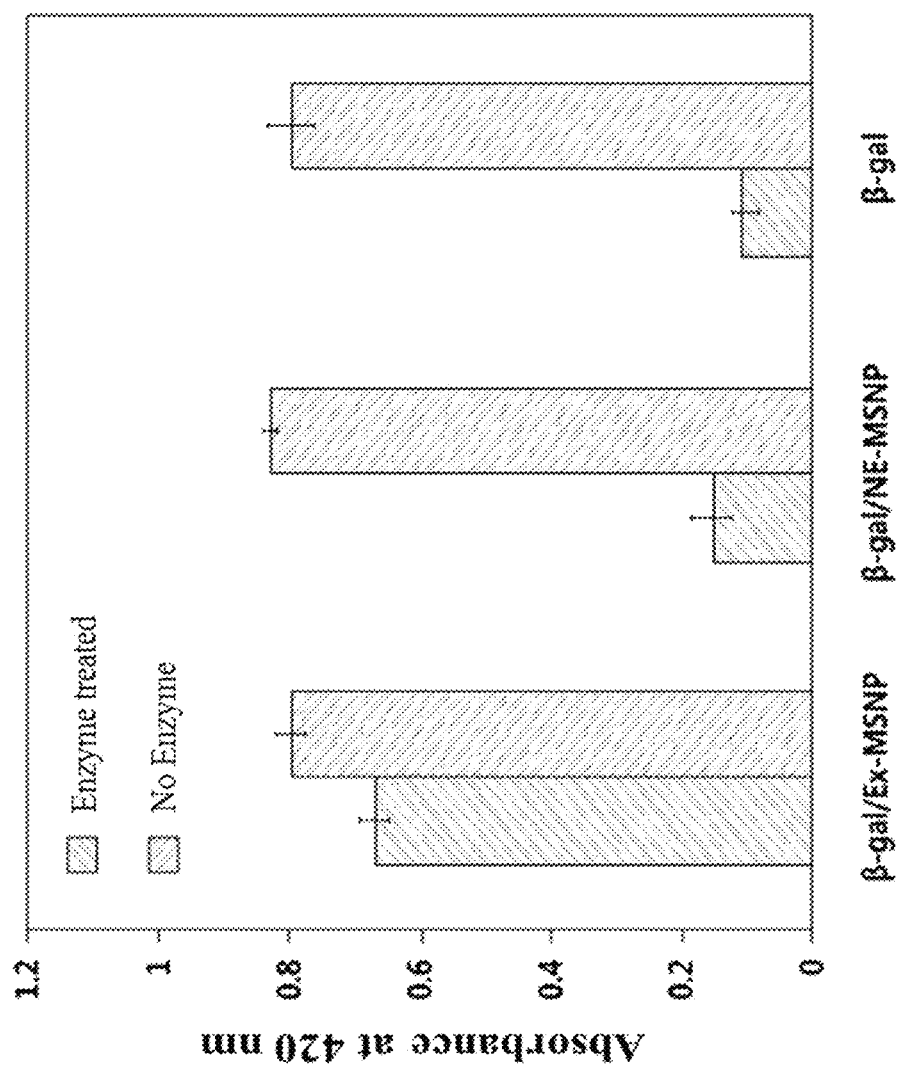
FIG. 7 is a graph showing the analysis of the effects of protease in the cells into which mesoporous silica nanoparticles including proteins according to one embodiment of the present invention were introduced.

Next, β-galactosidase was adsorbed or loaded to each of the pore-expanded MSN (Ex-MSNP) of the present invention and non-pore-expanded MSN (NE-MSNP) with an average pore size of 2 nm, and then these MSNs and β-galactosidase alone were each treated with chymotrypsin at 37° C. for 12 hours, and the ONPG analysis was conducted (see FIG. 7). FIG. 7 indicated that β-galactosidase was decomposed by the chymotrypsin if β-galactosidase was adsorbed or loaded to the NE-MSNP, whereas the β-galactosidase was protected from the chymotrypsin to exhibit a normal absorbance if β-galactosidase was adsorbed or loaded to the Ex-MSNP. Therefore, it was found that the substance adsorbed or loaded to the pore of the MSN of the present invention can be protected from external environment, to be introduced stably into cells.

Example 4: Analysis of the Function of Protein Introduced into Cell

In this Example, it was analyzed whether the protein adsorbed or loaded to MSN and introduced into a cell normally functioned, which was shown in a graph. HeLa cells and MDA-MB-231 cells were used as the cell line for protein introduction.

Figure 8:
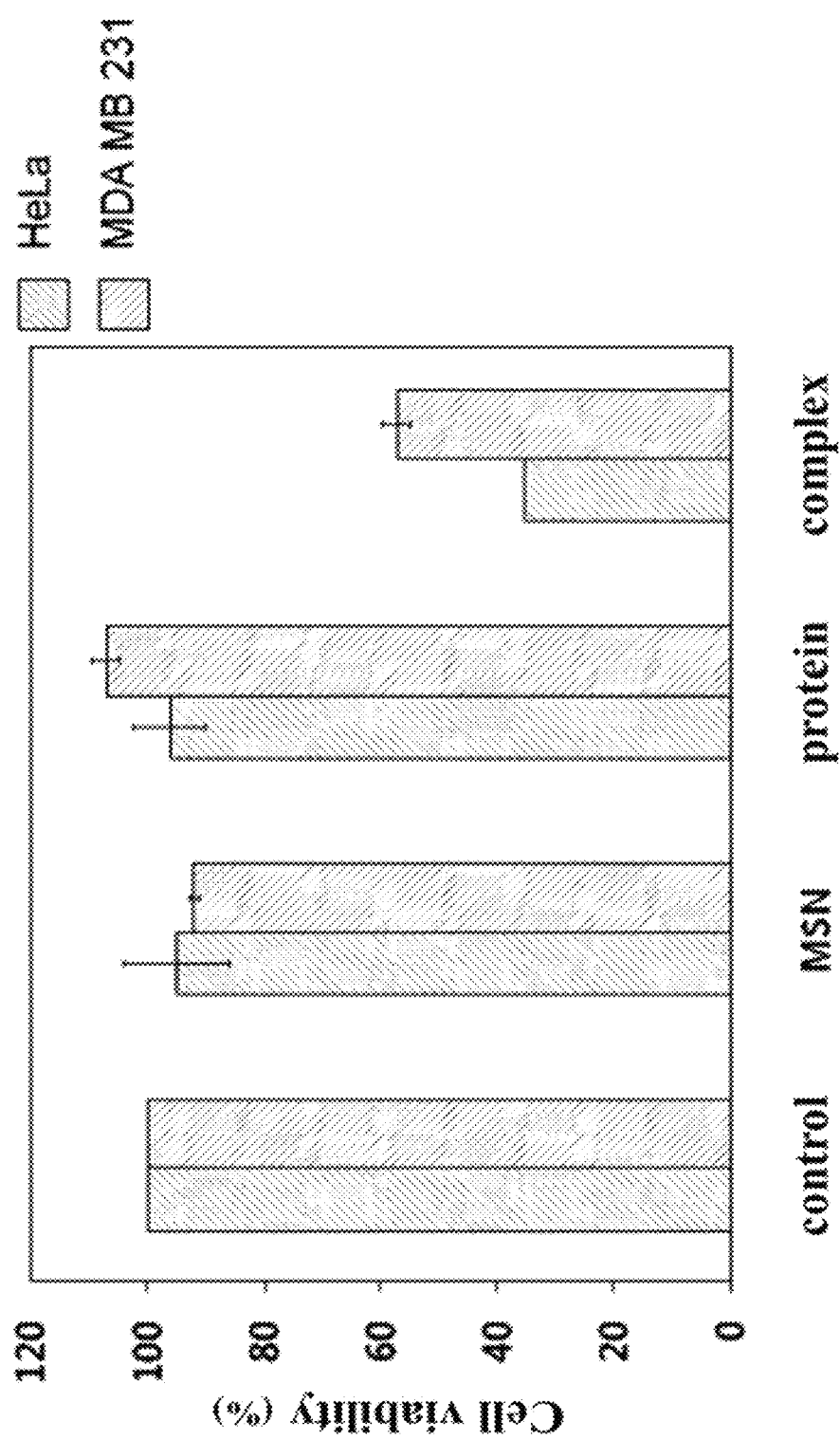
FIG. 8 is a graph showing the analysis on whether the protein normally functions in the cells into which mesoporous silica nanoparticles including proteins according to one embodiment of the present invention were introduced.

First, according to the Example 2, horseradish peroxidase (HRP) protein was adsorbed or loaded to the MSN exhibiting cations, which was then used for treating HeLa cells and MDA-MB-231 cells for 4 hours along with cell culture media. Then, the cell was washed twice with PBS and treated with indole acetic acid (IAA). And then, toxicity test was conducted to examine the effect of HRP-IAA combination on each cell line. As seen in the graph of FIG. 8, cytotoxicity was not observed in the cells treated with HRP protein alone or MSN alone, but cytotoxicity was observed owing to the transformation of IAA to reactive species by the enzymatic reaction caused by the activity of HRP protein, leading to the decrease in the cell survival rate in the cells treated with the MSN to which HHRP protein was adsorbed or loaded.

Figure 9:
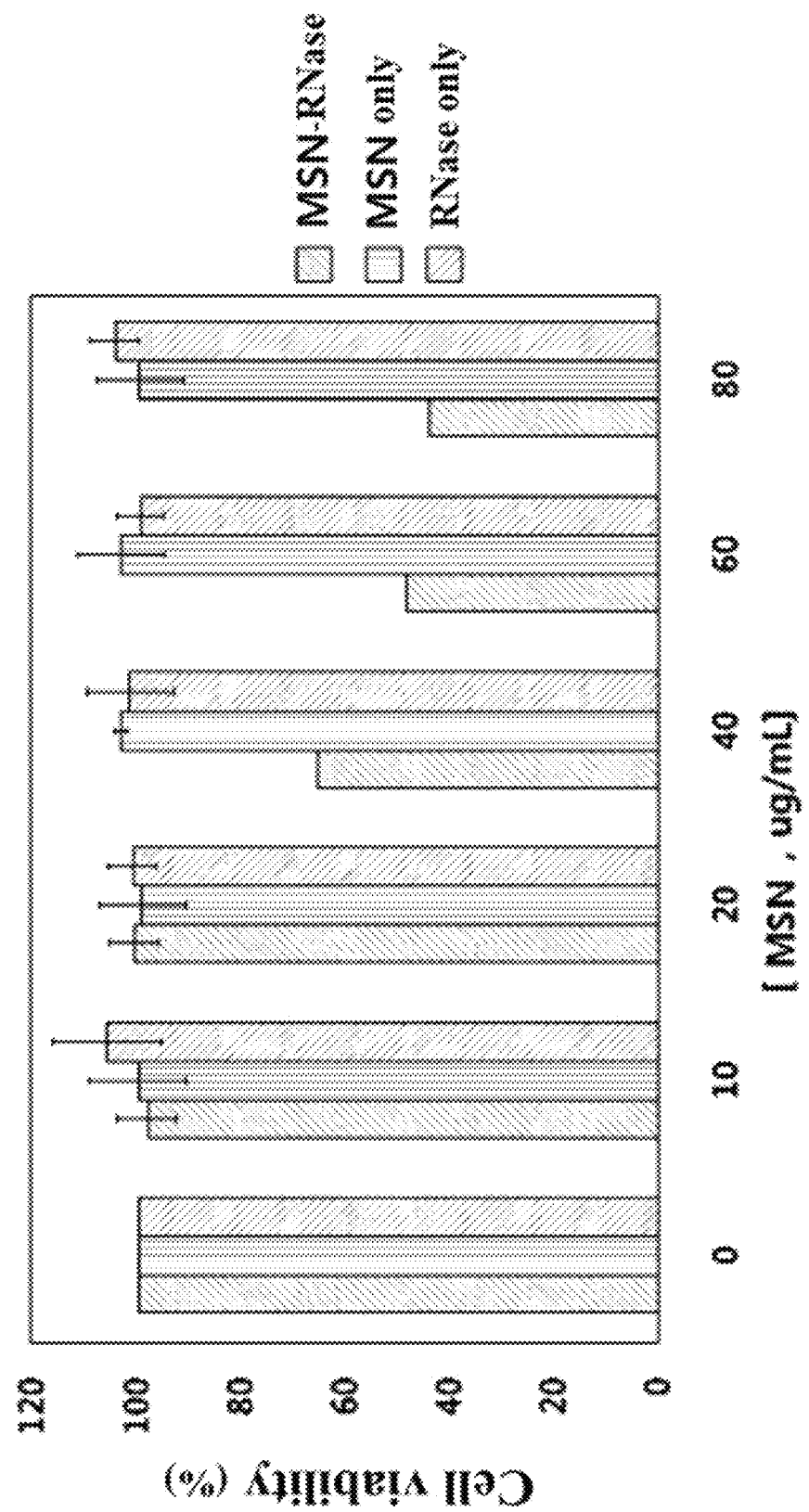
FIG. 9 is a graph showing the analysis on whether the protein normally functions in the cells into which mesoporous silica nanoparticles including proteins according to one embodiment of the present invention were introduced.

Next, according to the Example 2, RNase proteins in various concentrations were adsorbed or loaded to the MSN with the surface exhibiting anions, which were then used for treating the cells along with cell culture media, to conduct toxicity test. As a result, cytotoxicity was observed which was dependent on the concentration of the RNase protein adsorbed or loaded to the MSN (see FIG. 9).

Preparation Example 6: Preparation of Proteasome-MSN Complex

The purified proteasome and MSNPN prepared as in Preparation Example 2 were suspended in PBS in various molar ratios, and shaken horizontally at RT for 2 hours at 200 rpm. The resulting proteasome-MSNPN complex was centrifuged at 3000 rpm and washed 3 times. The complex was re-suspended in cell culture media for the introduction into cells.

Preparation Example 7: Affinity Purification of 26S Human Proteasome

Figure 12A:
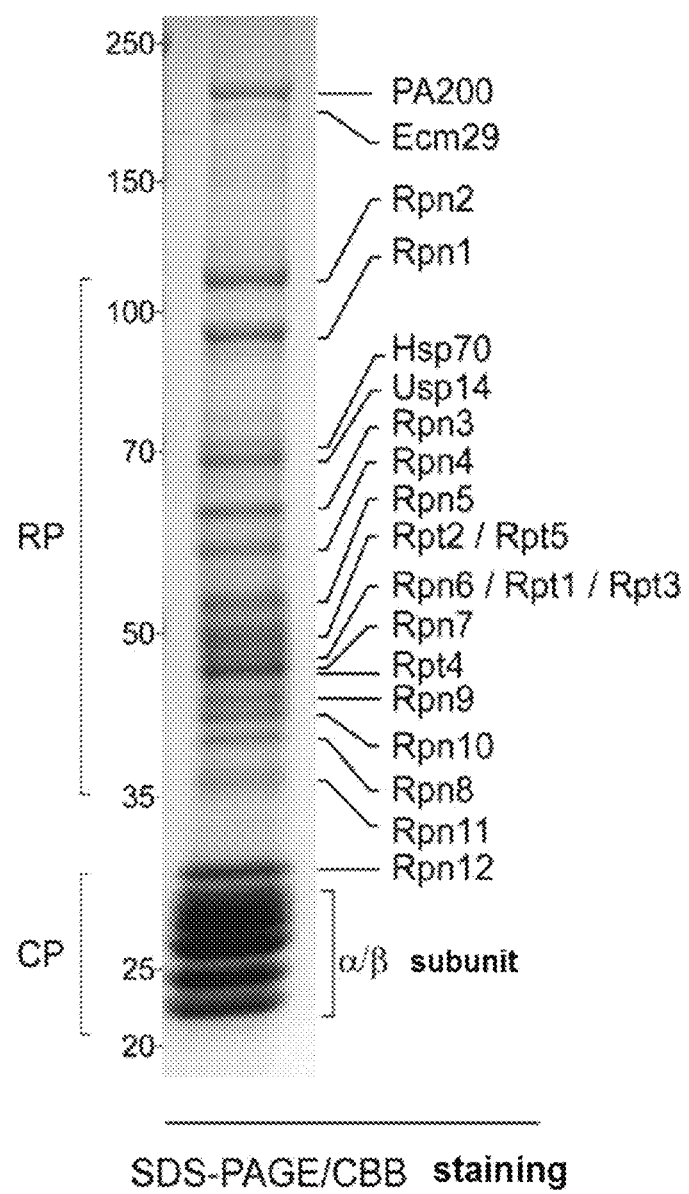
FIGS. 12a, 12b, and 12c respectively show the results of one-dimensional SDS-PAGE and CBB staining, non-modified gel analysis visualized by suc-LLVY(SEQ ID NO: 42)-AMC, and immunoblotting analysis using various antibodies against CP and RP subunits.
Figure 12B:
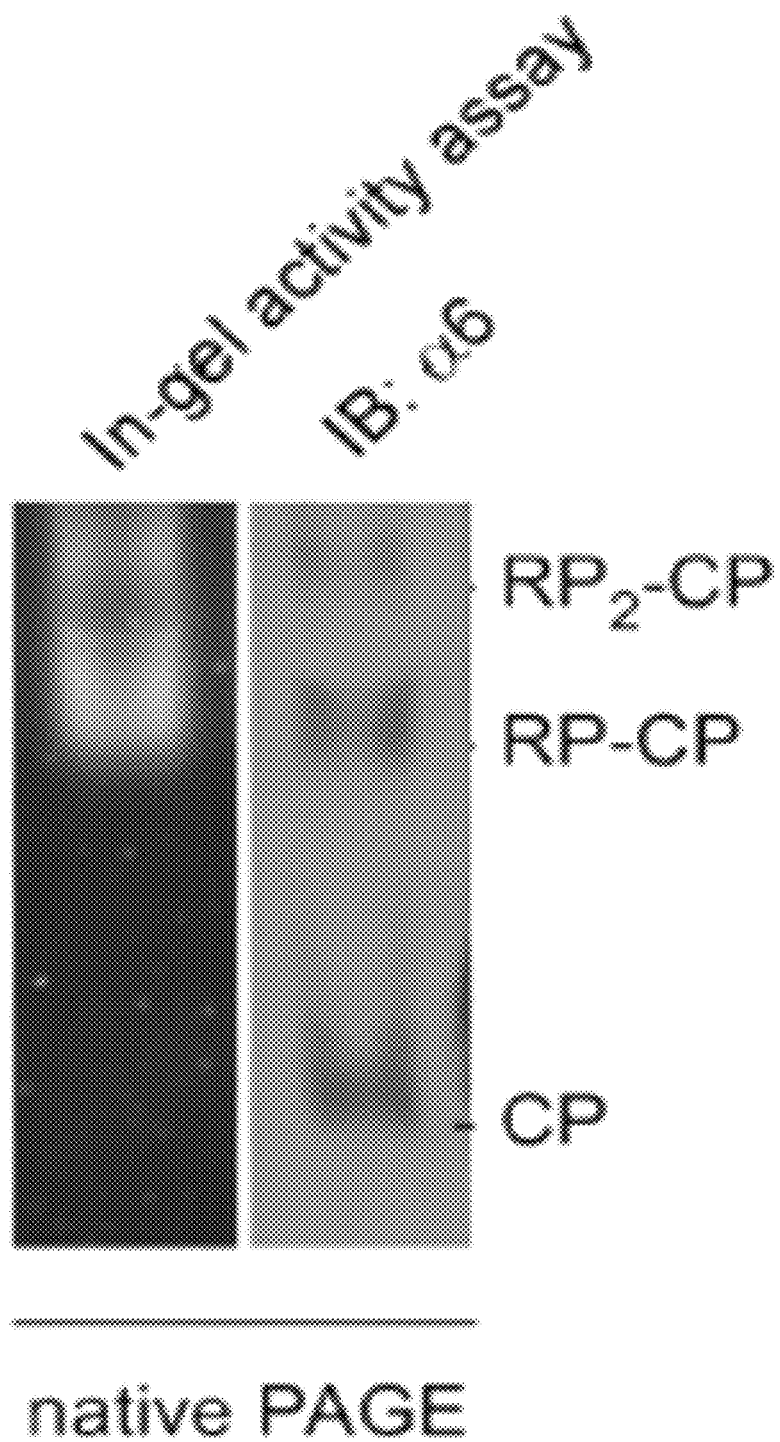
Figure 12C:
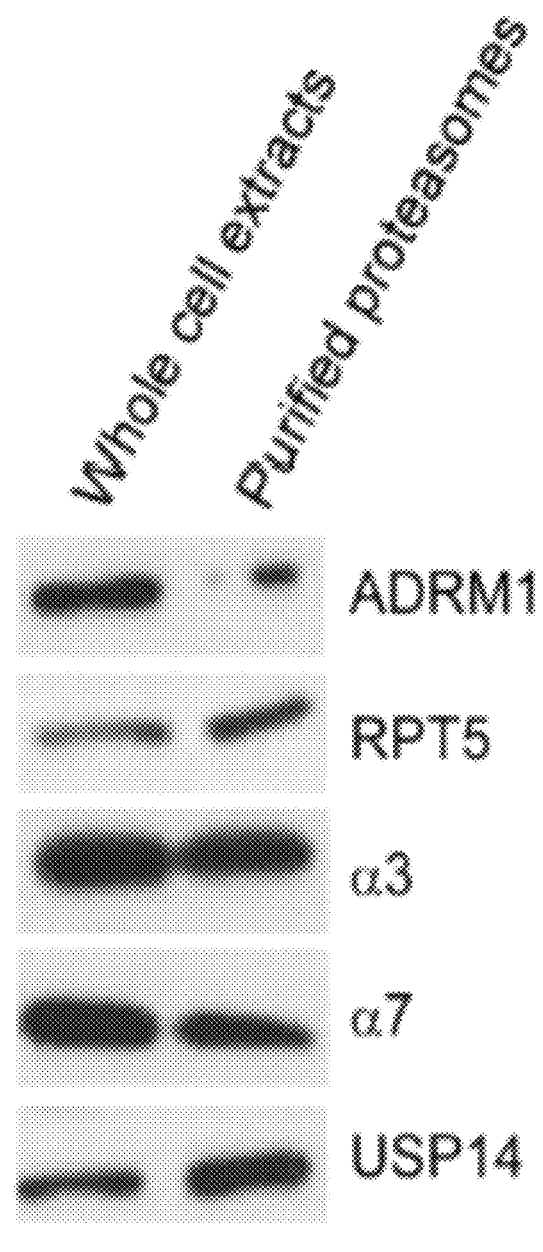

Human proteasome was affinity-purified from the stable HEK293T cell line having a HTBH-tagged β4 subunit. The cells were homogenized by Dounce tissue grinders (Wheaton) in a dissolution buffer (50 mM $NaH_2PO_4$, pH 7.5, 100 mM NaCl, 10% glycerol, 5 mM MgCl$_2$, 0.5% NP-40) containing protease inhibitor, 5 mM ATP, and 1 mM DTT. The dissolved substances were centrifuged at 10,000×g, and the clear supernatant was incubated with streptavidin agarose resin (Millipore) at 4° C. for 5 hours. Then the resin bead was incubated in an elution buffer (50 mM Tris-HCl, pH 7.5, 1 mM MgCl$_2$, 10% glycerol, and 1 mM ATP) containing TEV protease. Endogenous Usp14 was found on the proteasome under the purification conditions (FIGS. 12a, 12b and 12c). The human proteasome affinity-purified by His-tagged β4 subunit was analyzed by SDS-PAGE/Coomassie brilliant blue (CBB) staining (FIG. 12a).

The activated human 26S proteasome was effectively affinity-purified from HEK293-induced cell line which stably expresses both His-tagged and biotin-tagged β4 subunits (FIGS. 12a, 12b and 12c). Unlike the proteasome purified by a conventional method, these proteasomes had USP14 of a significant amount, a de-ubiquitinating enzyme loosely bound on RP, and an internal proteasome inhibitor.

Example 5: Transmission Electron Microscope (TEM)

TEM images were obtained by LIBRA 120 EF-TEM (Carl Zeiss, Germany) at 120 kV. Each MSN suspension was placed on a Formvar-coated copper grid and stabilized by evaporated carbon film (Electron Microscopy Sciences, PA, U.S.A.). The grids were dried at RT for several hours before observation. To compare the TEM images of MSNPN and the MSNPN adsorbed or loaded with proteasome, each sample was placed on the grid and stained with 0.5% uranyl acetate.

Example 6: Measurement of Proteasome Activity on MSNPN

In order to measure the activity of proteasome adsorbed or loaded to MSNPN, 12 µg of nanoparticle solution (10 mg/mL) and 2.4 µg of protease was incubated in PBS at 4° C. for 30 min to prepare the proteasome-MSNPN complex. Then, the complex was diluted with a calibration buffer (50 mM Tris, pH 7.5, 1 mM EDTA, 1 mg/mL albumin, 1 mM fresh ATP, 1 mM fresh DTT) to the final volume of 100 µL. And then, 10 µg of proteasome and proteasome-MSNPN in the calibration buffer were added to 96-well plates containing a fluorescent substrate suc-LLVY(SEQ ID NO:42)-AMC in the calibration buffer. Consequently, the fluorescence of AMC (ex 355/em 460) was measured.

Figure 13:
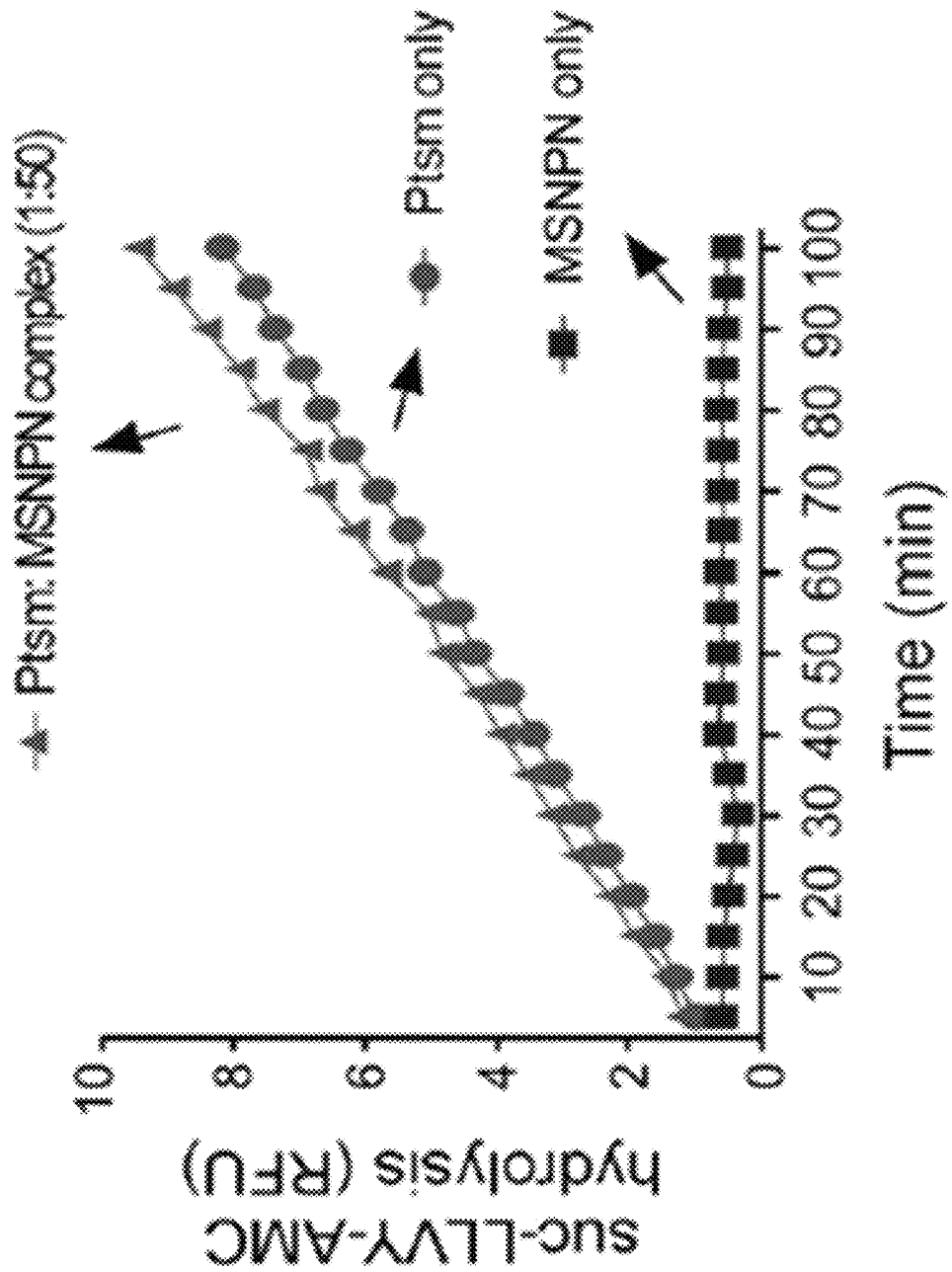
FIG. 13 is a graph showing suc-LLVY(SEQ ID NO: 42)-AMC hydrolysis analysis using MSNPN, proteasome, and a MSNPN-proteasome complex according to one embodiment of the present invention (RFU: Relative Fluorescence Unit).

The proteasome-MSN complex had a similar proteolytic activity to that of non-bound proteasome, which suggested that these can entirely gain access to the small peptide-based reporter substrate even when bound to the pores of MSPSN (FIG. 13).

Example 7: Analysis of Proteasome-MSN Complex

The proteasome-MSN complex was prepared by the method of Example 6, except that proteasome was cultured with the MSN. Then, the cultured samples were spin-downed and the pellet fraction was analyzed by SDS-PAGE and immunoblotting (TB). For comparison, proteasome alone in the same amount as the proteasome-MSN complex was added thereto.

The isolation of the purified proteasome from the proteasome-MSN complex was conducted by a short-centrifugation and then immunoblotting at the presence of 0.5 M imidazole, which was then evaluated. The purified proteasomes were bound to MSNPN in various mass ratios, and the mixtures were centrifuged at 1,000×g for 5 min. The unbound proteasomes in the supernatant were discarded and the pellet was mixed with 2×SDS sample buffer containing 2% β-mercaptoethanol or incubated with 0.5 M imidazole for 1 hours. Immunoblotting was conducted using anti-His antibody.

Figure 14A:
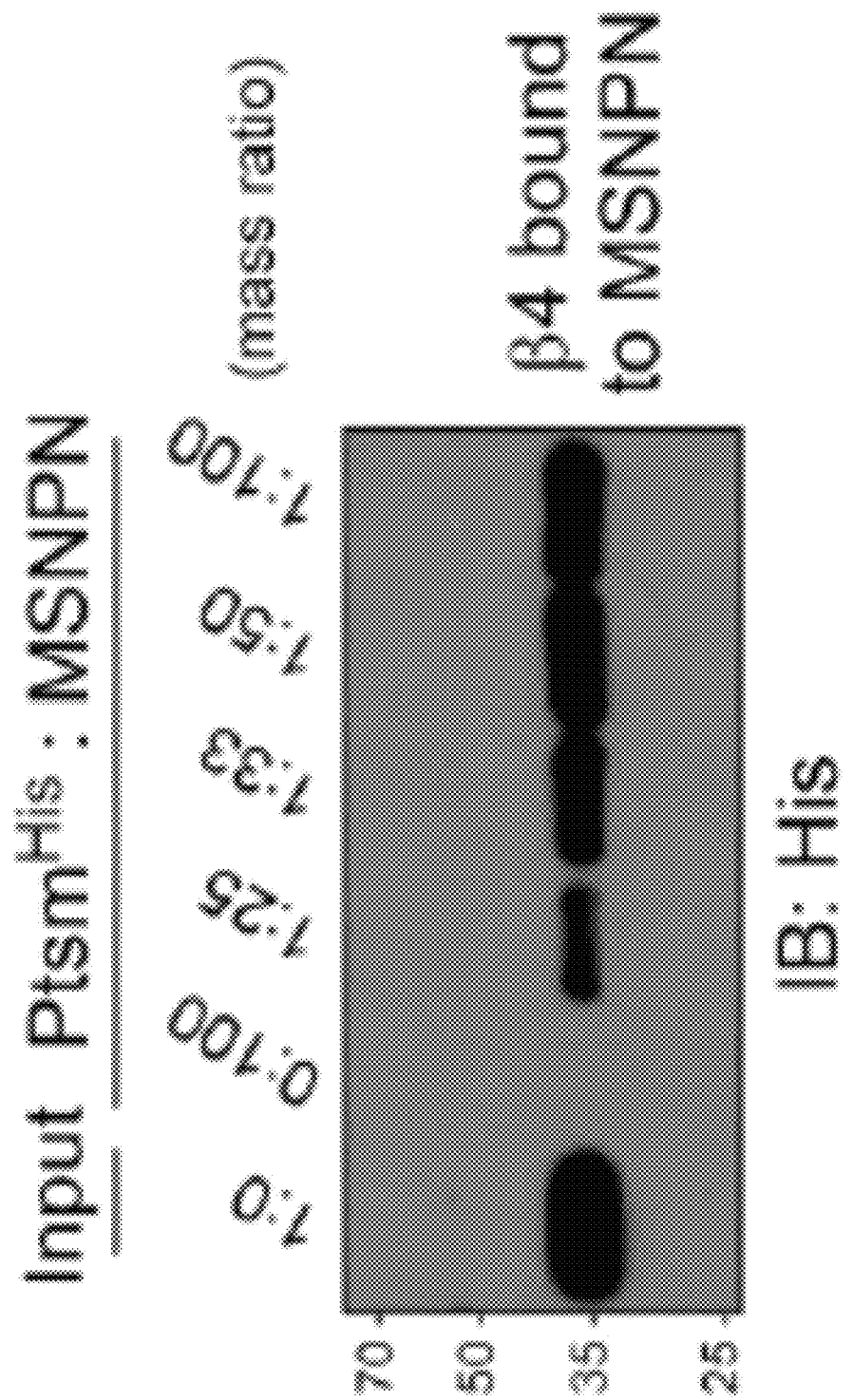
FIGS. 14a and 14b are the images showing the results of immunoblotting, and imidazole elution calibration test, respectively, using proteasome and proteasome-MSNPN according to one embodiment of the present invention.
Figure 14B:
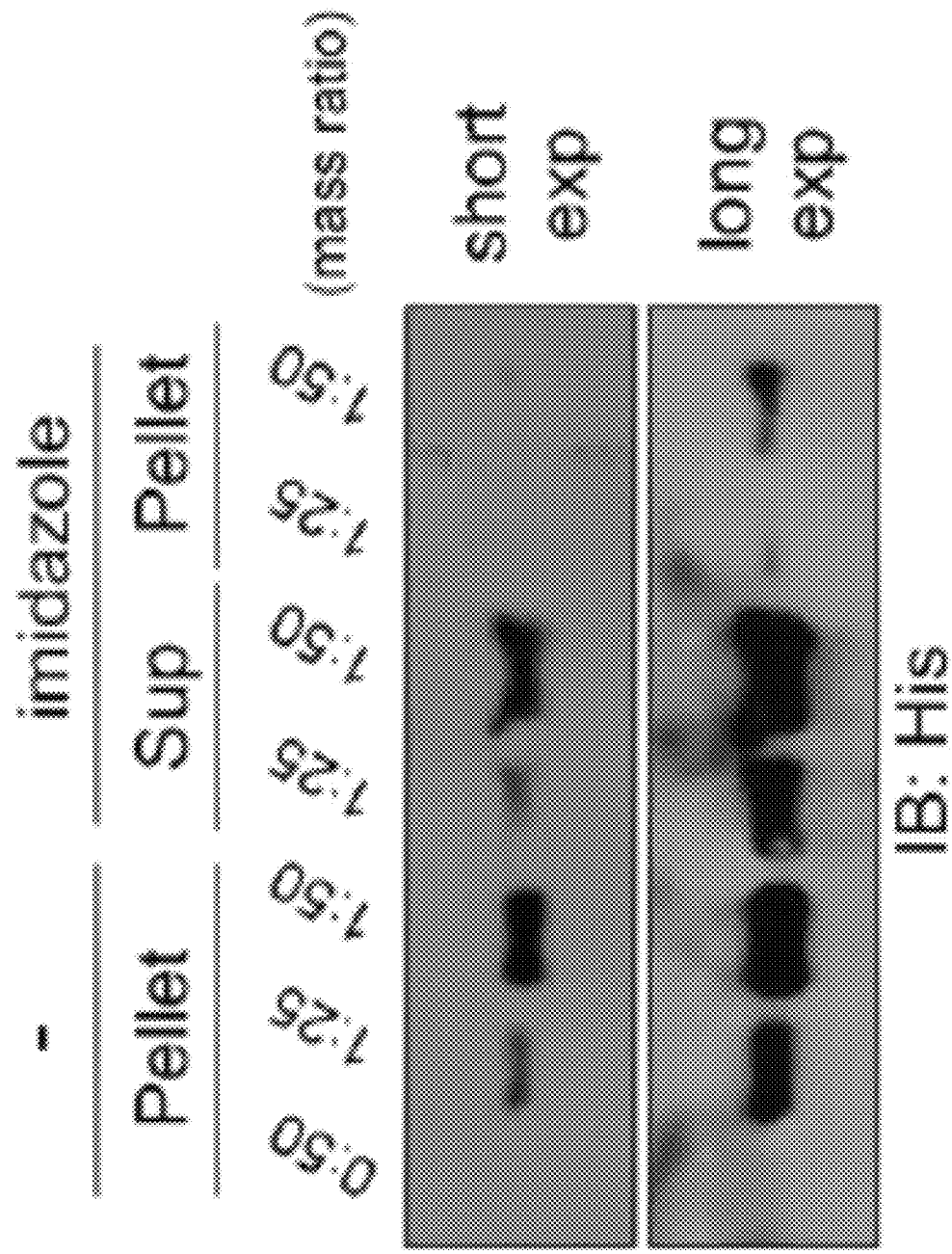

The proteasomes purified in various mass ratios were easily adsorbed or loaded to MSNPN, which was saturated when the ratio (proteasome/nanoparticle) was 1:50 or ~37 proteasome-complete enzymes were charged to the single nanoparticle (FIG. 14a). The formation of proteasome-MSNPN complex was mainly mediated by non-covalent His-Nickel interaction instead of a simple absorption or electrostatic binding. When it was incubated with 0.5 M imidazole, the proteasome bound to MSNPN was effectively released into the supernatant by the excessive imidazole (FIG. 14b).

Figure 15A:
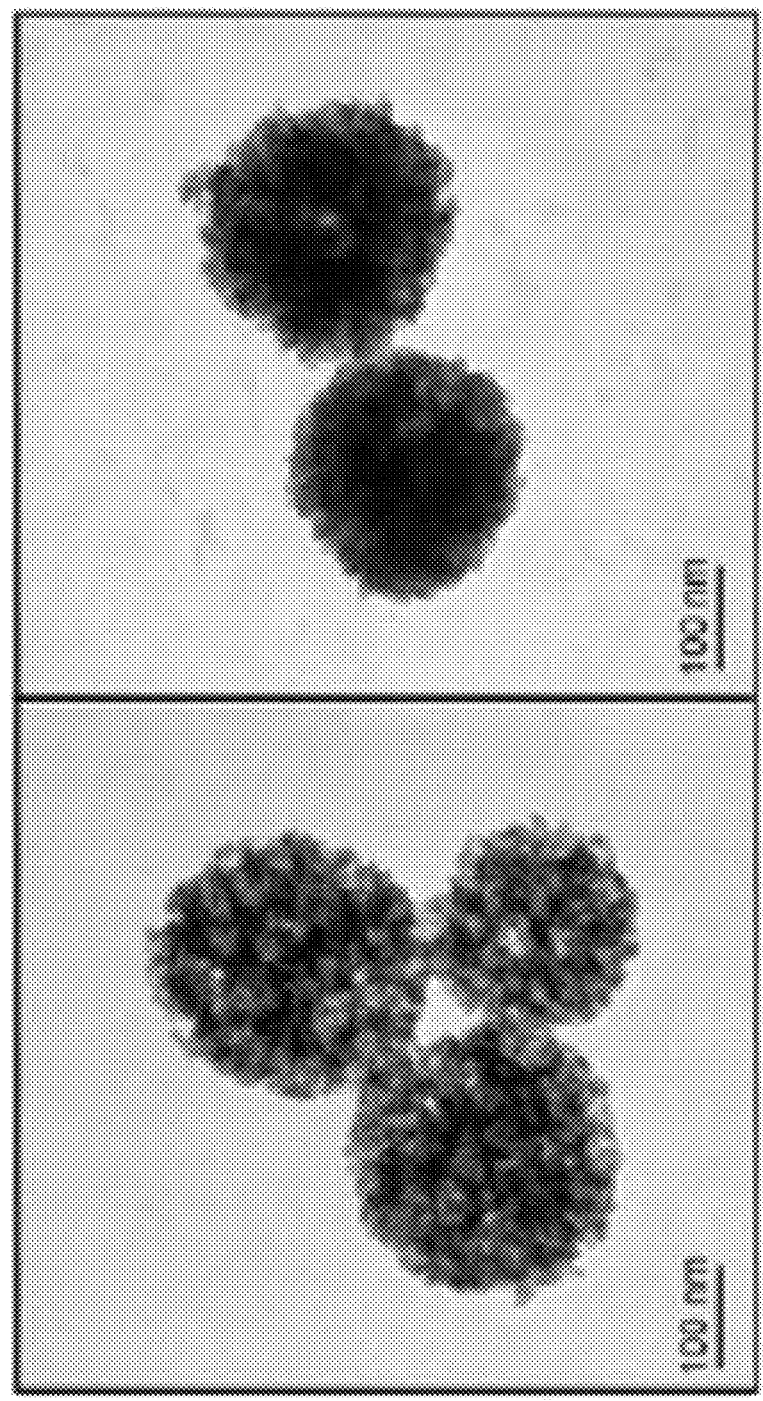
FIGS. 15a and 15b show a transmission electron microscope (TEM) images, and a graph of DLS (dynamic light scattering) analysis results, respectively, using MSNPN and proteasome-MSNPN according to one embodiment of the present invention.
Figure 15B:
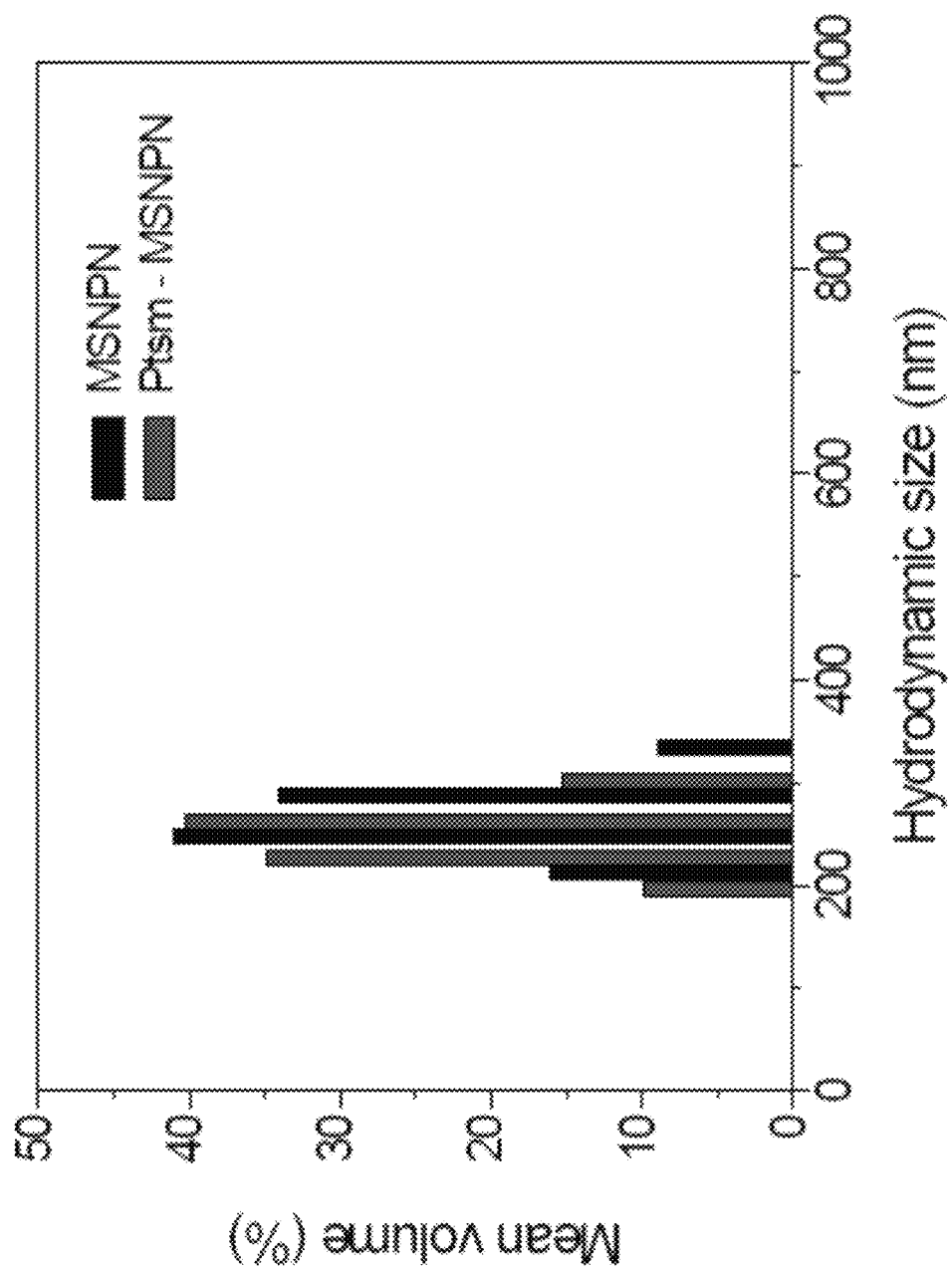

The Zeta-potential and the hydrodynamic size of MSNPN and the MSNPN adsorbed or loaded with proteasome were measured by dynamic light scattering (DLS) analysis using Zetasizer NanoS (Malvern instruments, UK). The surface Zeta-potential of the nanoparticle smoothly increased from −12.60 mV to −6.38 mV after adsorbing or loading of the proteasome, which indicated reduced electrostatic repulsion between the particles, and the stable complex formation between proteasome and MSNPN (Table 4 below). The microscopic property of the nanoparticle was similar between before and after the proteasome charging although the size of the complex and the pore decreased slightly (FIGS. 15a and 15b, and Table 5, below). Thus, the purified proteasome was effectively adsorbed or loaded to the novel MSN by the non-covalent interaction.

TABLE 4

|  | Zeta potential (mV) |
| --- | --- |
| MSNPN | −12.60 ± 0.79 |
| Proteasome-MSNPN | −6.38 ± 0.42 |

TABLE 5

|  | Hydrodynamic size (nm) |
| --- | --- |
| MSNPN | 267 ± 46 |
| Proteasome-MSNPN | 239 ± 27 |

Example 8: Analysis of Suc-LLVY(SEQ ID NO:42)-AMC Hydrolysis

Proteasome, MSN and the proteasome-MSN complex were measured by suc-LLVY(SEQ ID NO:42)-AMC hydrolysis analysis.

Example 9: Decomposition of In Vitro Proteasome

Figure 16:
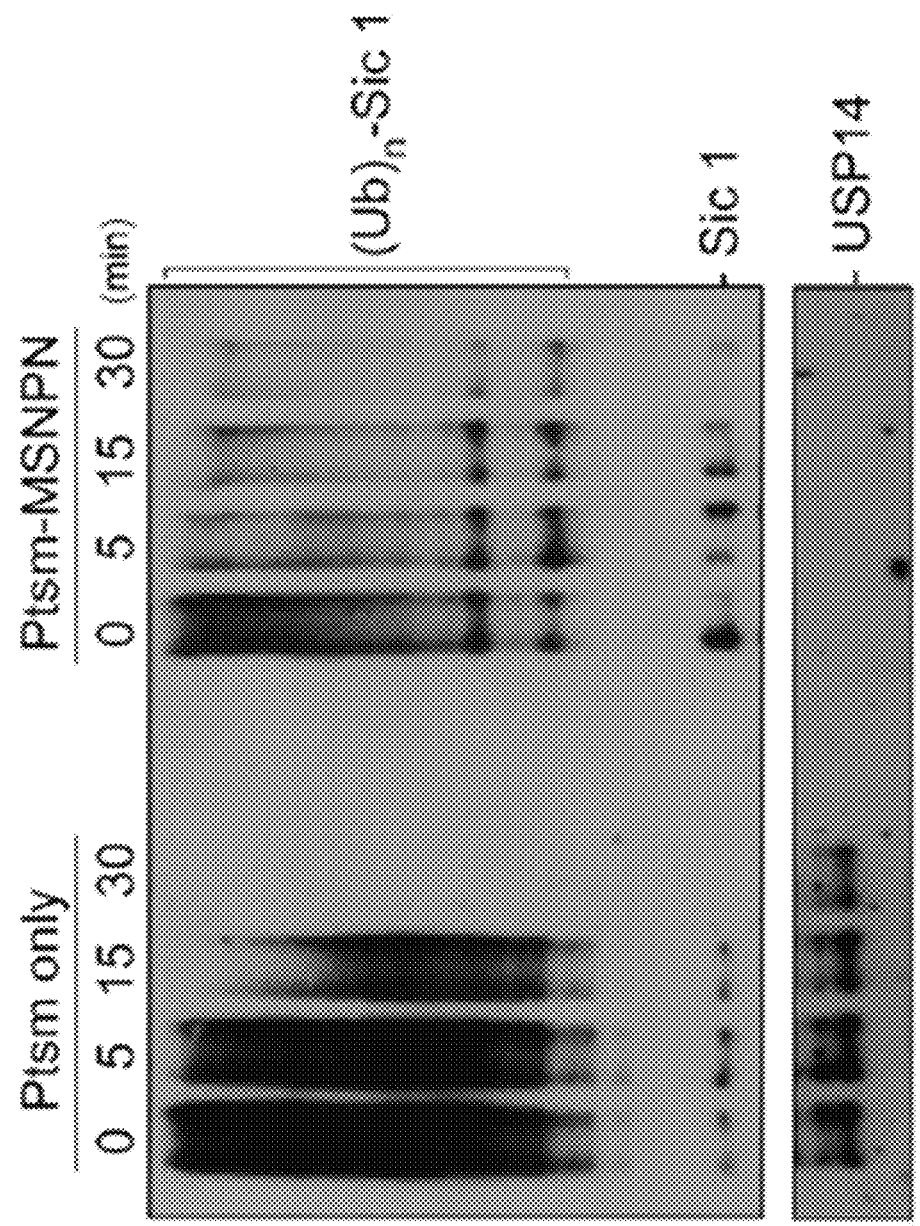
FIG. 16 is a SDS-PAGE/IB image showing the result of in vitro proteasome decomposition analysis regarding proteasome and proteasome-MSNPN according to one embodiment of the present invention.

In order to examine the decomposition by the proteasome-MSN complex, in vitro Ub-Sic1 decomposition calibration was conducted using poly-ubiquitinated Sic1$^{PY}$ (Ub-Sic1), which is more physiologically associated proteasome substrate. The reactions with proteasome or proteasome-MSNPN complex for various time durations were analyzed by SDS-PAGE/IB using anti-T17 and anti-USP14 antibodies. Purified human proteasome or proteasome-MSNPN complex (5 nM) was incubated with poly-ubiquitinated Sic1$^{PY}$ (Ub-Sic1$^{PY}$) (20 nM) in a proteasome calibration buffer (50 mM Tris-HCl, pH 7.5, 100 mM NaCl, 10% glycerol, 2 mM ATP) for various time durations. The samples were mixed with 2×SDS sample buffer, boiled at 75° C. for 10 min, and then immunoblotted using anti-T7 antigen. Ub-Sic1 was completely decomposed within 30 min's culture when the purified proteasome keeping USP14 was used in Ub-Sic1 (FIG. 16). In the present Example, although the proteasome which was bound to MSNPN decomposed Ub-Sic1, it was found that the decomposition was carried out with pattern a very distinctive from that of proteasome alone. Specifically, the proteasome-MSN complex at initial point decomposed Ub-Sic1 more rapidly than proteasome alone, and less Ub-chain-trimming effect was observed. This may suggest the transposition of internal USP14 from proteasome during the formation of the complex (FIG. 16). The proteasome activity increased by the shortage of USP14 in the complex may be advantageous in the direct proteasome delivery strategy.

Example 10: TEM Analysis of MSNPN-Treated Cells

Cells treated with MSNPN (80 μg/mL) were fixed with 2% paraformaldehyde and 2% glutaraldehyde in 0.05 M sodium cacodylate buffer (pH 7.2) at 4° C. for 4 hours. The samples were washed 3 times with 0.05 M sodium cacodylate buffer (pH 7.2), and post-fixed with 1% osmium tetroxide ($OsO_4$) in 0.05 M sodium cacodylate buffer (pH 7.2) at 4° C. for 2 hours. Then the samples were washed with water, and stained altogether by 0.5% uranyl acetate in distilled water. Then the samples were dehydrated by a series of 30% to 100% ethanol, and dehydrated twice by 100% propylene oxide at RT for 15 min. The samples were penetrated by Spurr resin (mixed with ERL 4221, DER® 736 epoxy resin, NSA and DMAE) series. Finally, the samples were placed in a new 100% Spurr resin contained in the mold and polymerized overnight at 70° C. Ultrathin sections were prepared by ultramicrotome MTX (RMC, USA). The sections were adsorbed or loaded to the Formvar-coated copper grid, and observed by TEM (JEM 1010, JEOL, Japan) at 80 kV.

Example 11: Cell Culture

The cells used in the Examples, including HELA, HEK293-pre1-HTBH, HEK293-trex-htau40, and tau-BiFC were cultured in Dulbecco's modified Eagle's medium (DMEM) containing 4.5 g/L D-glucose and, 10% Fetal Bovine Serum (FBS), 100 units/mL penicillin and 100 g/mL streptomycin as supplements. The cells were kept in a humidified incubator at 37° C. and 5% $CO_2$. One day prior to the treatment with the proteasome-MSNPN complex, the cells were inoculated onto a round cover glass (φ 25 mm, No. 1, Deckglaser, Germany). Before the experiment, the complex or the control cells were added to the attached cells on the cover glass and the medium was removed after incubation time elapsed. The cells were intensively washed 3 times with PBS to remove the unbound nanoparticles, and the fluorescence images were obtained.

Example 12: Evaluation of Internalization of Proteasome into Cell

Figure 17A:
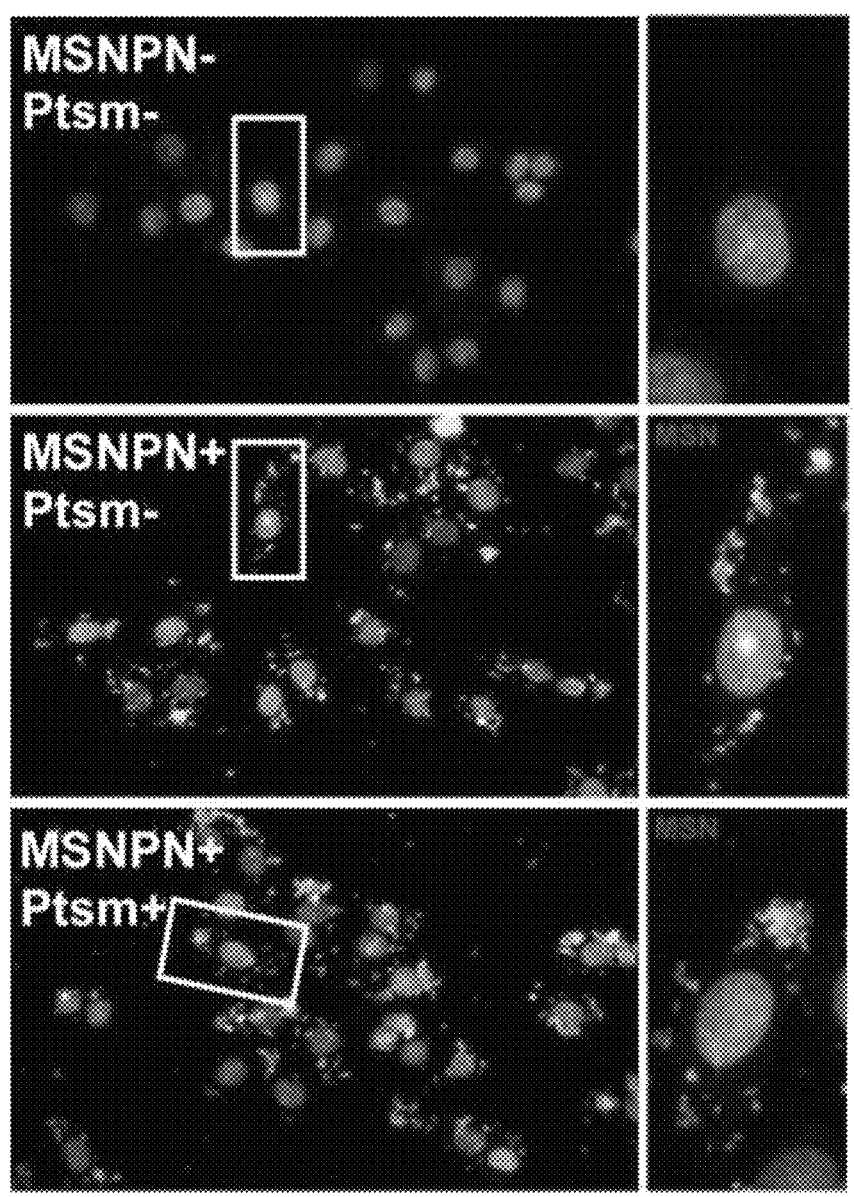
FIGS. 17a and 17b are respectively fluorescence microscopic images and TEM images of the HeLa cells treated with TAMRA-labeled MSNPN or proteasome-MSNPN according to one embodiment of the present invention. The arrow indicates MSNPN localized in the cytoplasm.
Figure 17B:
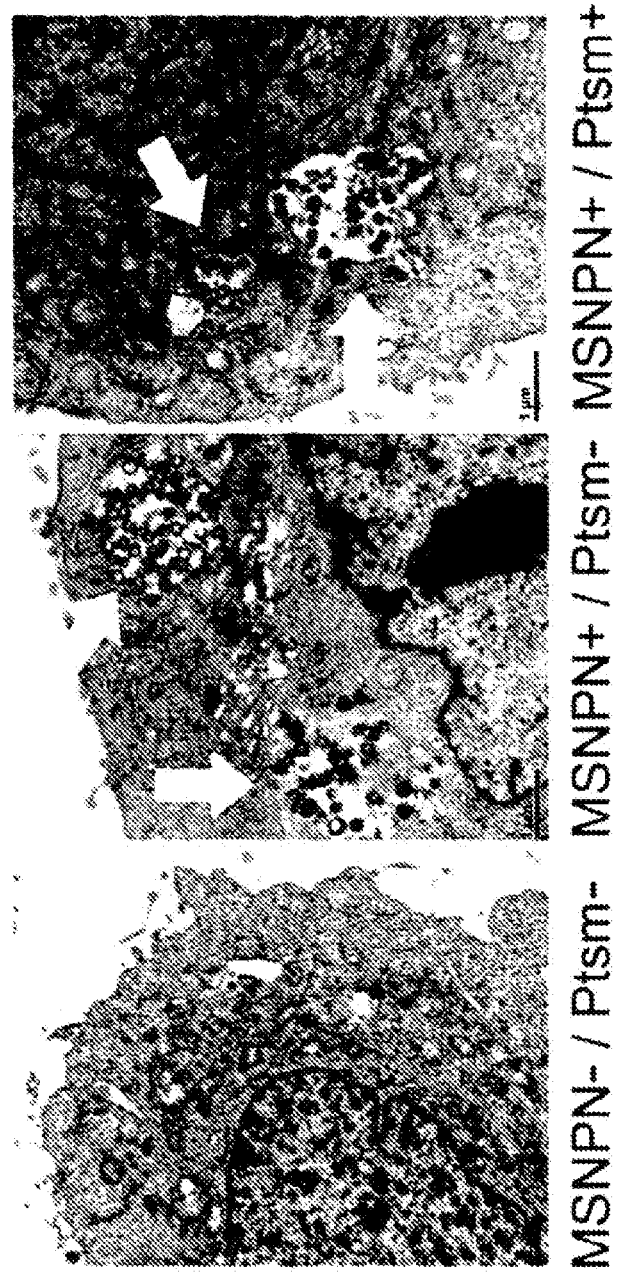
Figure 18A:
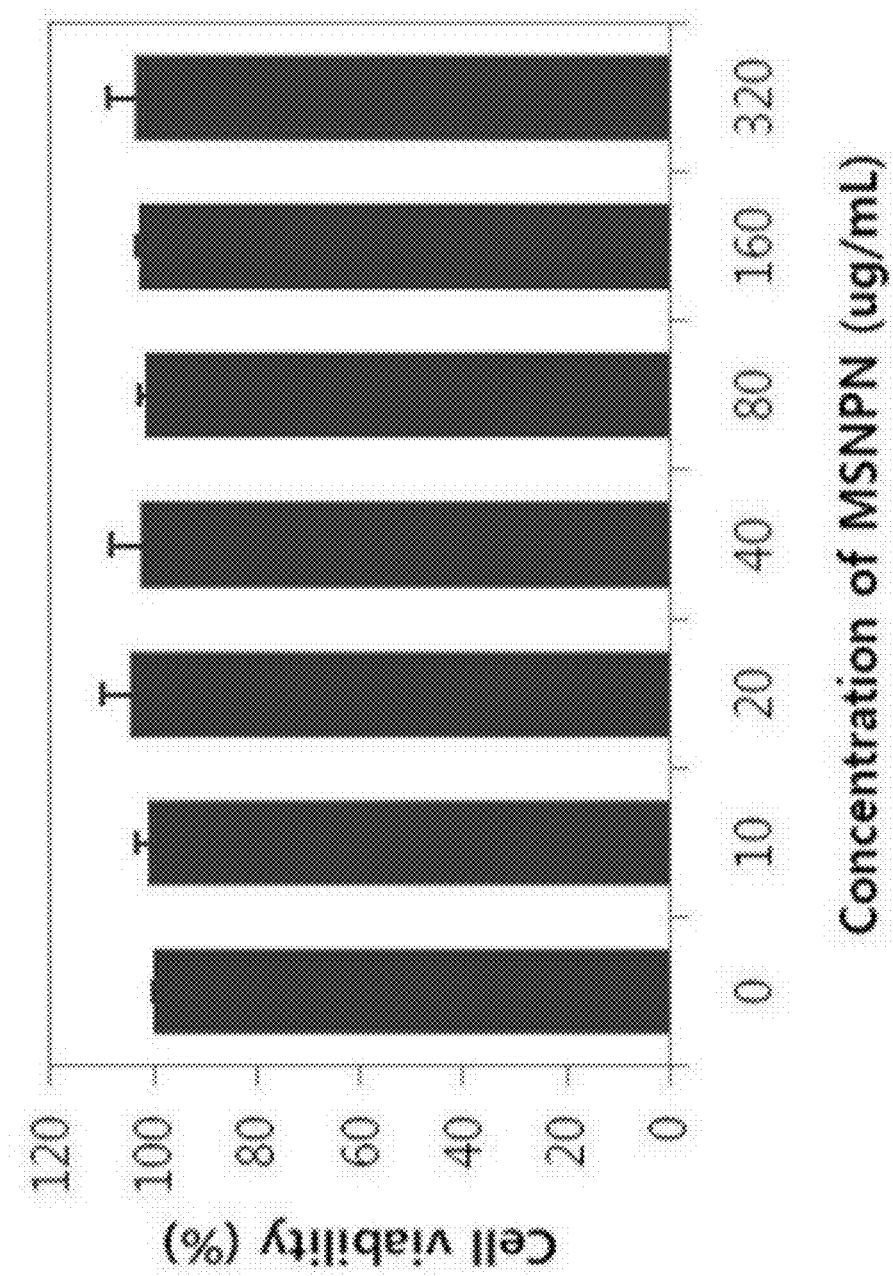
FIGS. 18a and 18b are graphs showing the cytotoxicity according to the concentrations of MSNPN and proteasome-MSNPN, respectively, according to one embodiment of the present invention.
Figure 18B:
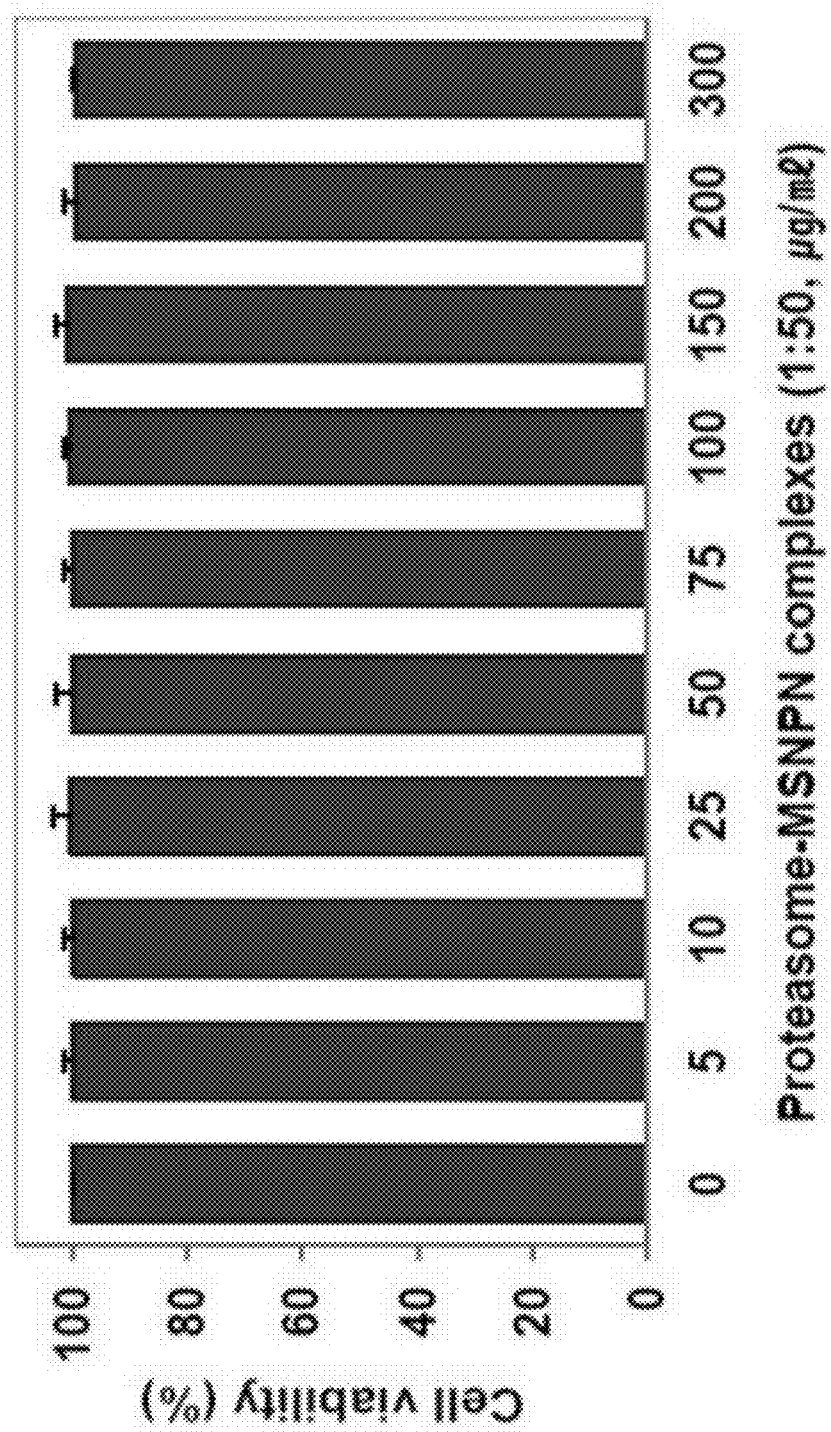

In order to examine whether MSNPN enables the internalization of proteasome into cells, TAMRA-tagged MSNPN-proteasome complex (5 of FIG. 10b) was added to the culture medium containing serum. Then, the cells were treated with TAMRA-tagged MSNPN alone or the proteasome-MSNPN complex (1:50) for 24 hours, then washed vigorously, and then HeLa cells were examined by fluorescence, confocal and transmission electron microscopy (FIG. 17a and FIG. 17b). The complex was found mainly in the cytoplasm, which indicates the accumulation in endocytotic vesicle. The complexes entered into the cells in various concentrations and molar ratios within 2 hours of the culture, and kept in the cytosol for at least 96 hours (data not shown). The mild effect on the cell survival of MSNPN or proteasome-MSNPN was observed in the concentration less than 300 μg/mL (FIGS. 18a and 18b).

Example 13: Endocytosis of MSNPN at the Presence of Endocytosis Inhibitor

Cells were treated with proteasome-MSNPN complex at the presence of various endocytosis inhibitors such as genistein, chlorpromazine, and nocodazole, and then measured by fluorescence microscopy and flow cytometry. HeLa cells were inoculated to 12-well plates and cultured in the incubator. After 24 hours, as the cells were incubated at 37° C. or at 4° C. (in serum-free culture medium) for 1 hour, the cells were treated with chlorpromazine (10 g/mL) to inhibit a clathrin-dependent endocytosis, genistein (200 M) to inhibit caveolae-dependent endocytosis, or amiloride (50 μM) and nocodazole (20 μM) to inhibit macropinocytosis. Then, the cells were incubated for 1 hour under the same condition as 20 g/mL of MSNPN, and washed 3 times with 2 mL of PBS. In order to quantitate the absorption of nanoparticles, the cells were trypsinized and collected, which were then centrifuged at 4° C., and washed with cold PBS. The cells were re-suspended in PBS containing 1% FBS, and filtered. The fluorescence intensity was measured by Aria III flow cytometry (Becton Dickinson, USA) equipped with argon laser. The experiment was conducted 3 times and the data were expressed as mean±SD.

The endocytosis of the complex was found to be energy-dependent, through both types of endocytosis (caveolae-mediated and clathrin-mediated endocytosis). However, chlorpromazine (decomposition inhibitor of clathrin) delayed the internalization of nanoparticles more than genistein (caveolae-related tyrosine kinase), or amiloride and nocodazole (micropinocytosis inhibitor), which suggests that cholesterol-rich lipid rafts can be utilized for surrounding the relatively large MSNPN.

Figure 19:
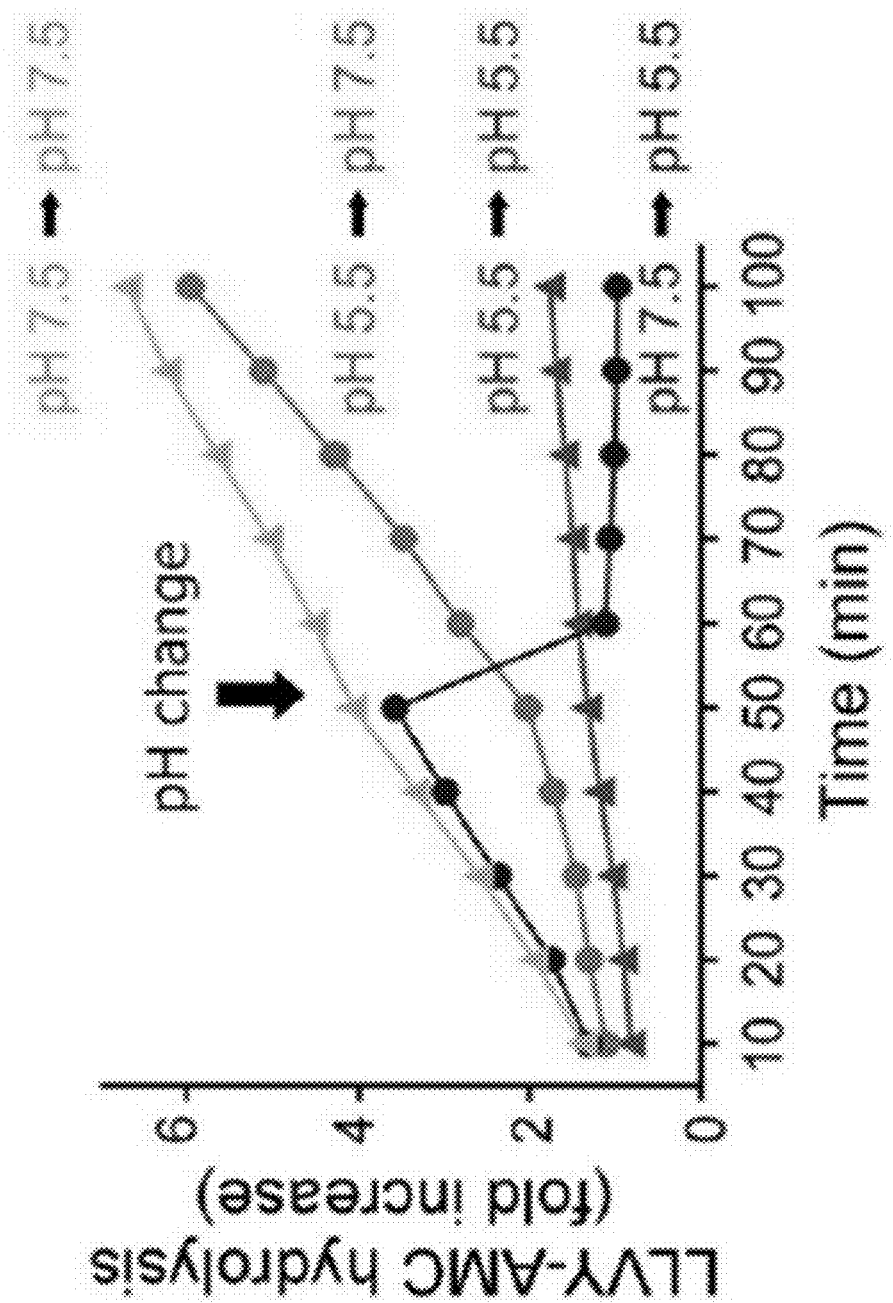
FIG. 19 is a graph showing the result of suc-LLVY(SEQ ID NO:42)-AMC analysis of proteasome-MSNPN according to one embodiment of the present invention under various pH conditions.

The result suggests that proteasome-MSNPN complex gets internalized through endocytosis transport. In order to examine whether an external proteasome gets activated and is structurally stable after the transport, the proteasome was cultured under the condition of acidic pH-mimicking endosome, and its proteolysis activity was monitored. The activity of proteasome was approximately four times lower at pH 5.5 than at pH 7.5 (FIG. 19). However, as pH increased, by decreasing the pH to 5.5, the activity of proteasome decreased whereas the proteolysis activity was recovered to a normal level.

The activities of components and proteasome before and after the pH change were measured by native PAGE. The purified proteasome or the whole cell lysate samples were dissolved in 3.5% non-denatured PAGE at 850 volt-hour and proteasome was visualized with a fluorescence substrate suc-LLVY(SEQ ID NO:42)-AMC (Bachem). After the pH change, no significant change in the proteasome components or gating was observed.

Example 14: Activity of Intracellular Proteasome

It was examined whether the delivery of MSNPN-mediated proteasome can affect the total activity of the intracellular proteasome. HeLa cells were treated for 24 hours with the proteasome-MSNPN complex prepared as in Preparation Example 6, and dissolved in 50 mM of $NaH_2PO_4$ (pH 7.5) containing 100 mM NaCl, 5 mM $MgCl_2$, 10% glycerol, 0.2% $NP_4O$, 1 mM ATP, 1 mM DTT and a protease inhibitor. The dissolved substances were homogenized by 26 G ⅜" syringe and centrifuged at 12,000 rpm for 10 min. The resultant supernatant without nanoparticles was used to measure the activity of LLVY(SEQ ID NO:42)-AMC hydrolysis. The pellet containing proteasome-MSNPN complex was re-suspended in a calibration buffer (50 mM Tris, pH 7.5, 1 mM EDTA, 1 mg/mL albumin, 1 mM fresh ATP, 1 mM fresh DTT), and the activity of proteasome was measured by 40 μM LLVY(SEQ ID NO:42)-AMC. The measurement was conducted in 37 cycles with 2 min intervals. It was found that the activity of proteasome was inhibited by 10 μM MG132, based on the dissolved substances and the activity of LLVY(SEQ ID NO:42)-AMC hydrolysis.

A markedly increased activity was observed in the pellet section of the proteasome-delivered cells which kept the internalized human proteasome, whereas the activity of LLVY(SEQ ID NO:42)-AMC hydrolysis in the supernatant of proteasome-MSNPN complex-treated cells was virtually the same as the activity of untreated cells. As reported in prior studies, the activity of proteasome enhanced by the MSNPN-mediated proteasome delivery was found to be acceptable to the cells (FIG. 18b), and there were no significant changes in the cellular levels of poly-ubiquitin and free-ubiquitin, or RP and CP subunits.

Example 15: Decomposition of Tau Protein by Proteasome

Figure 20A:
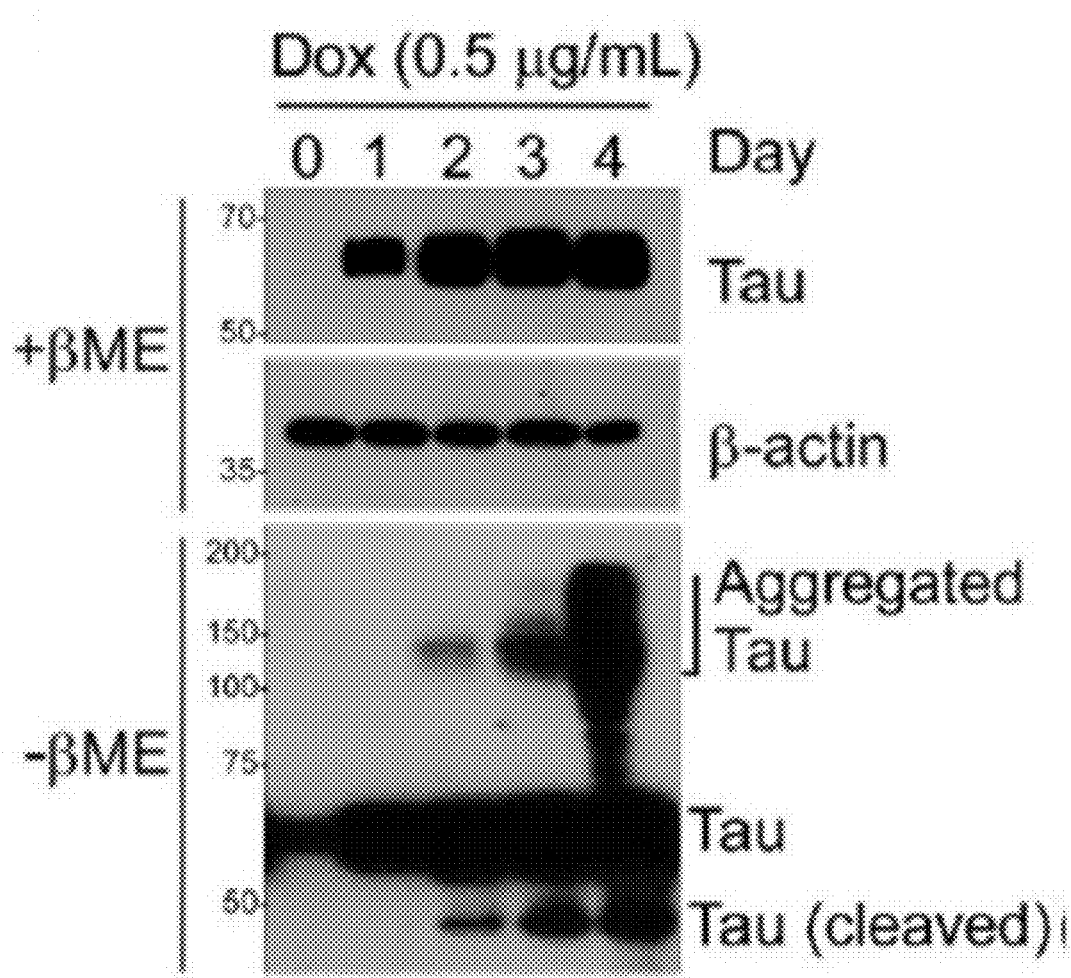
FIGS. 20a and 20b are images showing the result of the inducible tau cell line according to Dox treatment period, and the concentration of treatment, respectively, according to one embodiment of the present invention.
Figure 20B:
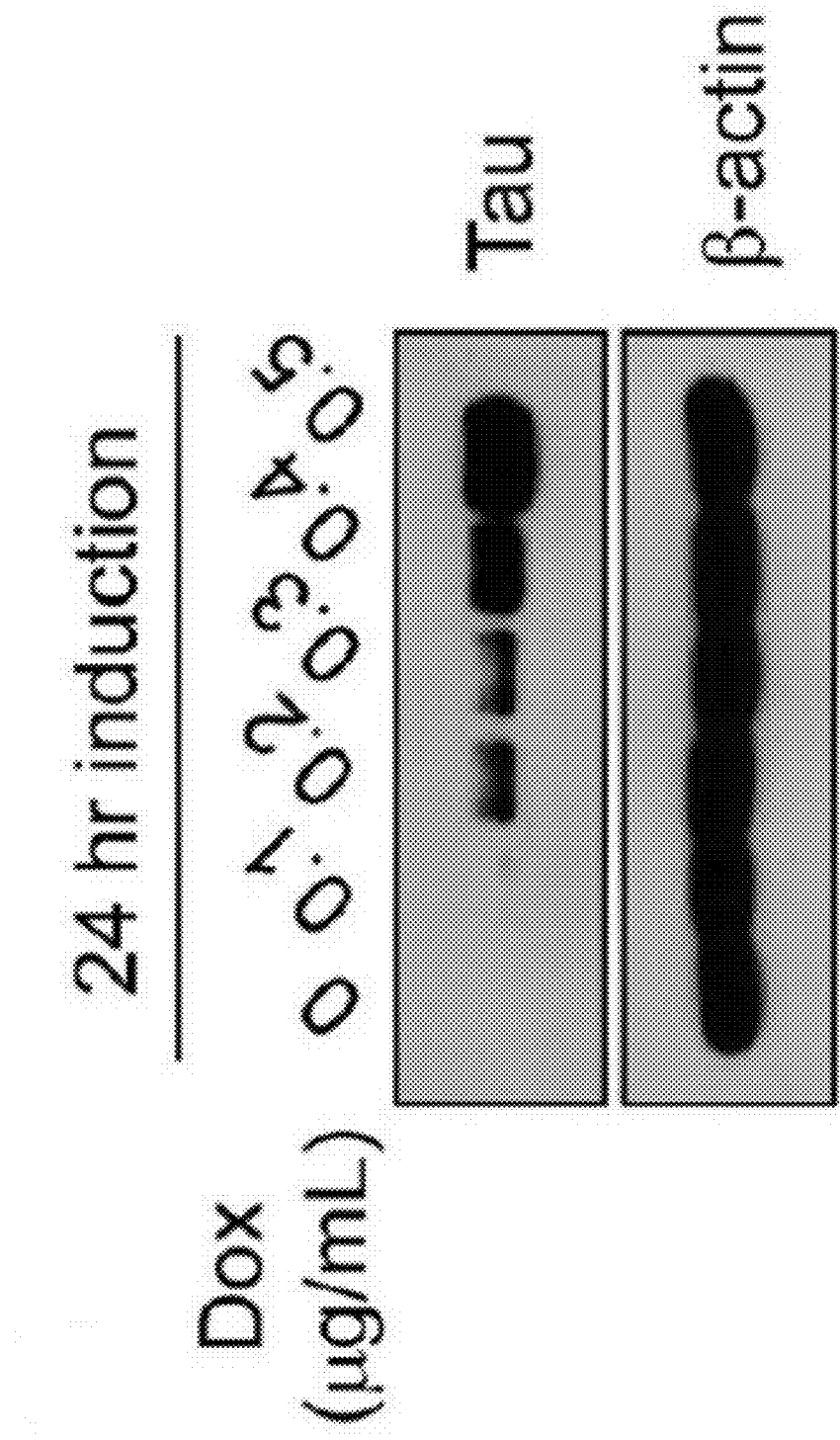

In order to examine whether the external proteasome delivery affects the proteolysis in living cells, HEK293-induced cell line was used, which expresses the longest isoform (htau40) of human tau on doxycycline induction (inducible tau cell line). The protein samples were prepared at the presence and absence of reductant and β-mercaptoethanol (βME), and the aggregated tau proteins and their truncated forms were detected in the inducible cell line after treatment with Dox (0.5 μg/mL) for the indicated time duration. These cells expressed htau40 in a high dose-dependent manner, and gradually moved tau species after 2 days of culturing in accordance with the formation of SDS-resistance tau aggregates (FIG. 20a and FIG. 20b). Tau, especially in the early stage of the progression of tau disease and Alzheimer's disease (AD), is considered to be decomposed by the ubiquitin-proteasome system.

Figure 21A:
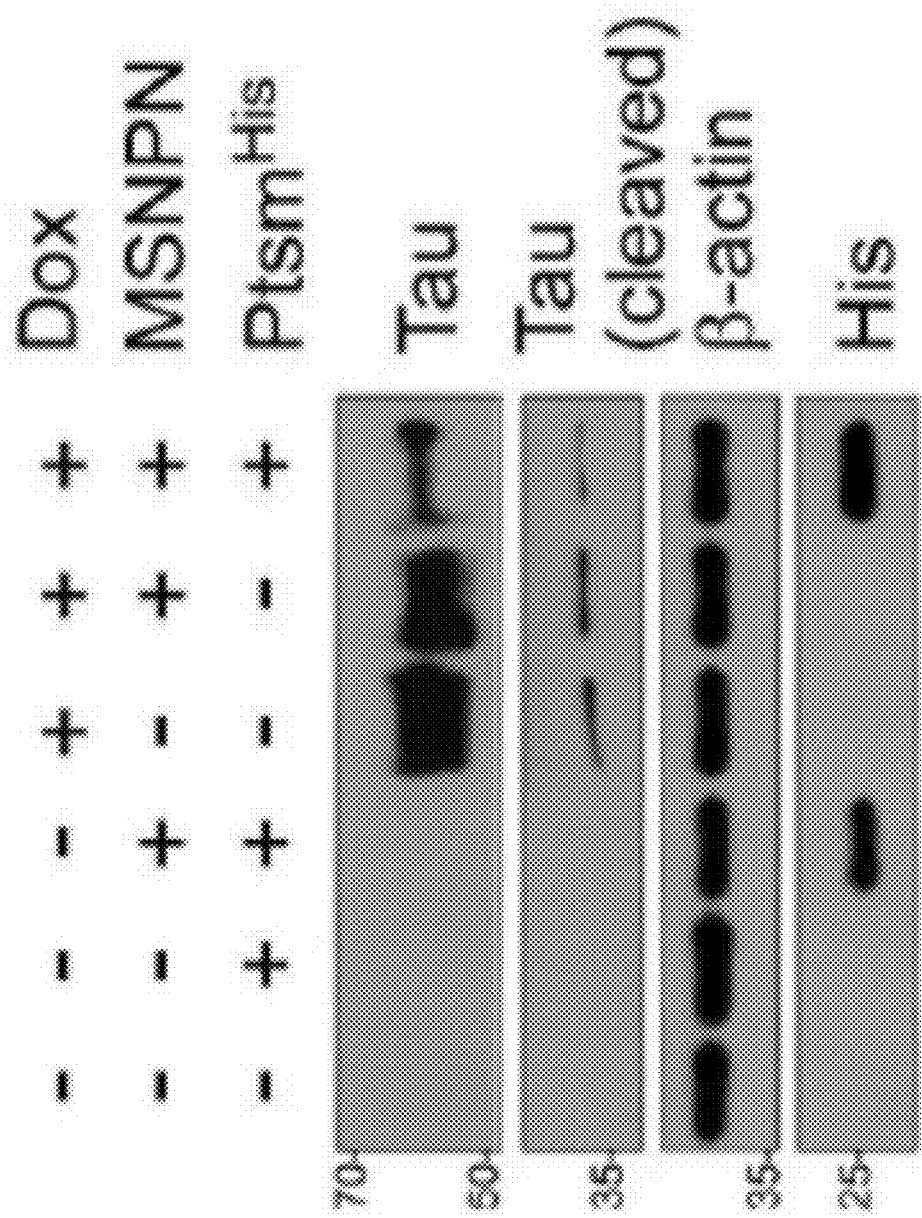
FIGS. 21a and 21b are graphs showing the SDS-PAGE/IB images and quantitative analysis result regarding inducible tau cell line treated with Dox, MSNPN and proteasome-MSNPN according to one embodiment of the present invention.
Figure 21B:
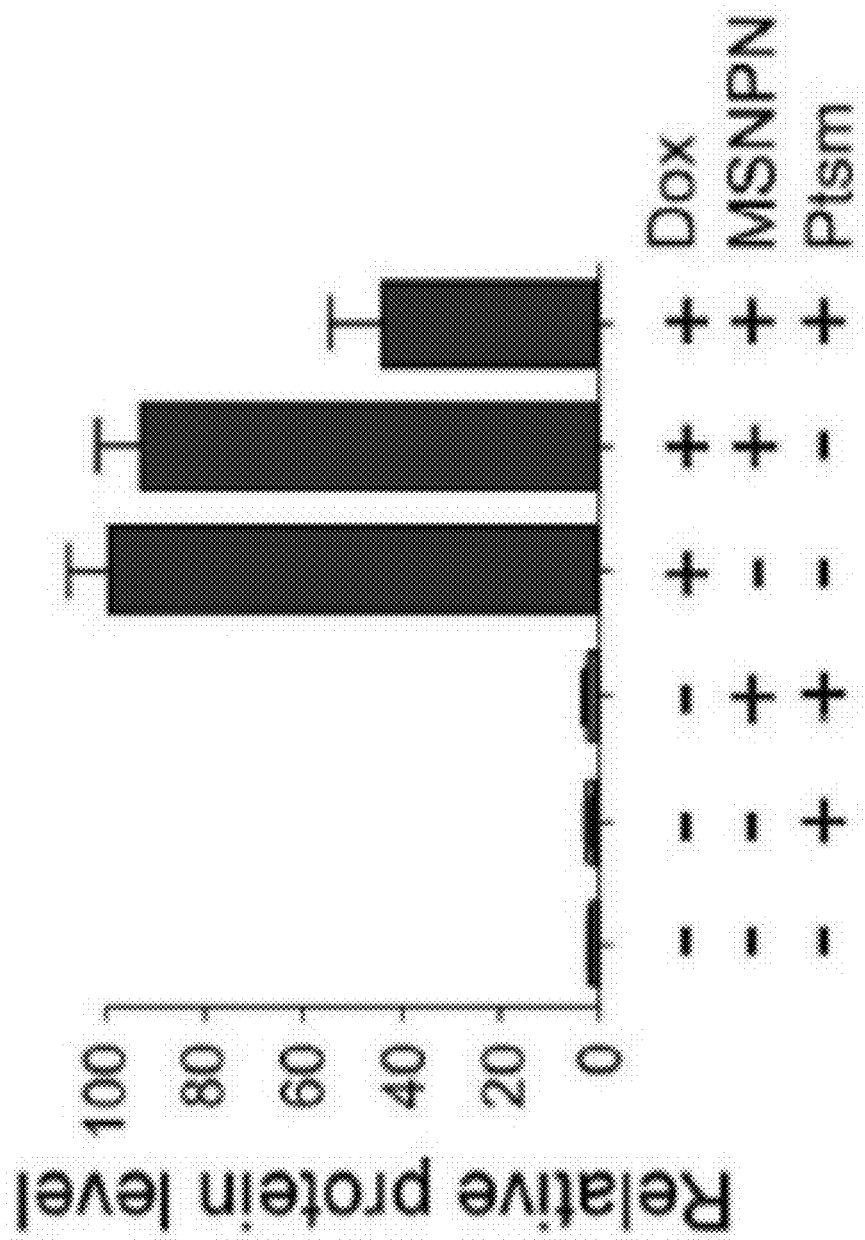

The inducible tau strains were treated with Dox (0.5 μg/mL, 24 hours), MSNPN (5 μg/mL) and proteasome-MSNPN complex (50 μg/mL, 1:50 molar ratio, 24 hours), and the treated samples were analyzed by SDS-PAGE/IB. His IB is for the β4 subunit of an external proteasome. The samples were treated with Dox in various concentrations (0, 0.5, 1, 5, and 10 ng/mL), MSNPN, and/or human proteasome, and then tau levels were quantitated by a densitometer for the film images through 3 independent experiments (n=3). The over-expressed tau level was remarkably decreased when the purified proteasome was delivered by MSNPN, whereas almost no effect was found by the treatment with nanoparticles alone (FIG. 21a and FIG. 21b). The level of truncated tau, which is known to have toxicity and aggregation property, was also remarkably decreased by proteasome-MSNPN treatment. The accelerated decomposition of tau was dependent on the amount of the delivered proteasome (0, 5, 10, 25, and 50 μg/mL, 1:50 ratio).

In order to confirm the tau regulation after the translation of an external proteasome, quantitative RT-PCR was conducted using primers for tau and glyceraldehyde 3-phosphate dehydrogenase (GAPDH) (control for normalization). The total RNA from the cultured cells was prepared with TRIzol reagent (Invitrogen), which was further purified by RNeasy mini-column (Qiagen) as well as on-column DNase I treatment. cDNA sample was prepared by reverse transcription using Accupower RT pre-mix (Bioneer). Then, the samples were subjected to PCR by Rotor-Gene RG 3000 (Corbett Research, Sydney, AU) along with diluted cDNA, SYBR qPCR master mixture (KAPA biosystem) as a reporter dye, and 10 pmole of a gene-specific primer. The conditions of heating cycles included enzyme activation at 95° C. for 3 min, 40 cycles at 95° C. for 10 sec, at 53° C. for 15 sec, and at 72° C. for 30 sec. Each mRNA level was normalized to the GAPDH level and the values were plotted as the mean±SD of three independent experiments. The used primer sequences are as following: the forward primer (5'-aaggtgacctccaagtgtgg(SEQ ID NO: 15)-3') and the reverse primer (5'-gggacgtgggtgatattgtc(SEQ ID NO: 16)-3') for tau; the forward primer (5'-gagtcaacggatttggtcgt(SEQ ID NO: 17)-3') and the reverse primer (5'-gacaagcttcccgttctcag (SEQ ID NO: 18)-3') for GAPDH.

The tau mRNA levels were similar under the above condition, which strongly suggests that the external proteasome directly accelerates the decomposition of the over-expressed tau (FIG. 22a). The delivered proteasome did not affect the autophagocytosis flow or the level of proteasome substrates such as Nrf2 and p53. Therefore, the external proteasome delivered to the cells, instead of being involved in the decomposition of noxious non-specific proteolysis, degrades the protein substrates more efficiently which abnormally give the absorption and loading to UPS such as the over-expressed tau. The task in the future would be identifying the distinctive property of the target protein which is the basis of the different sensitivities to proteasome decomposition, e.g., the frequency of hyperphosphorylation and the specificity of Ub connection of tau.

Figure 22B:
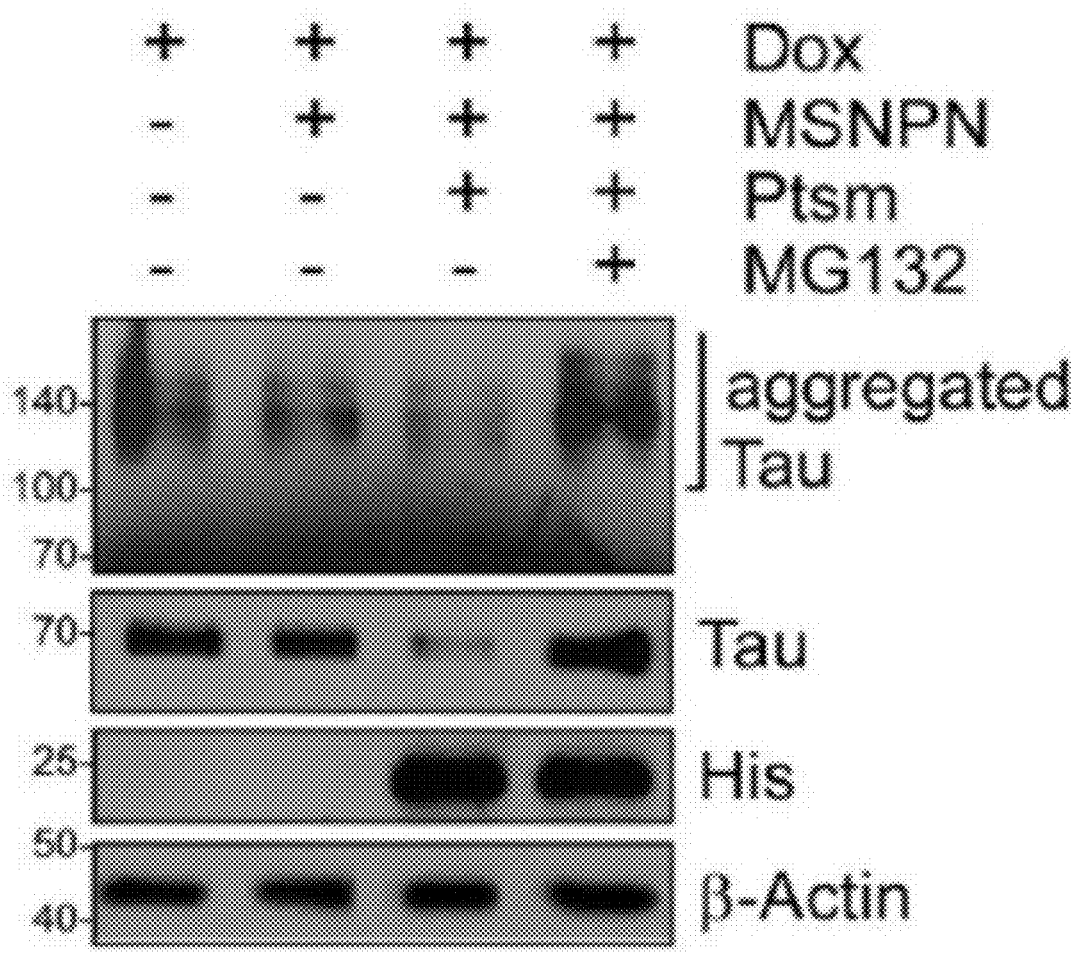
FIG. 22b is an SDS-PAGE/IB image of the cells treated with MG132, regarding the cells treated with Dox, MSNPN and proteasome-MSNPN.
Figure 23:
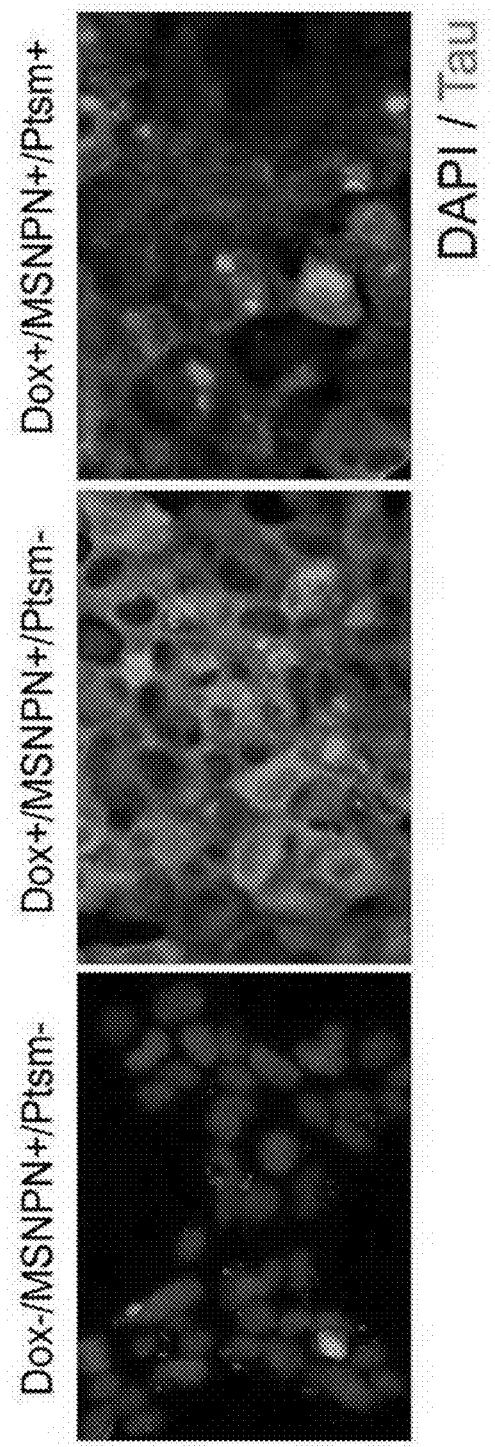
FIG. 23 is a microscopic fluorescence analysis image using tau immunostaining and DAPI counter-staining according to one embodiment of the present invention.

The delivery of proteasome using MSNPN effectively delayed the formation of tau aggregates which is a pathological characteristic of AD (FIG. 22b). This effect was dependent on autophagocytosis, and the accelerated proteasome decomposition of the soluble tau protein may have preceded (FIG. 21a and FIG. 23). However, this effect was removed by treating the cells with a proteasome inhibitor, 10 μg of MG132, which led to the significant accumulation of both soluble tau and tau aggregates (FIG. 22b). Specifically, the level of huntingtin protein was not changed by the treatment of proteasome-MSNPN, and it was impossible to be treated with proteasome. Therefore, the above effect of the external proteasome at a protein level was limited by the UPS substrate.

Example 16: Quantitation of Tau Oligomerization

In order to visualize and quantitate the tau oligomerization in living cells, tau cells were used which have fluorescent complementarity (BiFC) of biomolecules. HEK293-derived stable cell line (tau-BiFC), which inherently expresses both the N- and C-terminals of Venus protein independently fused to the htau40, were prepared in accordance with the prior art [Zhang, X., et al. The proteasome: A target of oxidative damage in cultured human retina pigment epithelial cells. IOVS 49, 3622-3630 (2008)]. Tau-BiFC cells were inoculated to 96-wells at $10^5$ cells/well density and cultured in DMSO or 30 nM okadaic acid (OA)

for 24 hours to accelerate tau oligomerization. The fluorescence images were obtained, and quantitated and analyzed by using Operetta (PerkinElmer).

The N- and C-terminals of the Venus protein were independently fused to the htau40, which showed only basic fluorescence signals under the normal condition. However, the fluorescence was strongly "turned-on" by chemical induction of hyperphosphorylation such as okadaic acid, which resulted in the tau oligomerization.

Tau-BiFC cell line was treated with 50 μg/mL MSNPN and proteasome-MSNPN, and then the quantitated tau-oligomer levels were compared; the values represent the average (±SD) of three independent cultures containing a total of ~10,000 cells. The tau-BiFC cells which were in accordance with inducible tau cells and treated with Proteasome-MSNPN complex, showed significantly less tau aggregations than the cells treated with MSNPN alone. This result suggests that the tau protein aggregation process can be delayed during the protein toxicity condition by the direct delivery of an external proteasome using MSNPN.

Example 17: Evaluation of Cell Survival and Reductive Stress

In order to measure the cell survival and the reductive stress by ROS inducer para R (paraquat) under the condition of tau induction by Dox, inducible tau cell line was previously cultured in 250 pg/mL Dox and 1 mM para-R for 3 hours, and then treated with MSNPN or proteasome-MSNPN complex for 12 hours.

The cell survival was measured by CCK-8 (cell counting kit-8) analysis (Dojindo Laboratory, Japan). HeLa cells were inoculated into 960-well cell culture plates at $1 \times 10^4$ cells per well 24 hours prior to the nanoparticle treatment. After incubation for 24 hours, the cells were treated with MSNPN or proteasome-MSNPN in various concentrations. The control cells were treated with PBS of the same volume. The medium was removed after 24 hours, and 100 mL of serum-free medium and 10 mL of CCK-8 solution were added to each well. The cells were incubated for 2 hours. The optical density of formazan salt was measured by a microplate reader (Molecular Devices, Inc., USA) at 450 nm wavelength with the background absorbance excluded. The experiment was repeated 3 times and the data were expressed as mean±SD.

The values indicates mean±SD (n=5). (note **, p<0.01). The delivery of proteasome remarkably alleviated the cytotoxicity induced by over-expressed tau and a ROS inducer parameter R, indicating that this method can be used to reduce the protein toxicity and the oxidative stress from the cells.

This Example reports that a high molecular weight protein complex such as human proteasome can be directly delivered to cells by using a chemically modified mesoporous nanoparticle. The external proteasome maintains its activity and functionality when it is bound to MSNPN or after it is internalized into cells through endocytosis. The increased proteasome of cells according to this method was acceptable to the cells and did not induce non-specific proteolysis. Remarkably, the cells with external proteasome showed accelerated decomposition of soluble tau, the delayed accumulation of tau aggregates, and enhanced resistance to the protein toxicity stress mediated by tau and ROS. In order for silica nanoparticles to become permeable through the blood-brain barrier, this strategy can be an interesting alternative for the toxic aggregative protein accumulated in neurons considering the inactivity, the non-antigenicity, modifiability, and the fact that the in situ regulation of proteasome biosynthesis or proteasome activity has not been developed yet. Since a number of diseases are caused by toxic misfolded aggregative proteins, the range of proteasome delivery is not limited to neurodegenerative diseases. Therefore, the direct delivery of proteasome may be a potentially beneficial intervention for the cells under the condition of protein toxicity or oxidative stress.

Preparation Example 8: Synthesis of MSN Surface-Modified with Glutathione (GSH)

Figure 24:
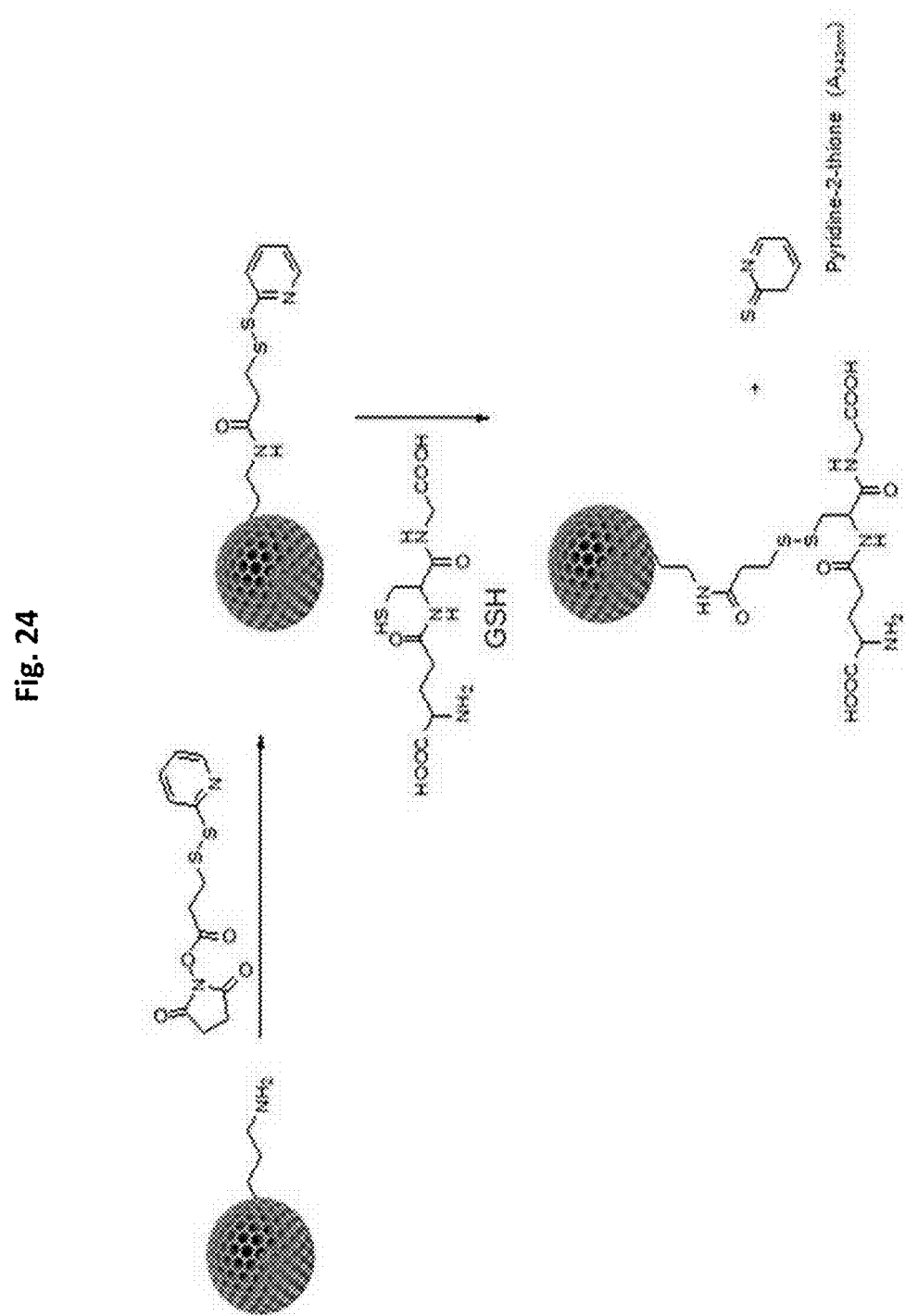
FIG. 24 is a schematic figure of the surface-modified mesoporous silica nanoparticle synthesis according to one embodiment of the present invention.

The synthesis of mesoporous silica nanoparticles surface-modified with glutathione (GSH-MSN) is conducted as shown in FIG. 24. First, using ep-tube, 50 mg of MSN surface-modified to have expanded pores and a positive charge was dissolved in 1 mL of Dimethyl sulfoxide (DMSO), and sufficiently dispersed. Then, 20 mg of succinimidyl 3-(2-pyridyldithio)propionate (SPDP) linker with the average molecular weight of 312.37 and the spacer arm length of 0.68 nm was added to the ep-tube, which was sufficiently reacted using an orbital shaker at RT for 24 hours to allow for the even mixing and reactions of the two substances. When the reaction was completed, the product was precipitated by centrifugation, and washed with DMSO and ethanol to remove SPDP which did not react but remained; this process was repeated 3 times; and the precipitated product after the final ethanol wash was dispersed in 1 mL of the tertiary distilled water. And then, glutathione with the average molecular weight of 307.33 was added thereto, and allowed to react in the orbital shaker at RT for 24 hours, then the product was precipitated by centrifugation and washed with distilled water and ethanol 5 times each, and the remaining solvent was removed by a vacuum pump. The quantitation of glutathione can be conducted by measuring the absorbance (A343 nm) of pyridine-2-thione dissolved in the supernatant by using the UV-visible light spectrophotometer. The synthesized particles were dispersed in distilled water and stored at 4° C. for their application in later Examples.

Example 18: Analysis of Protein Loading to MSN Surface-Modified with Synthesized Glutathione, and Introduction into Cells In order to verify the effective delivery and function of the effective components of the synthesized nanoparticle, the protein tagged with glutathione S-transferase (GST) was loaded. For this sake, as in Preparation Example 8, GST-tagged ribonuclease (RNase) was used, which was tried to be loaded by the GSH-GST interaction between the GSH inside GSH-MSNG and the GST of RNase, and the particles were analyzed by UV-visible light absorption spectrometry before and after the loading. In case of the particles loaded with GST-tagged RNase, the rate of protein loading was measured through the absorbance of the GST-tagged RNase which was not loaded but remained in the supernatant, which was calculated by Beer-Lambert formula using the absorbance values at 278 nm and the pre-reported absorbance coefficient ($\varepsilon=9,800M^{-1}$ cm$^{-1}$), based on the intensity of the absorbance.

$$A = \varepsilon b c$$

[A: the measured absorbance intensity, ε: the absorbance coefficient, b: the path length of the measuring vessel (1 cm), c: the molar concentration of the substance]

Figure 25:
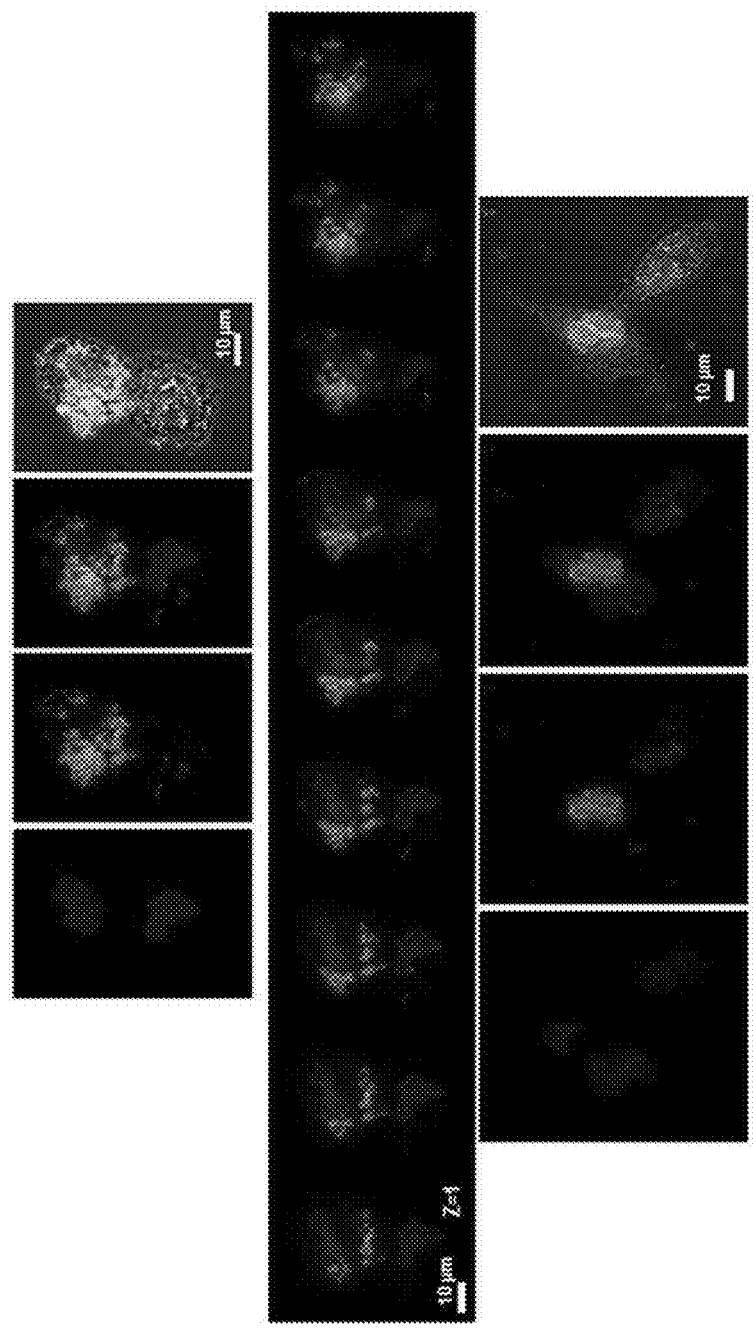
FIG. 25 is the images showing the inflow of the composition for delivering a protein according to one embodiment of the present invention into cells.

The result of UV-visible light absorption spectrometry indicated that 4 μg of GST-tagged RNase can be loaded per 10 μg of GSH-MSN. The present inventor considered, based on the successful loading of the effective component for a specific purpose to MSN, that the MSN can play a role as a carrier which is acceptable in the pharmaceutical delivery of an effective substance and therapeutic research at the levels of cells, animals and humans; to verify this, the GST-tagged RNase was loaded to the GSH-MSN to verify the efficiency of introduction into the cells. In order to observe the introduction into the cells at human cell level by fluorescence microscope using a specific fluorescent filter, RNase was stained with a fluorescent dye and loaded to nanoparticles. 50,000 cells of THP-1 cell line were dispensed into 12-well culture plates and, 24 hours later, Phorbol 12-myristate 13-acetate (PMA) was added thereto to allow the cells to differentiate, and then 4 μg of GST-tagged FAM-RNase was loaded to GSH-MSN and treated with serum-free cell culture media for 4 hours. And then, the remaining substances were washed with 1×PBS twice and the culture media was replaced with new media containing serum for the additional cell growth at 5% $CO_2$ and 37° C. for 12 hours; the cells were observed by the confocal fluorescence microscope with a fluorescent filter at 358 nm and 492 nm, where fluorescence values represent the cell nucleus fluorescence (358 nm, blue) and GST-tagged RNase fluorescence (492 nm, green), respectively. As shown in FIG. 25, the strong green fluorescence of the protein was evenly observed at the cytoplasm around the nucleus, and it was verified through the cell fluorescence images that the green fluorescence was distributed obviously not on the outer surface of cell but in the cytoplasm, which allowed us to confirm that the nanoparticle synthesized by the present researchers can play a role as a carrier acceptable in the pharmaceutical delivery of an effective substance and therapeutic research even regarding the cell line known for the difficulty of introduction of an external substance into the cells.

Figure 26A:
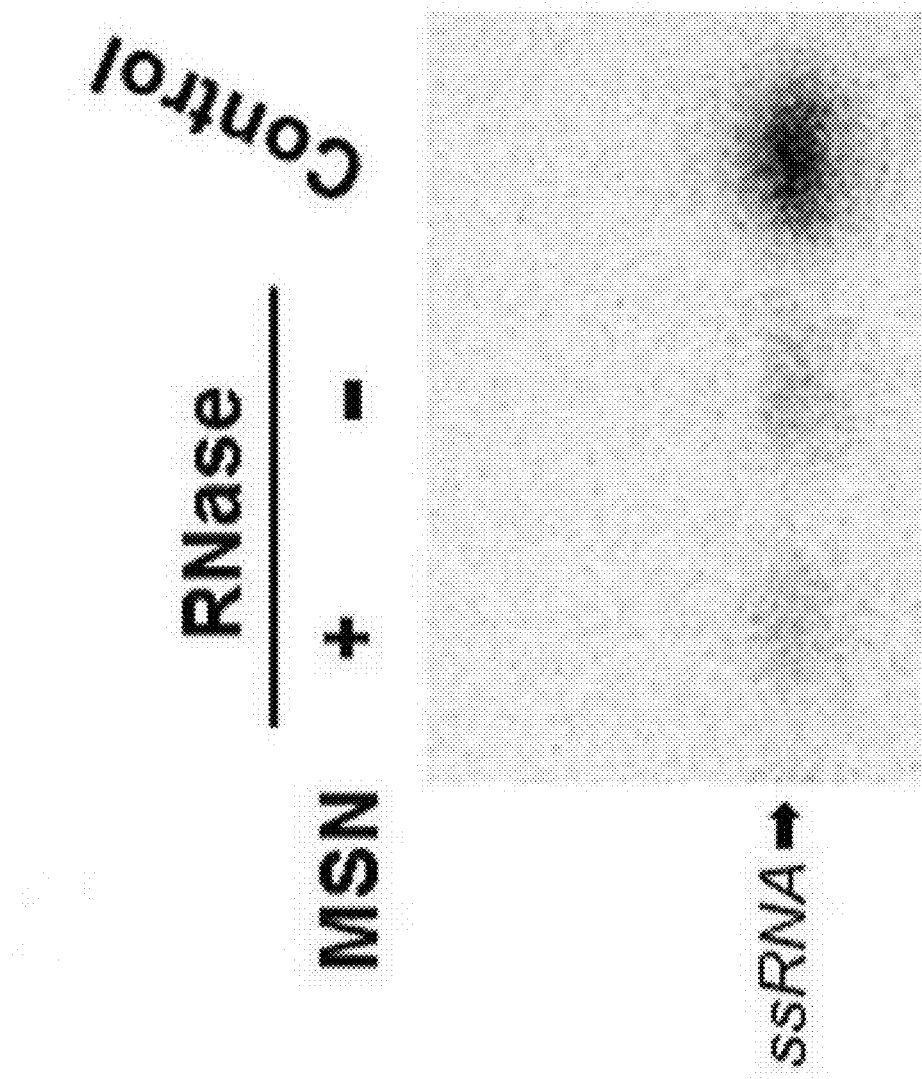
FIGS. 26a and 26b show the analysis result on the RNase delivery and the functional effectiveness regarding a composition for delivering a protein according to one embodiment of the present invention.
Figure 26B:
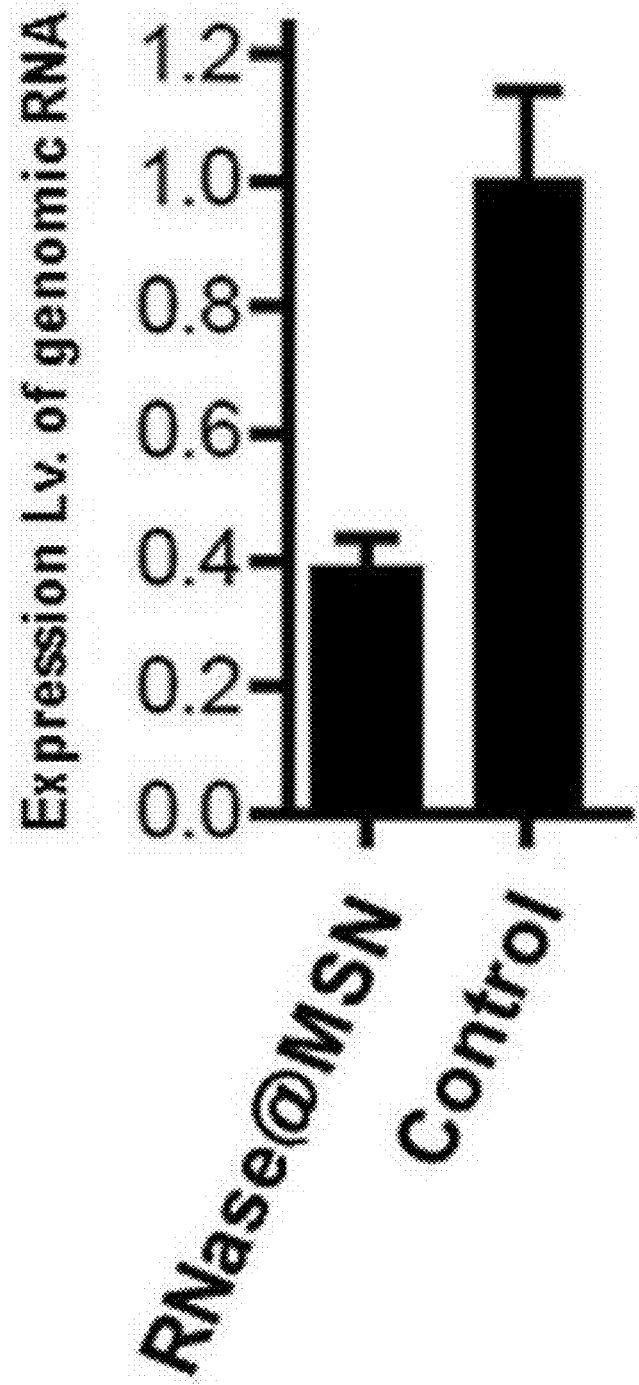

Example 19: Verification of Effectiveness of Protein Delivery Using GSH-MSN at Human Cell Level It was examined whether the synthesized GSH-MSN with correctly loaded protein, an effective substance, was introduced into cells and released it into the cytoplasm so that the expression levels of nucleic acids such as DNA and RNA can be regulated. If the RNase to be loaded can be effectively loaded and stably released, it can decompose the targeted single-chain nucleic acid, and thereby be applicable for the therapeutic purpose of inhibiting potential diseases caused by nucleic acids. To verify the above efficacy, targeting a specific RNA expressed in THP-1 cell line, the RNase decomposing the specific RNA was determined as a candidate protein, and in vitro experiments were conducted at the presence of 1×PBS buffer solution and 10 mM $MgCl_2$. RNase@MSN was prepared in Ep-tube, and single-stranded RNA (ssRNA) was added thereto and reacted at 37° C. for 30 min, and then the RNA decomposition was verified by gel-electrophoresis. As shown in FIGS. 26a and 26b, it was found that the RNase loaded to the nanoparticle functioned effectively, and the potential as a therapeutic function at the cellular level was verified thereafter. 50,000 cells of THP-1 cell line were dispensed in 12-well culture plates and allowed to differentiate by adding Phorbol 12-myristate 13-acetate (PMA) thereto after 24 hours, and then 4 μg of GST-tagged RNase was loaded to GSH-MSN, which was then treated with cell culture media without serum for 4 hours. Then the remaining substance were washed with 1×PBS twice, and the culture media were replaced with new media containing serum and the cells were allowed to grow further in 5% $CO_2$ and 37° C. environment for 12 hours, and then the expression levels of specific RNAs were compared by qRT-PCR using gel electrophoresis. FIGS. 26a and 26b show the analysis result of the delivery and functional effectiveness of the RNase which inhibits specific RNA expression, wherein (a) is an image showing the result of analyzing whether RNA decomposition took place through the gel electrophoresis, an in vitro activity assay of RNase at ep-tube stage, and (b) is a graph showing analysis of the expression levels of the specific RNA in THP-1 cell line using qRT-PCR. As shown in FIGS. 26a and 26b, in the case of the delivery of RNase by MSN, RNA expression-inhibiting efficiency of about 5 to 60% was obtained, and it was considered that the nanoparticle the present researchers synthesized could play a role as a delivering agent acceptable for the delivery of a pharmaceutically effective substance suitable for a purpose such as, but not limited to, a protein, and a therapeutic research, even regarding the cell line in which it is relatively difficult to introduce a foreign substance into the cells.

Example 20: Examination of Protein Delivery in In Vivo Animal Model Using MSN

Figure 27:
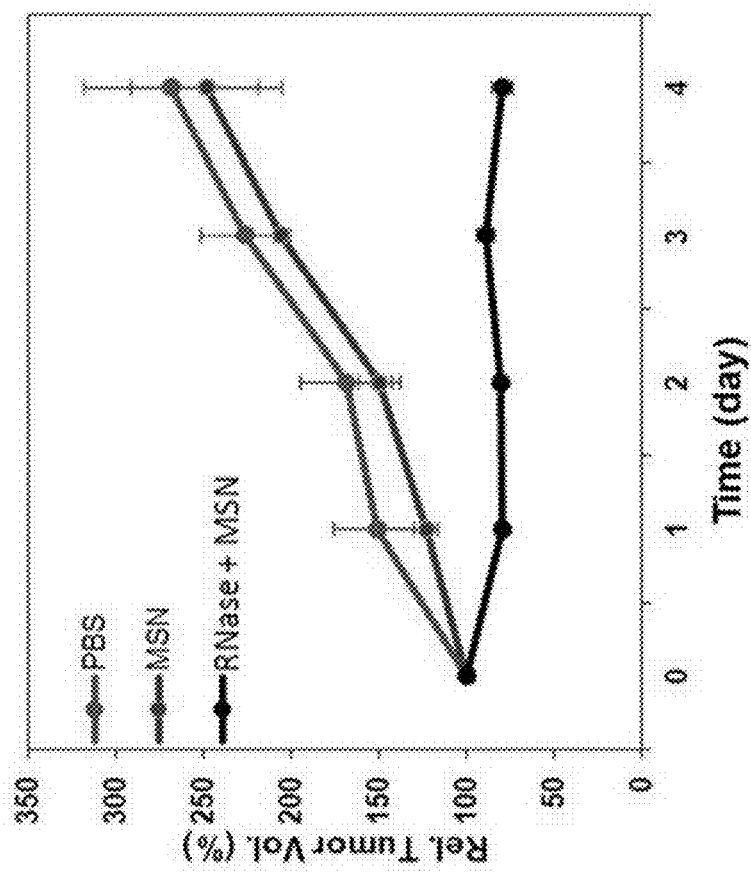
FIG. 27 is a graph showing the RNase delivery and resultant reduction in tumor size regarding a composition for delivering a protein according to one embodiment of the present invention.

Based on the effective protein delivery result at a cellular level, in order to verify the potential of the nanoparticle to play a role as a delivering agent acceptable for the delivery of a pharmaceutically effective substance and a therapeutic research at an animal level, mouse was used as an experimental object. More particularly, Balb/c nude male mice were purchased from Orient bio Co., and RNase (Sigma Aldrich Korea) was prepared for injection into the mice by loading the RNase to MSN containing anions by electrostatic force in 1×PBS (pH 7.4) condition. HeLa cells were implanted to 5 week-old mice to grow xenograft tumors, and the therapeutic effect of the RNase delivery on the tumors were observed. 3,000,000 HeLa cells were dispersed in sterile 1×PBS, which were then administered subcutaneously into the mice, and when the tumor grew to 70 $mm^3$, PBS, MSN and the MSN loaded with RNase were injected into the tumors of the mice, respectively. As shown in FIG. 27, in the mice injected with PBS or MSN alone, tumor growth inhibition effect was not observed, while the mice injected with the MSN loaded with RNase showed decrease in the tumor size by about 3- to about 4-fold. The animal experimental result indicated that the MSN according to the present invention can play a role as a delivering agent acceptable for the delivery of a pharmaceutically effective substance and a therapeutic research.

Example 21: Evaluation of Protein Delivery in In Vivo Animal Model Using MSN

Figure 28A:
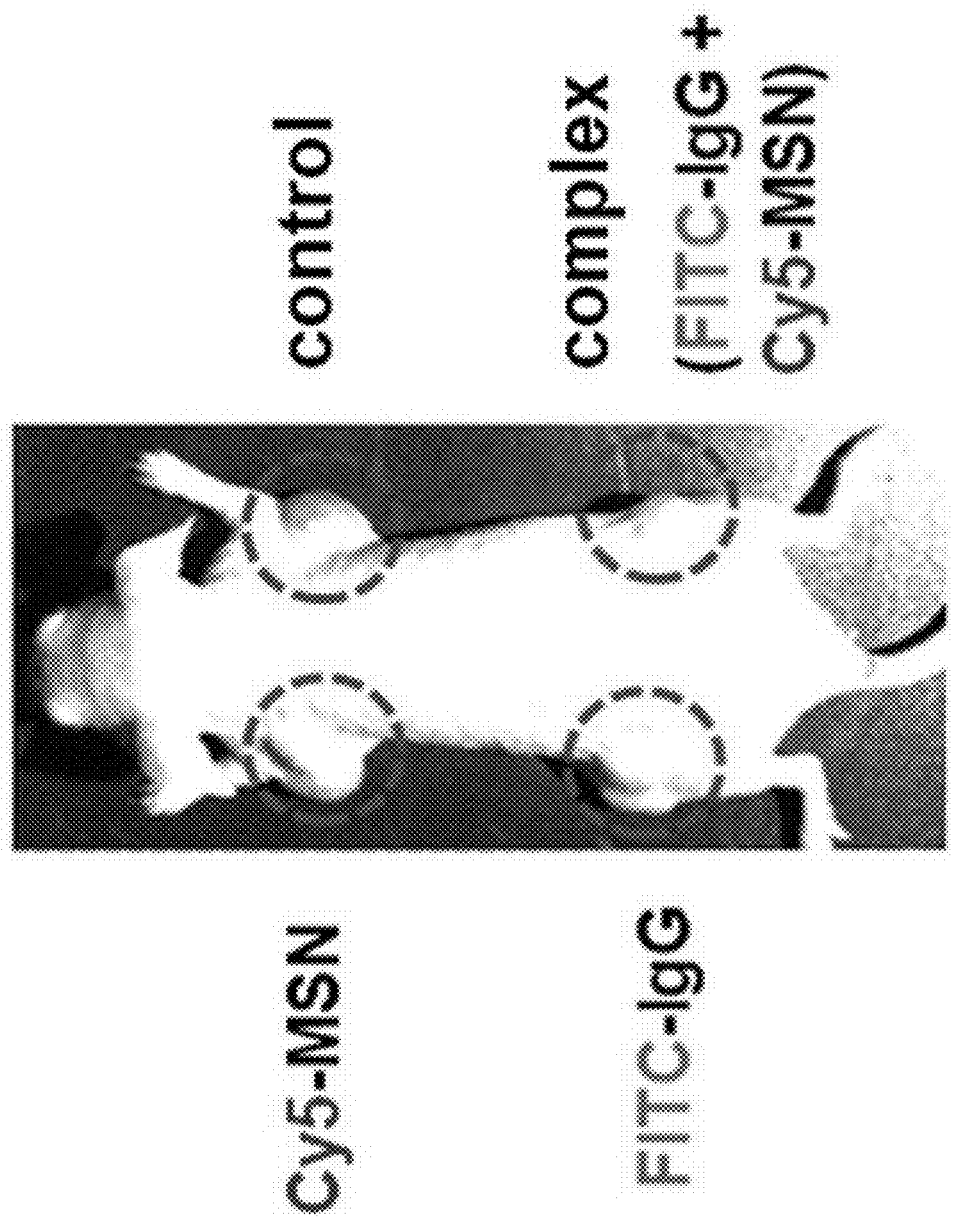

Based on the effective protein delivery result in a cellular level, in order to verify the potential of the nanoparticle to play a role as a delivering agent which is stable and effective at an animal level, mouse was used as an experimental object. More particularly, Balb/c nude male mice were purchased from Orient bio Co., MSN having cations conjugated with FITC fluorescent dye (Cy5-MSN) was prepared, and the immunoglobulin G (FITC-IgG, Sigma Aldrich Korea) conjugated with FITC fluorescent dye was prepared for injection into the mice by loading it by an electrostatic force in 1×PBS (pH 7.4) condition. HeLa cells were implanted to 5 week-old mice to grow xenograft tumors, and the fluorescence intensity and distribution according to the delivery of FITC-IgG and Cy5-MSN were observed by Optix Mx3 (GE Healthcare, USA) device. 3,000,000 HeLa cells were dispersed in sterile 1×PBS, which were then administered subcutaneously into the mice, and when the tumor grew to 70 mm$^3$, PBS, Cy5-MSN, FITC-IgG and Cy5-MSN loaded with FITC-IgG were injected into the tumors of the mice, respectively. As shown in FIGS. 28a and 28b, MSN and IgG showed good delivery to the tumor tissue, and the IgG not loaded to MSN showed relatively rapid disappearance of a fluorescent signal after injection into the tumor as compared to the IgG loaded to MSN. The animal experimental result indicated that the MSN according to the present invention can effectively maintain high stability and the function of a pharmaceutically effective substance, and thereby can play a role as a delivering agent acceptable for a therapeutic research.

The above description of the embodiments is provided for the purpose of illustration, and it would be understood by those skilled in the art that various changes and modifications may be made without changing technical conception and essential features of the embodiments. Thus, it is clear that the above-described embodiments are illustrative in all aspects and do not limit the present disclosure. For example, each component described to be of a single type may be implemented in a distributed manner. Likewise, components described to be distributed may be implemented in a combined manner.

The scope of the inventive concept is defined by the following claims and their equivalents rather than by the detailed description of the embodiments. It shall be understood that all modifications and embodiments conceived from the meaning and scope of the claims and their equivalents are included in the scope of the inventive concept.

The invention claimed is:

1. A composition for delivering a bioactive material, comprising:
   an expanded porous silica nanoparticle having an expanded pore structure, a surface of the expanded porous silica nanoparticle comprising a pore surface forming the pores and an outer surface, the expanded porous silica nanoparticle produced by a process comprising:
      stirring a mixture of a silica precursor having a pore diameter of less than 5 nm with a surfactant; and
      treating the silica nanoparticle with an expanding agent to prepare a mixture, and heating the mixture, and removing the surfactant to obtain the expanded porous silica nanoparticle with a pore diameter of 10 nm to 100 nm;
   at least one of (i) a functional group which binds to the pore surface of the expanded porous silica nanoparticle and gives the pore surface a negative charge or a positive charge, (ii) a ligand which binds to the pore surface of the expanded porous silica nanoparticle and specifically binds to the bioactive material, wherein the ligand includes nickel, nickel-nitrilotriacetic acid, glutathione, dextrin, biotin or streptavidin, and (iii) a combination of the functional group and the ligand; and
   a bioactive material having a size to be accommodated within the pores of the expanded porous silica nanoparticle, the bioactive material bound to said at least one of the functional group and the ligand bound to the pore surface of the expanded-silica nanoparticle and accommodated within the pores of the expanded porous silica nanoparticle,
   wherein the bioactive material is a protein having a size from 14.7 kDa to 2,000 kDa; and
   the protein is a 26S human proteasome.

2. The composition according to claim 1, wherein the composition comprises the ligand which includes nickel, nickel-nitrilotriacetic acid, glutathione, dextrin, biotin or streptavidin.

3. The composition according to claim 1, further comprising at least one material selected from the group consisting of an antibody, a ligand, a cell-permeable peptide, and an aptamer, said at least one material bound to the outer surface of the expanded porous silica nanoparticle.

4. The composition according to claim 1, further comprising at least one material selected from the group consisting of an antibody, a ligand, a cell-permeable peptide, and an aptamer, said at least one material bound to the outer surface of the expanded porous silica nanoparticle.

5. The composition according to claim 1, wherein the expanded pore diameter ranges from 20 nm to 100 nm.

6. The composition of claim 1, wherein the expanded porous silica nanoparticle is produced by:
   mixing the silica precursor and a surfactant for 8 hours to form the mesoporous silica nanoparticle with the pore diameter of less than 5 nm; and
   treating the mesoporous silica nanoparticle with the expanding agent to expand the pore diameter to 10 nm to 100 nm.

7. The composition of claim 1, wherein the surfactant comprises cetyltrimethylammonium bromide (CTAB); and
   the expanding agent comprises trimethylbenzene (TMB).

8. A composition for delivering a bioactive material, comprising:
   an expanded porous silica nanoparticle having an expanded pore structure, a surface of the expanded porous silica nanoparticle comprising a pore surface forming the pores and an outer surface, the expanded porous silica nanoparticle produced by forming a mesoporous silica nanoparticle with a pore diameter of less than 5 nm by mixing a silica precursor of tetramethoxy silane (TMOS) with a surfactant comprising at least one selected from the group consisting of cetyltrimethylammonium bromide (CTAB), hexadecyltrimethylammonium bromide (TMABr), hexadecyltrimethylpyridinium chloride (TMPrCl), and tetramethylammonium chloride (TMACl) for at least 8 hours, sonicating a solution containing the mesoporous silica nanoparticle, and treating the mesoporous silica nanoparticle, at the temperature of 80° C. to 200° C., with an expanding agent comprising at least one selected from the group consisting of trimethylbenzene (TMB), and N,N-dimethylhexadecylamine (DMHA) to prepare a mixture, and heating the mixture, and removing the surfactant to obtain the expanded porous silica nanoparticle with a pore diameter of 10 nm to 100 nm;
   at least one of (i) a functional group which binds to the pore surface of the expanded porous silica nanoparticle and gives the pore surface a negative charge, (ii) a ligand which binds to the pore surface of the expanded porous silica nanoparticle and specifically binds to the bioactive material, and (iii) a combination of the functional group and the ligand; and
   a bioactive material having a size to be accommodated within the pores of the expanded porous silica nanoparticle, the bioactive material bound to said at least one of the functional group and the ligand bound to the pore surface of the expanded-silica nanoparticle and accommodated within the pores of the expanded porous silica nanoparticle, wherein the bioactive material is a protein having a size from 14.7 kDa to 2,000 kDa; and the protein is a 26S human proteasome.

9. A method for delivering the bioactive material, the method comprising introducing the composition of claim 1 into a target cell.

10. The method according to claim 9, wherein the introduction of the composition into the target cell comprises adding said composition to a cell culture medium to introduce said composition into the target cell.

11. The method according to claim 9, wherein the introduction of the composition comprises introducing the composition into the target cell by intravascular administration, oral administration, transdermal administration, or local administration by injection.

* * * * *